United States Patent
Takahashi et al.

(10) Patent No.: US 7,586,091 B2
(45) Date of Patent: Sep. 8, 2009

(54) MASS SPECTROMETRIC SYSTEM AND MASS SPECTROMETRY

(75) Inventors: Katsutoshi Takahashi, Tokyo (JP); Kazuhiro Iida, Tokyo (JP); Masakazu Baba, Tokyo (JP); Noriyuki Iguchi, Tokyo (JP); Toru Sano, Tokyo (JP); Hisao Kawaura, Tokyo (JP); Toshitsugu Sakamoto, Tokyo (JP); Wataru Hattori, Tokyo (JP); Hiroko Someya, Tokyo (JP)

(73) Assignee: NEC Corporation, Tokyo (JP)

( * ) Notice: Subject to any disclaimer, the term of this patent is extended or adjusted under 35 U.S.C. 154(b) by 301 days.

(21) Appl. No.: 10/549,587

(22) PCT Filed: Mar. 15, 2004

(86) PCT No.: PCT/JP2004/003427

§ 371 (c)(1),
(2), (4) Date: Mar. 23, 2006

(87) PCT Pub. No.: WO2004/081555

PCT Pub. Date: Sep. 23, 2004

(65) Prior Publication Data

US 2006/0214101 A1    Sep. 28, 2006

(30) Foreign Application Priority Data

Mar. 14, 2003    (JP) .............................. 2003-069793

(51) Int. Cl.
*H01J 49/00* (2006.01)
(52) U.S. Cl. .................. 250/288; 250/281; 250/282; 435/6; 204/451; 204/452; 204/453

(58) Field of Classification Search ................ None
See application file for complete search history.

(56) References Cited

U.S. PATENT DOCUMENTS 4,705,616 A    11/1987    Andreson et al.

(Continued)

FOREIGN PATENT DOCUMENTS

JP    63-318061    12/1988

(Continued)

OTHER PUBLICATIONS

Kazuhiko Fukui, et al., "ESI-FTICR MS With Infrared Multiphoton Dissociation: Analysis of Fragmentation of Peptides", Proceedings of the 50th ASMS Conference on Mass Spectrometry and Allied Topics, Jun. 2002.

*Primary Examiner*—David A. Vanore
(74) *Attorney, Agent, or Firm*—Scully, Scott, Murphy & Presser, P.C.

(57) ABSTRACT

After a sample is previously separated into plural components in a channel formed in a microchip (353), the channel is irradiated along a separation direction with a laser beam from a laser oscillator (361) to sequentially ionize each fraction separated in the channel. The ionized fraction is detected by a mass spectrometry unit (363) and analyzed by an analytical result analyzing unit (371). The analytical result is stored in a memory (369) while associated with position information in a driver control unit (367) and information on laser beam irradiation condition in a laser control unit (373), and the analytical result is imaged by an imaging unit (375). The imaged analytical result is displayed on a display (377).

10 Claims, 87 Drawing Sheets

| W | 10 ~ 2000 μm |
| D | 50nm ~ 3 μm |
| φ | 10 ~ 100nm |
| d | 10nm ~ 3 μm |
| p | 1nm ~ 10 μm |

U.S. PATENT DOCUMENTS

| | | | |
|---|---|---|---|
| 5,637,458 A * | 6/1997 | Frankel et al. | 435/6 |
| 6,111,251 A * | 8/2000 | Hillenkamp | 250/288 |
| 6,387,234 B1 * | 5/2002 | Yeung et al. | 204/451 |
| 6,770,439 B2 * | 8/2004 | Singh et al. | 435/6 |
| 6,783,672 B2 * | 8/2004 | Tubbs et al. | 210/198.2 |
| 6,812,455 B2 * | 11/2004 | Hillenkamp et al. | 250/288 |

FOREIGN PATENT DOCUMENTS

| | | |
|---|---|---|
| JP | 04-040367 | 2/1992 |
| JP | 05-164741 | 6/1993 |
| JP | 2572397 | 10/1996 |
| JP | 11-064283 | 3/1999 |
| JP | 2001-264297 | 9/2001 |
| JP | 2001-281222 | 10/2001 |
| JP | 2002-311007 | 10/2002 |
| JP | 2002-365177 | 12/2002 |
| JP | 2003-503715 | 1/2003 |
| WO | WO 00/15321 | 3/2000 |
| WO | WO 01/02093 A2 | 1/2001 |
| WO | WO 02/068952 A1 | 9/2002 |
| WO | WO 03/044519 A1 | 5/2003 |

* cited by examiner

| W | 10 ~ 2000 μm |
| --- | --- |
| D | 50nm ~ 3 μm |
| φ | 10 ~ 100nm |
| d | 10nm ~ 3 μm |
| p | 1nm ~ 10 μm |

THIN FILM PORTION

Fig.12
(e)
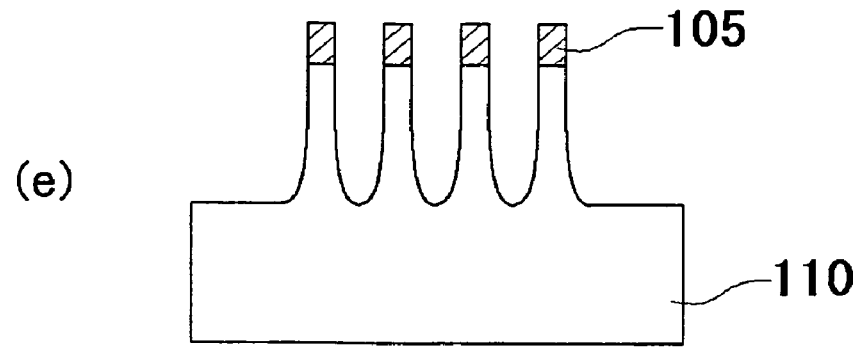
(f)
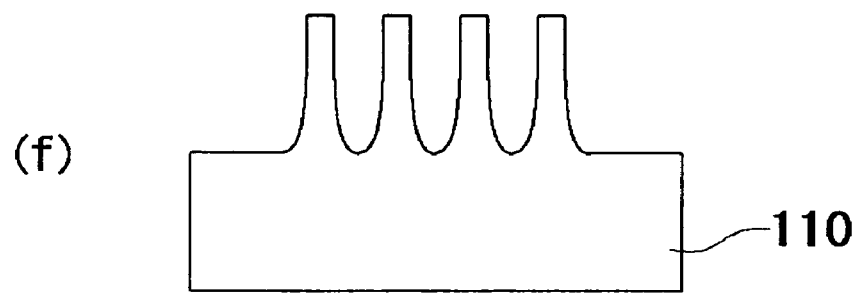
(g)
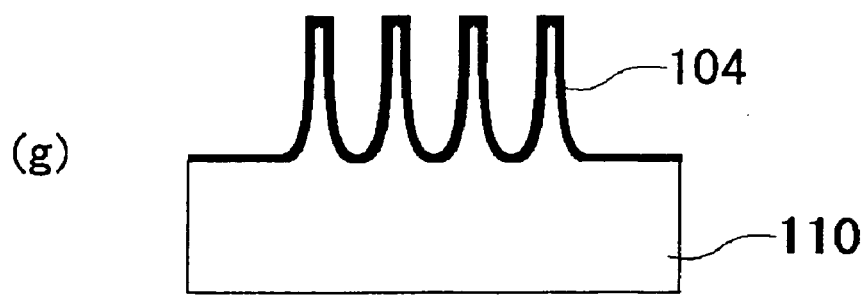

Fig.13
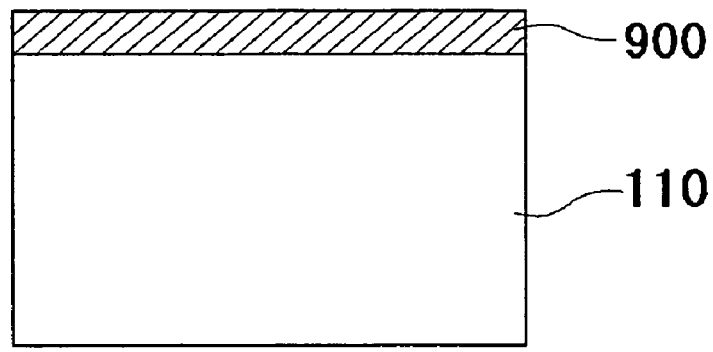
(a)
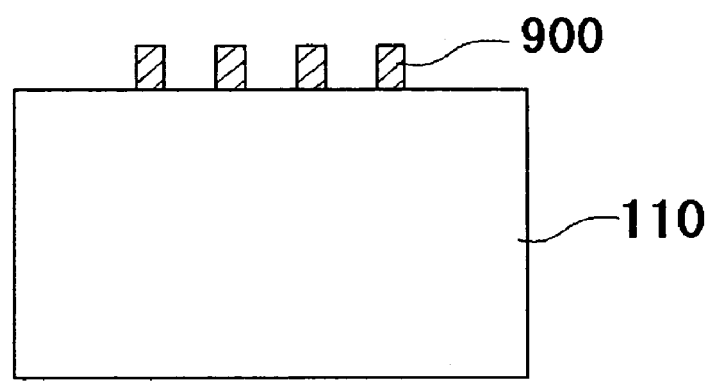
(b)
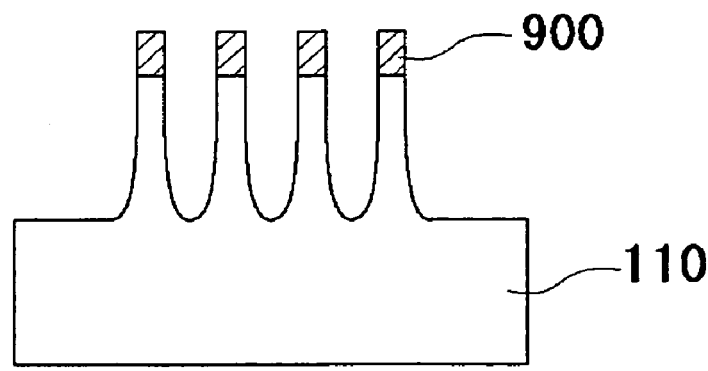
(c)

Fig.20
(a)
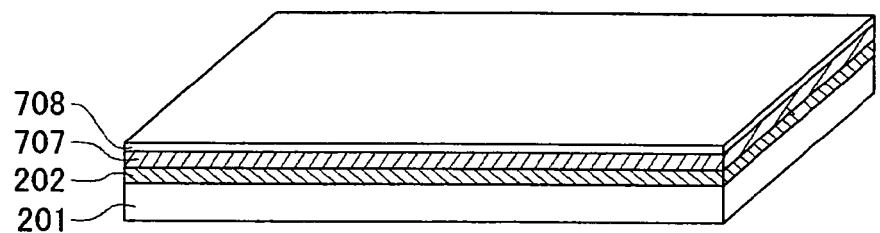
(b)
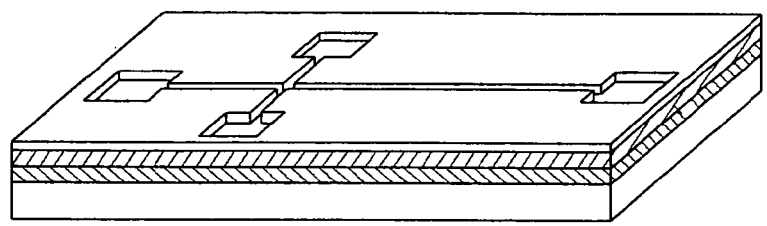
(c)
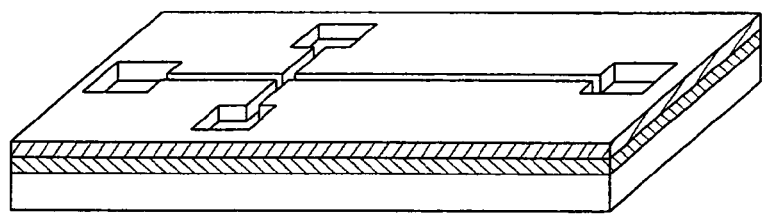
(d)
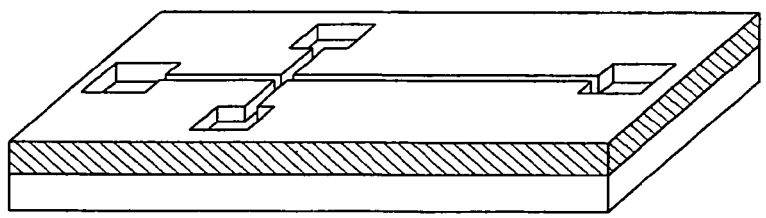

Fig.26
(a)
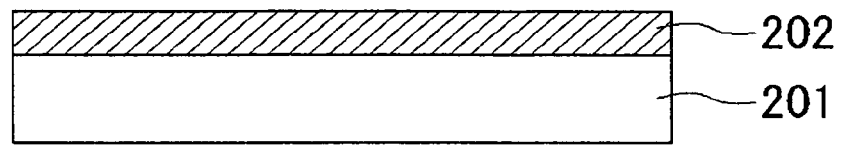
(b)
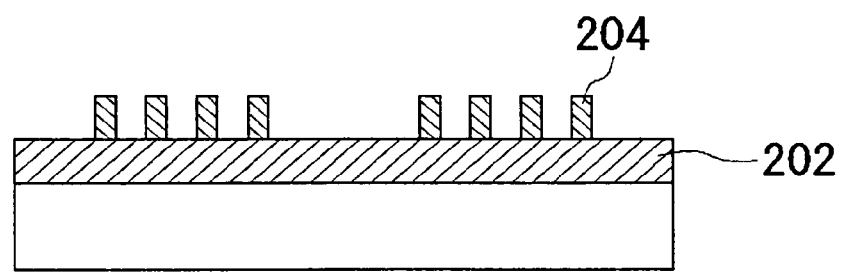
(c)
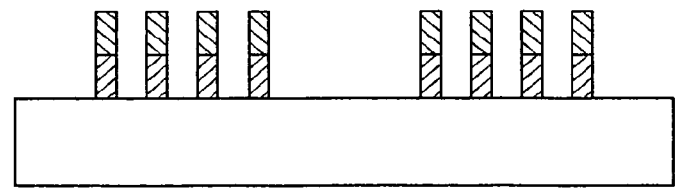

Fig.27
(d)
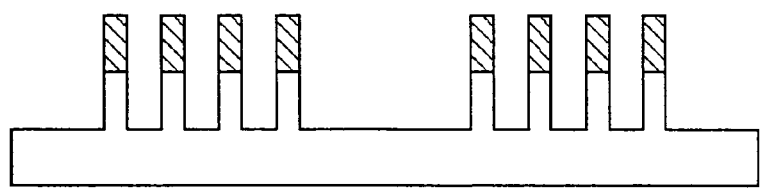
(e)
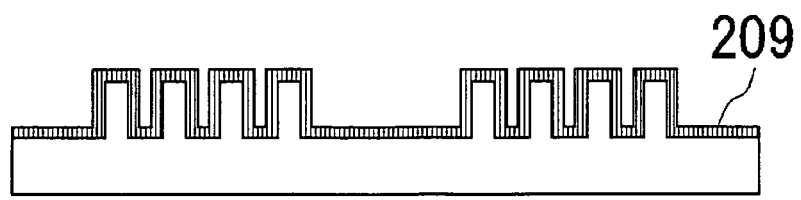

Fig.28
(a)
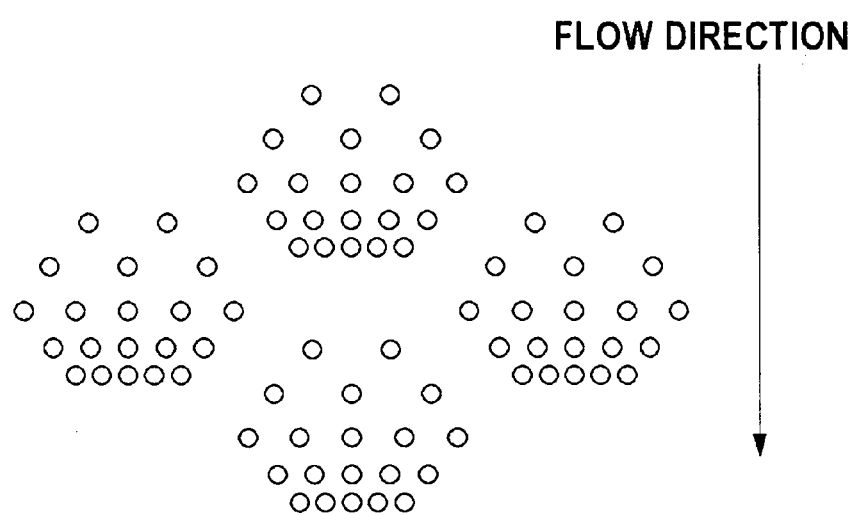
FLOW DIRECTION
(b)
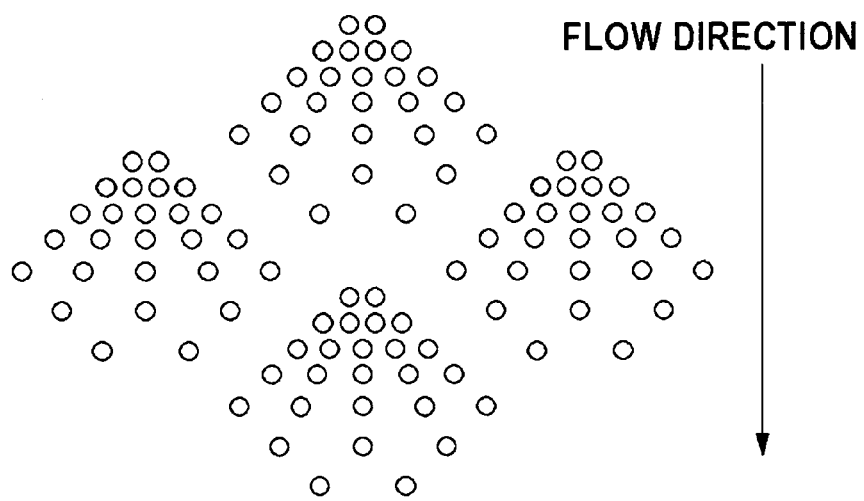
FLOW DIRECTION

FLOW DIRECTION

Fig.33
(a)
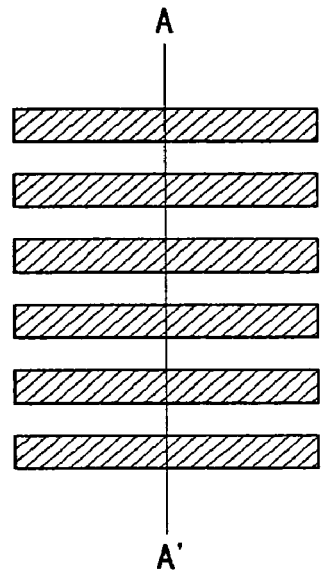
(b)
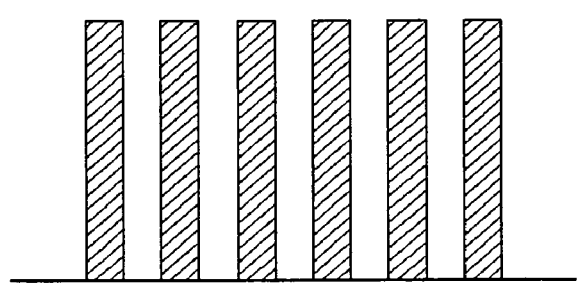
(c)
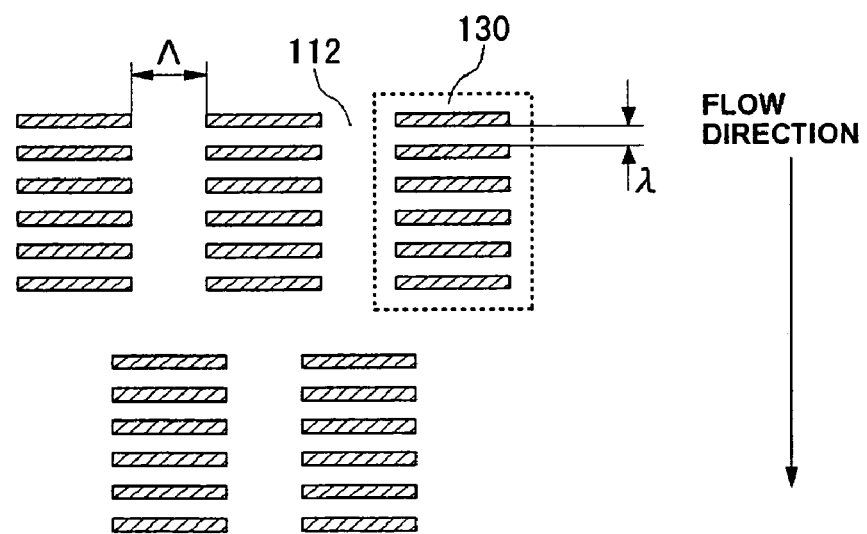
FLOW DIRECTION

Fig.34
(a)
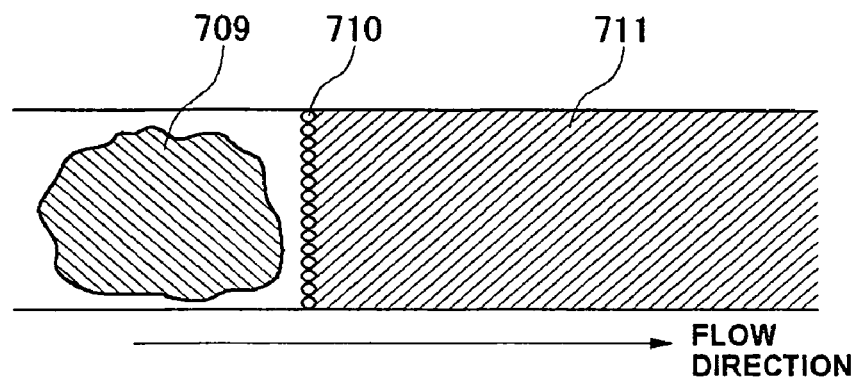
(b)
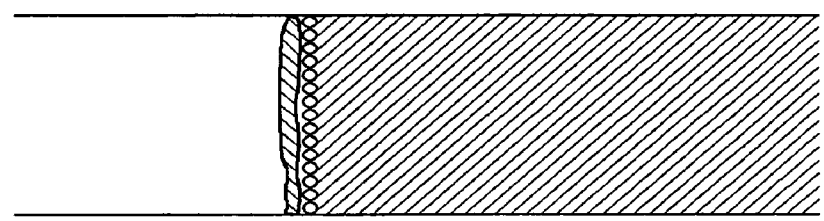
(c)
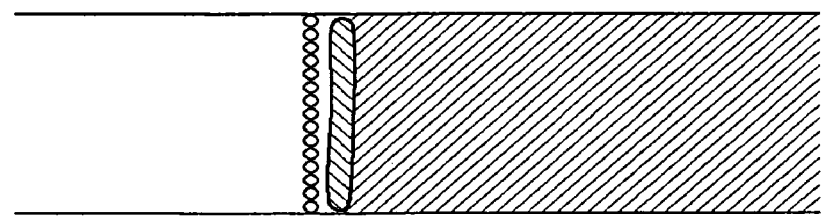
(d)
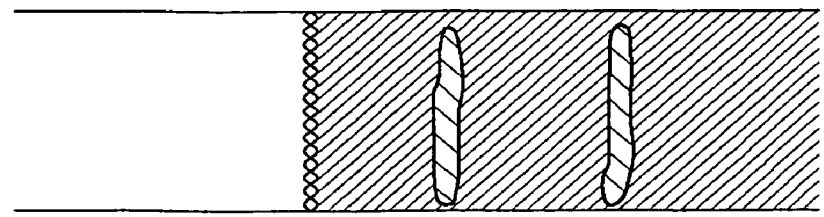

Fig.41
CHANNEL STRUCTURE (EVENLY ARRANGED CASE)
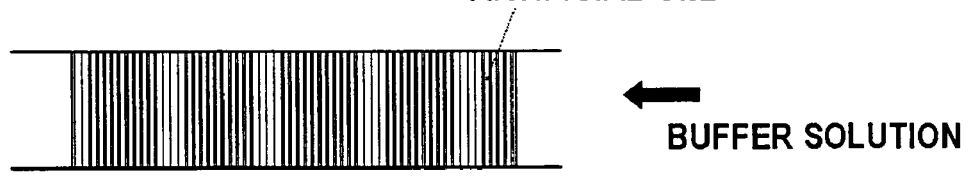
ARTIFICIAL GEL
← BUFFER SOLUTION
WATER FLOW IN CHANNEL
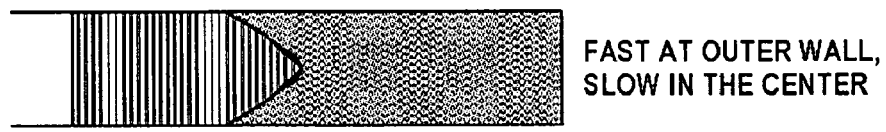
FAST AT OUTER WALL, SLOW IN THE CENTER
BAND STATUS
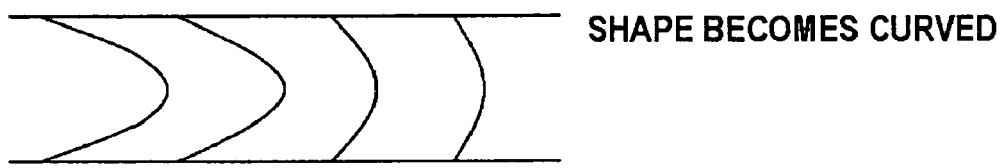
SHAPE BECOMES CURVED

HOLE

| | IN THE CASE OF SMALL-SIZE PARTICLE | IN THE CASE OF LARGE-SIZE PARTICLE |
|---|---|---|
| W | 10 ~ 2000 μm | |
| D | 100nm OR LESS | 3 μm OR LESS |
| φ | 50nm OR LESS | 300nm OR LESS |
| d | 100nm OR LESS | 3 μm OR LESS |
| p | 50nm OR LESS | 300nm OR LESS |

Fig.53
(a)
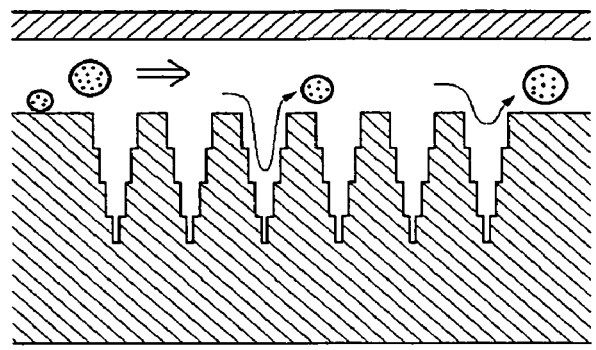
(b)
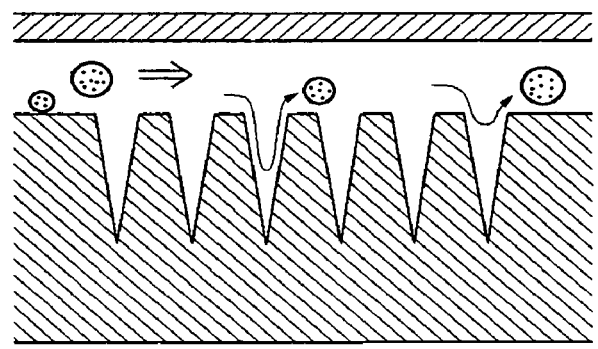
(c)
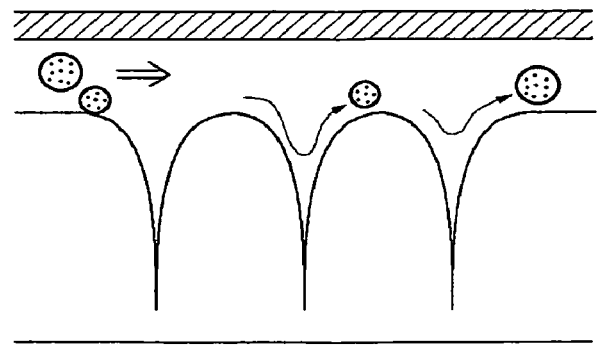

Fig.54
(a)
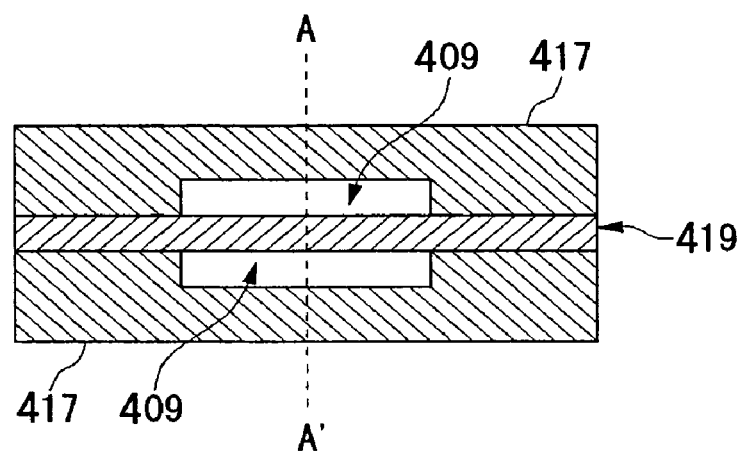
(b)
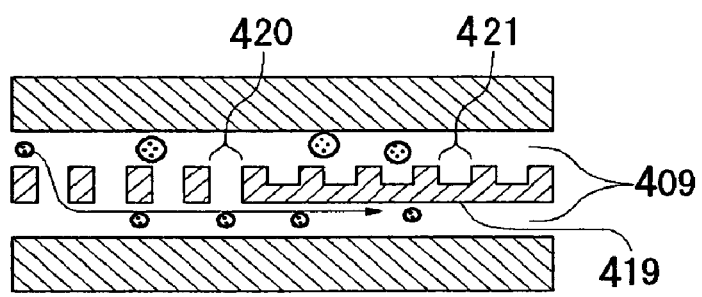
(c)
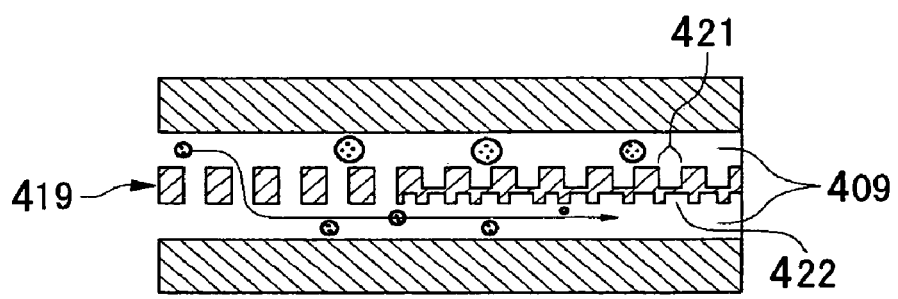

Fig.55
(a)
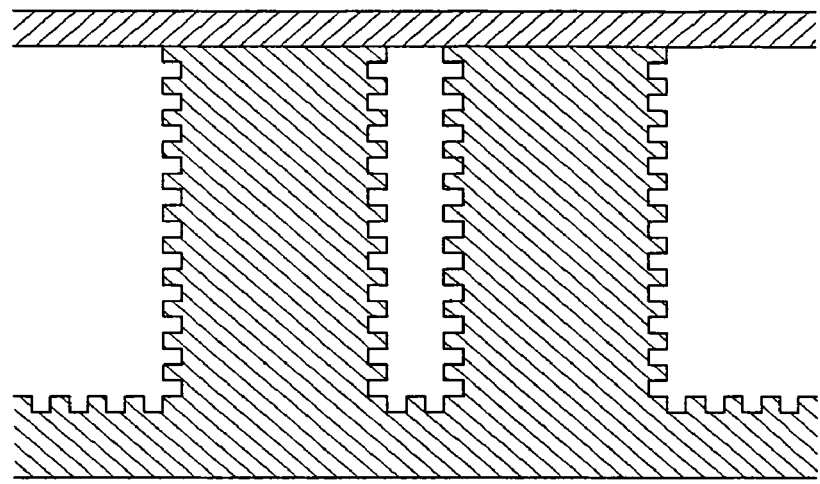
(b)
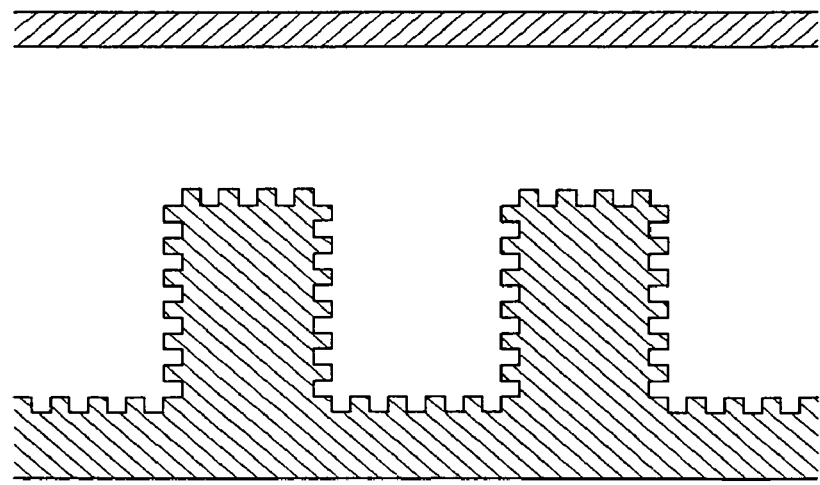

Fig.61
(a)
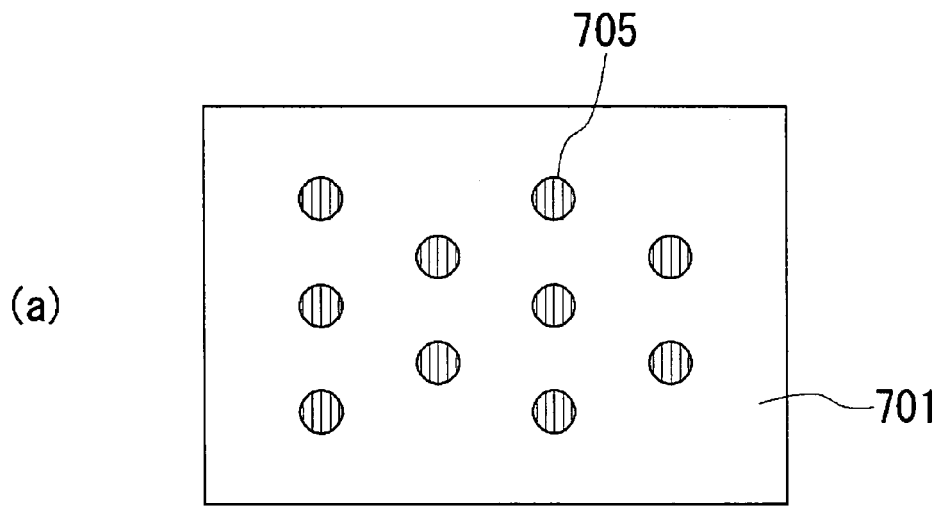
(b)
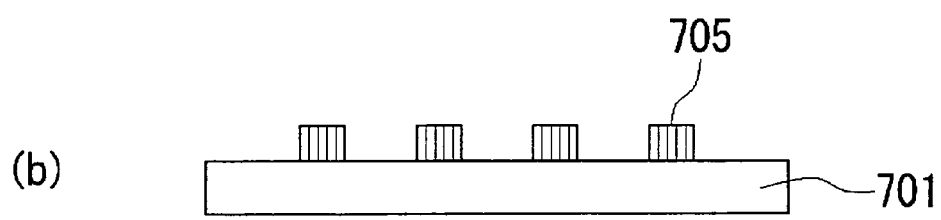

Fig.64
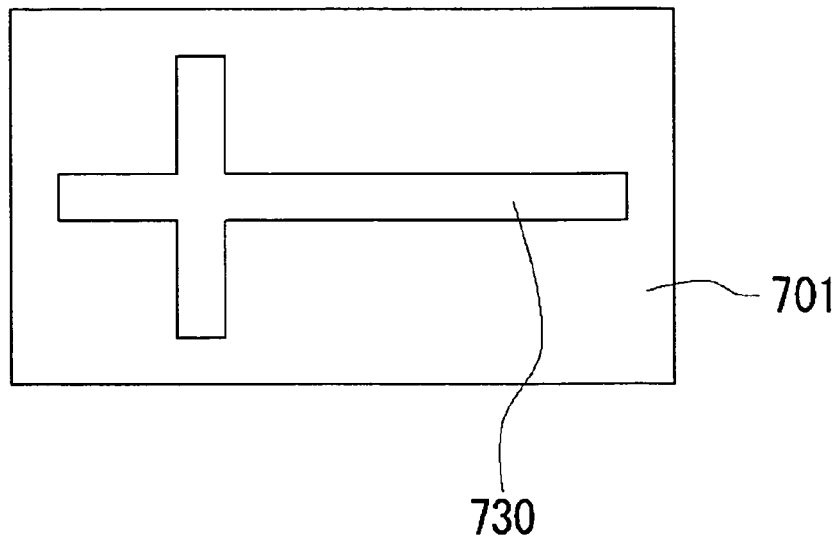
(a)
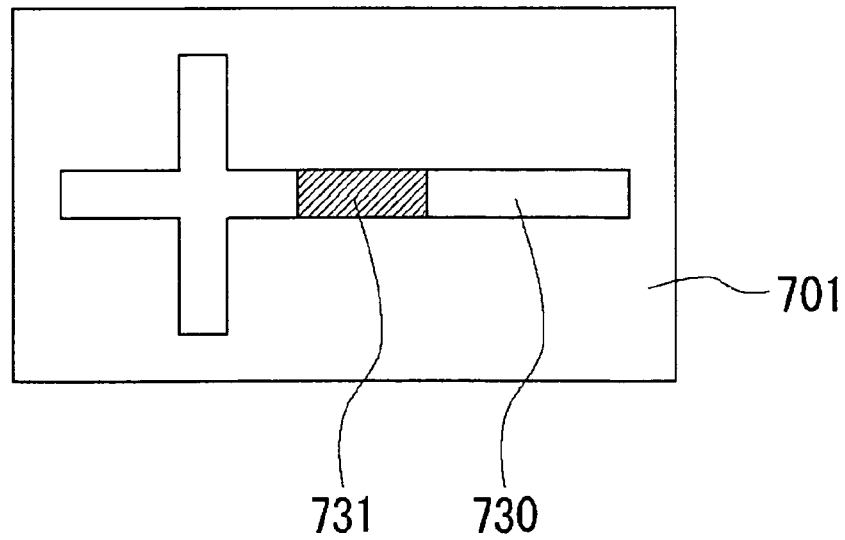
(b)

Fig.68
(a) 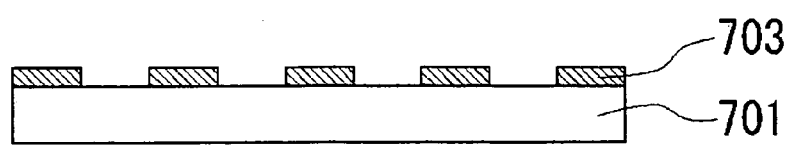
(b) 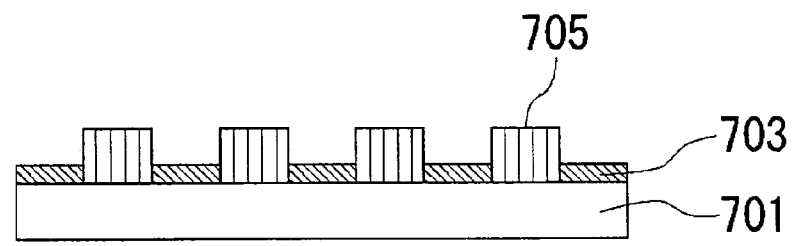

Fig.70
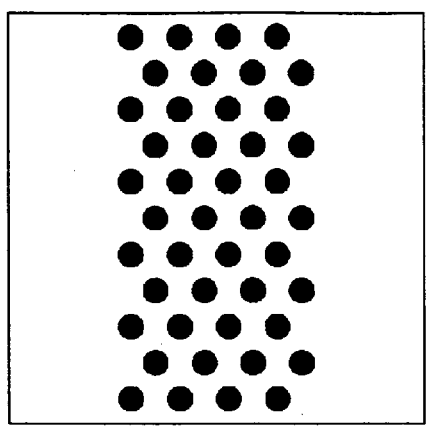
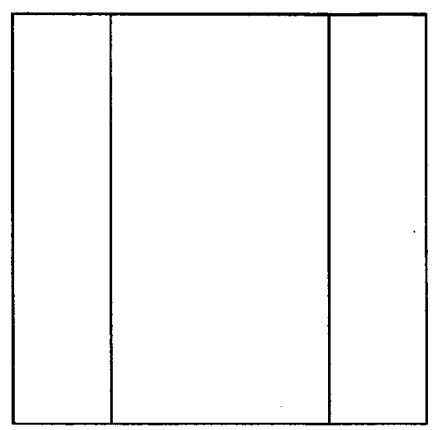
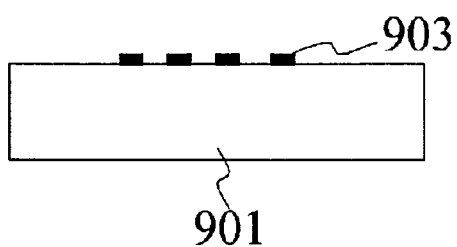
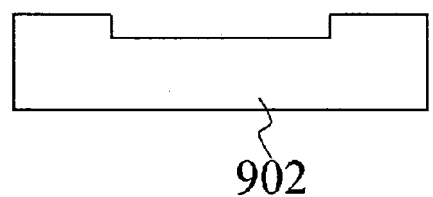
(a)　　　　　　　　(b)

Fig.74
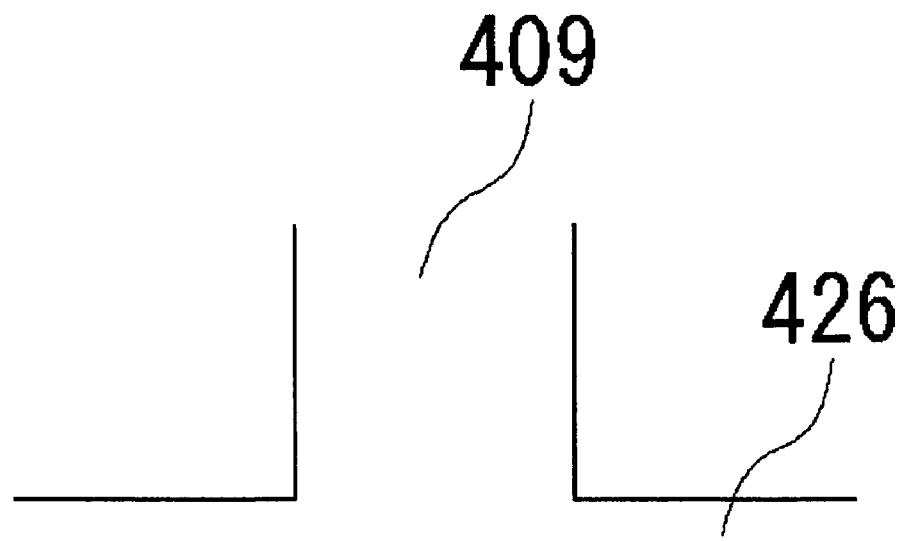
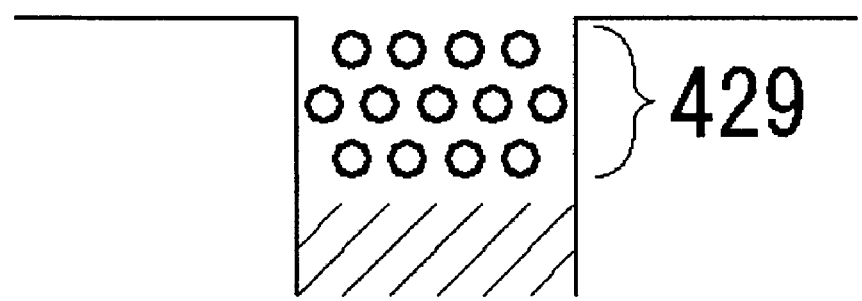

Fig.75
(a)
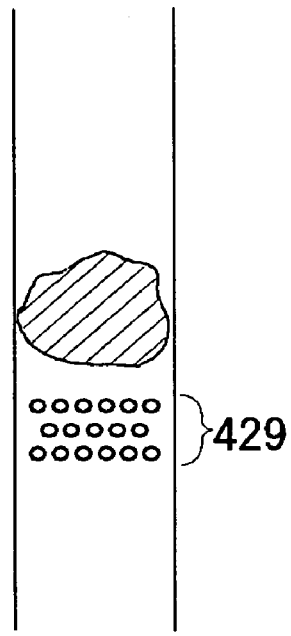
(b)
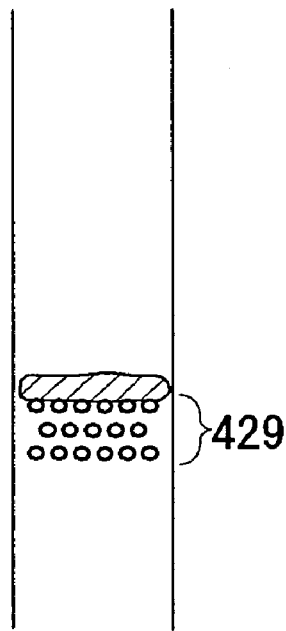

Fig.76
(a)
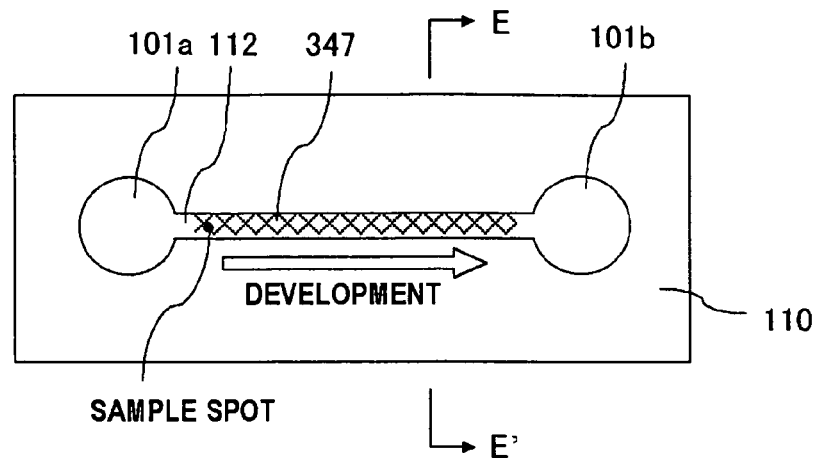
(b)
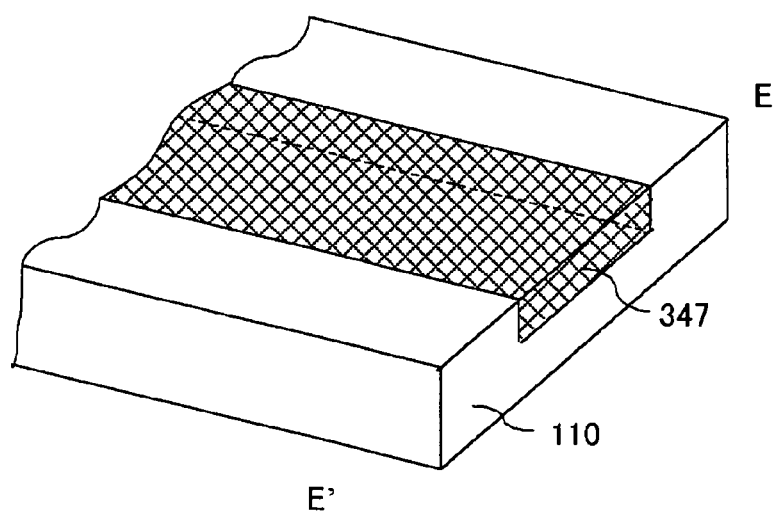

Fig.82
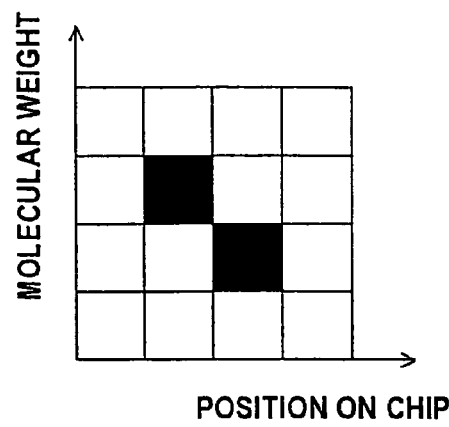
(a)
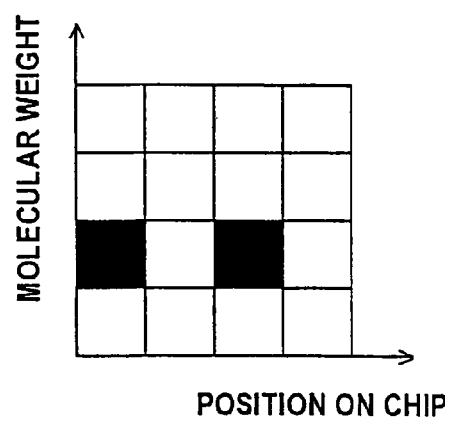
(b)

Fig.84
(a)
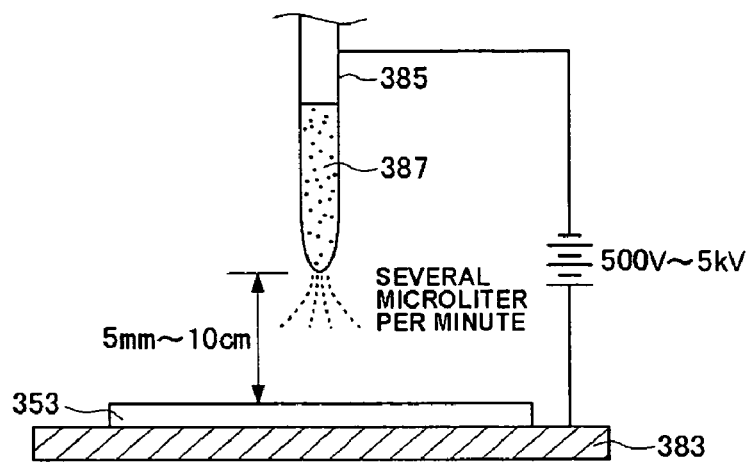
(b)
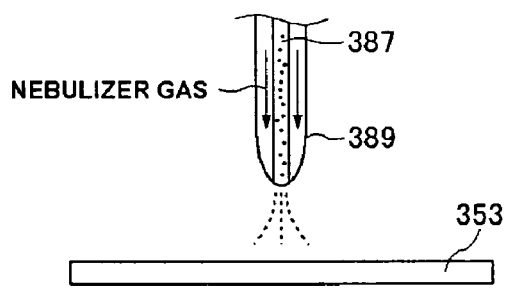
(c)
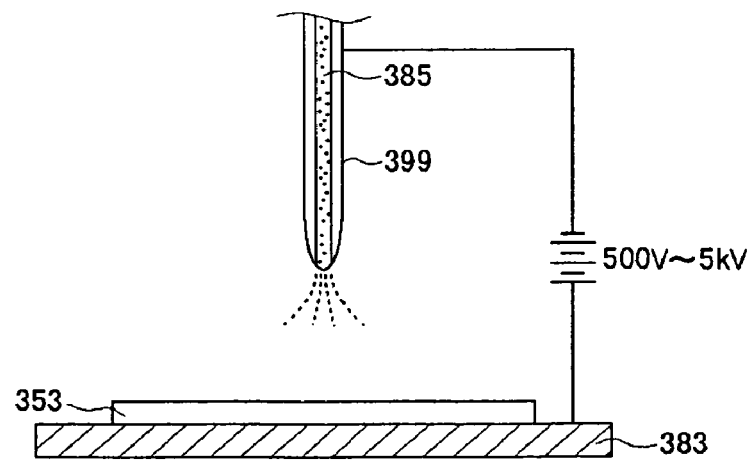

Fig.85
(a)
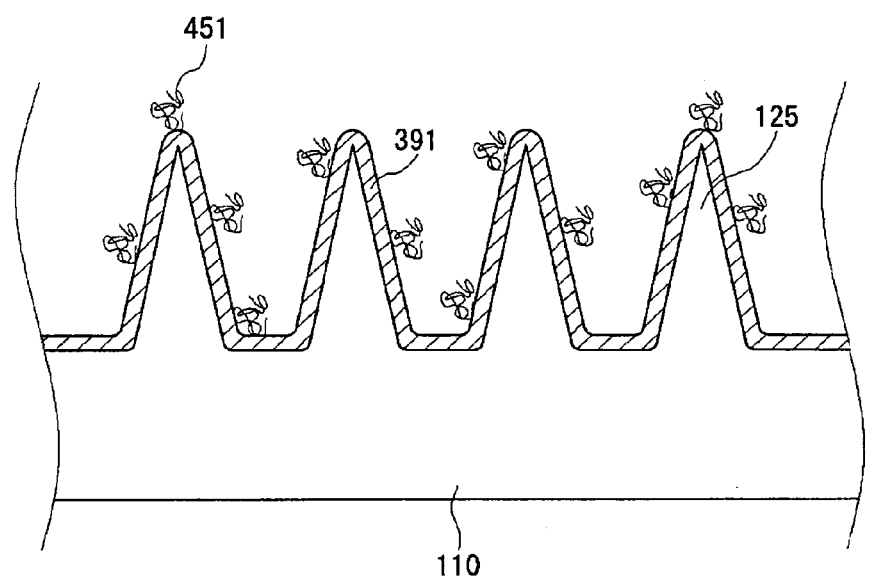
(b)
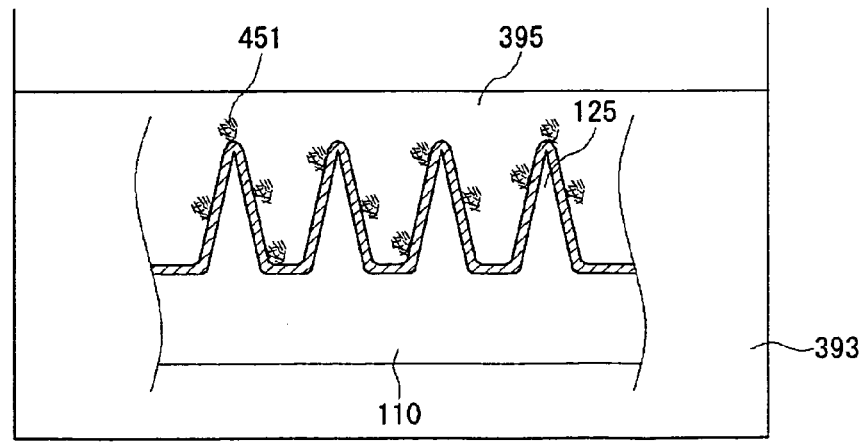

Fig.86
(a)
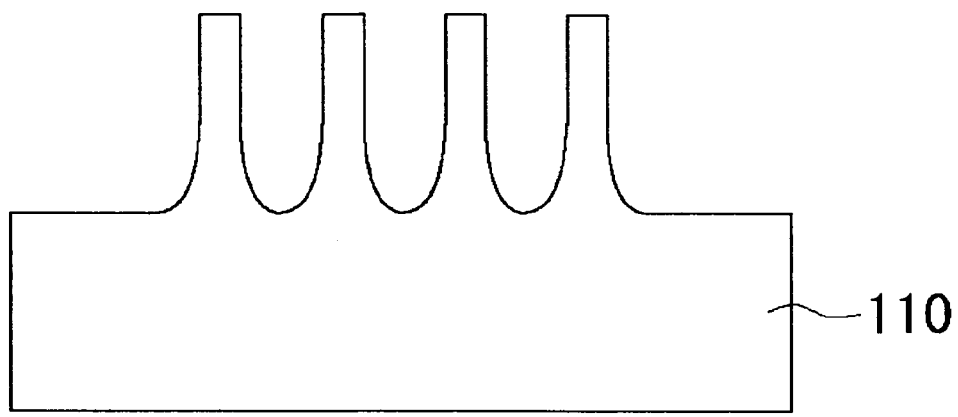
(b)
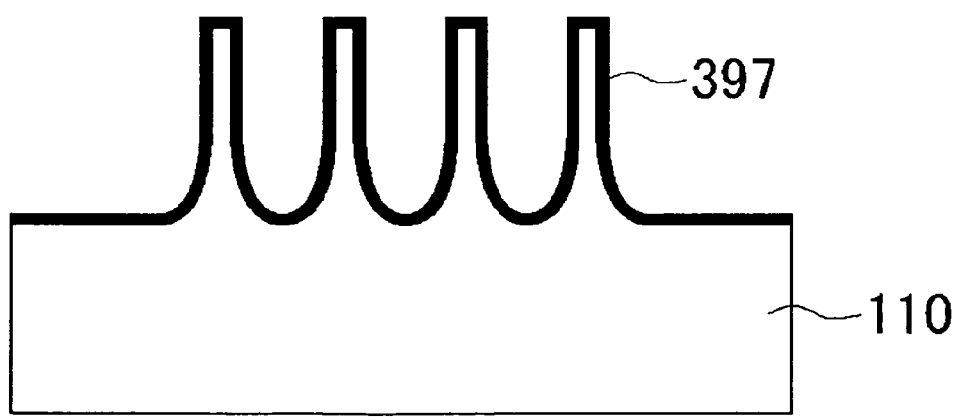

Fig.87
(a)
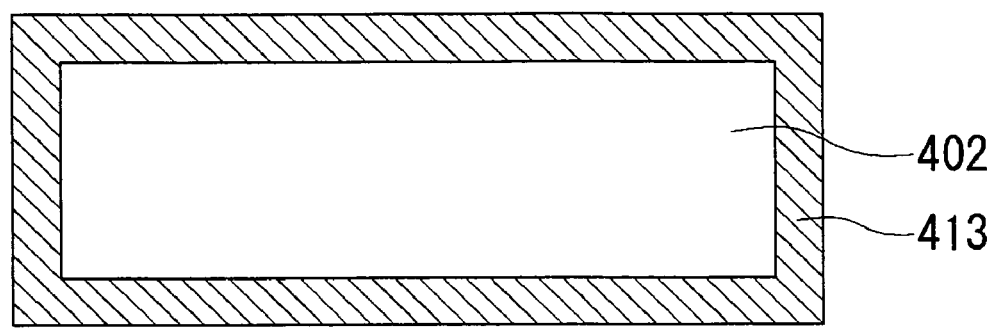
(b)
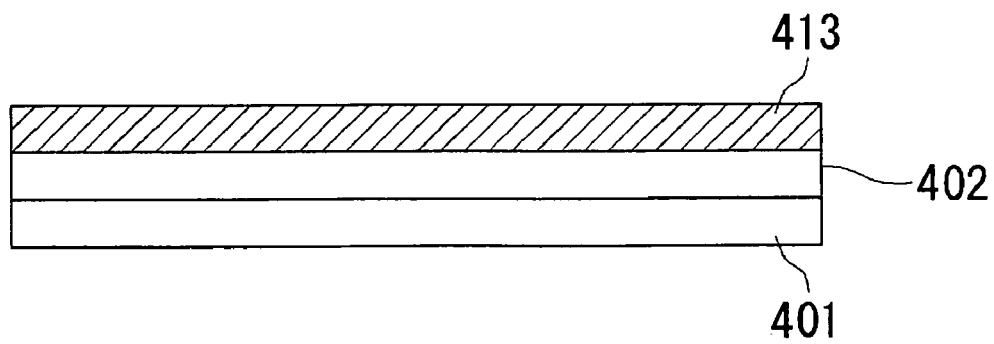

MASS SPECTROMETRIC SYSTEM AND MASS SPECTROMETRY

TECHNICAL FIELD

The present invention relates to a mass spectrometry system and a method for analysis.

BACKGROUND ART

In the analysis of biological samples such as cells and biological materials such as proteins and nucleic acids, an operation for previously separating and purifying the sample and an operation for separating the sample according to sizes or electric charge are performed prior to the analysis. For example, in proteomics analysis, usually mass spectrometric analysis is used for the analysis of a separated component. When the component contained in the sample provided for the mass spectrometric analysis is a biological component such as a protein, a nucleic acid, and a polysaccharide, conventionally it is necessary that the target component is previously isolated from the biological sample. For example, when the analysis of the sample containing the plural components is performed, the sample has been purified, the separation has been performed in each component by a two-dimensional electrophoresis, each component has been recovered from each separated spot, and the sample for mass spectrometric analysis has been prepared with the recovered component. Therefore, it is necessary that the separation process and the sample preparation process are separately performed, which complicates the operation.

There is studied a method in which the component separation in the sample and the mass spectrometric analysis are efficiently performed for the purpose of eliminating such the complicated operation (Patent Documents 1 and 2). Patent Documents 1 and 2 describe a mass spectrometry apparatus, in which a capillary tube for performing the electrophoresis and an ionizing unit for performing the mass spectrometric analysis are integrated to continuously perform the electrophoresis and the mass spectrometric analysis. However, in this kind of apparatus, it is necessary that the mass spectrometric analysis is performed point by point for the component recovered from the capillary tube. Therefore, there is still room for improvement from the viewpoint of analytical efficiency. Further, because a configuration of the apparatus becomes a large scale, there is also still room for improvement from the viewpoint of space saving.

Recently research and development of a microchip in which a function of separating or analyzing substances derived from a living organism is included on a chip is actively performed. Patent Document 3 describes the mass spectrometry in which the microchip is used. In the method described in Patent Document 3, a probe to which an adsorbent is coupled is provided in a bottom surface of a substrate, a specific component in the sample is adsorbed by the adsorbent to separate the components by bringing the substrate into contact with the sample, and then the mass spectrometric analysis is performed in each probe.

However, in the method described in Patent Document 3, it is necessary that the absorbent corresponding to each component in the sample is selected to prepare a probe substrate in which the selected adsorbent is immobilized. Then, the sample is spotted on the probe, and it is necessary to wash and remove the unnecessary component. Then, the adsorbed component is sequentially ionized in each probe to perform the mass spectrometric analysis. Therefore, the separation and the analysis of the sample are not continuous, and the operation is relatively complicated.

Patent Document 1: Japanese Patent Application Laid-Open No. H5-164741

Patent Document 2: Specification of Japanese Patent No. 2572397

Patent Document 3: Japanese Patent Application Laid-Open No. 2001-281222

DISCLOSURE OF THE INVENTION

In view of the foregoing, the present invention provides a technology which efficiently performs the sample separation and the mass spectrometric analysis with high accuracy.

According to the invention, there is provided a mass spectrometry system comprising a microchip which has a channel through which a sample passing, and a sample separation area being provided in the channel; light irradiation unit irradiating with a laser beam while moving a light irradiation position along the sample separation area; and an analytical unit analyzing a fragment of the sample to obtain mass spectrometric data, the fragment of the sample being generated by a light irradiation.

The mass spectrometry system is configured to directly ionize the sample, separated in the sample separation area, to analyze the fragment of the sample. Therefore, according to the mass spectrometry system of the invention, a two-dimensional profile can be obtained by two parameters of a position A on the microchip and a molecular weight B. FIGS. 82(*a*) and 82(*b*) show examples of the two-dimensional profile. In the examples, as described later, the mass spectrometric analysis is performed by the laser beam irradiation while the light irradiation position is moved along the sample separation area, and the two-dimensional profile is obtained based on the position A on the microchip and the molecular weight B.

The use of the profile enables to obtain various kinds of information without performing the identification of the component by the mass spectrometric analysis. For example, in the case where a blood of a subject is analyzed to conduct screening of a certain disease, the profile of a healthy person and the profile of an affected person are set to be reference datas to be compared with the two-dimensional profile obtained from the blood of the subject, which allows the screening to be conducted without analyzing the component.

In the mass spectrometry system of the invention, the sample is separated in the sample separation area according to the property of the sample. The separated sample is irradiated with the laser beam to perform the mass spectrometric analysis while the light irradiation position is moved along the sample separation area. Therefore, the separated sample can be ionized to perform the mass spectrometric analysis without moving the sample from the position where the sample is separated. Since a process of extracting the separated sample from the position where the sample is separated is not required, loss of the sample is not generated. Therefore, even in the case of a small amount of sample, the separation can securely be performed and the mass spectrometric analysis can be performed with high accuracy. In the invention, "moving a light irradiation position along the sample separation area" should mean that a laser beam position relative to the sample separation area is moved, and should include change in laser beam irradiation direction or irradiation angle.

Thus, according to mass spectrometry system of the invention, since the sample is ionized to perform the mass spectrometric analysis by directly irradiating the sample with the laser beam along the sample separation area, a mass spectrometric analysis spectrum of each component separated in the sample separation area can efficiently be obtained.

In the mass spectrometry system of the invention, the analytical unit may include a data memory unit, in which the light irradiation position and the mass spectrometric data corresponding to the light irradiation position are stored while associated with each other.

Thus, the analysis can efficiently be performed to obtain the spectrum property of each component in full detail by combining the separation position of each component and the mass spectrometric analysis spectrum of the component. Therefore, the identification of the component in the sample and the like can rapidly performed with high accuracy based on the obtained information.

In the mass spectrometry system of the invention, the sample separation area may be configured to separate the sample according to a molecular weight, an isopotential point, or a surface hydrophobic property of the sample, and the light irradiation unit may irradiate with the laser beam while moving the light irradiation position along the sample separated in the sample separation area. Thus, the sample containing the plural components can securely be separated to perform the mass spectrometric analysis according to the property of the component. Further, the identification of the component and the like can rapidly be performed because the analysis can efficiently be performed by combining the property of the component and the mass spectrometric analysis spectrum of each component.

In the above mass spectrometry system, an important technical issue is to configure to separate the sample in the sample separation area in the mode suitable for the mass spectrometric analysis. For example, when the sample separation area is irradiated with the laser beam, it is desirable that constituent of the sample separation area is not ionized. Also, on irradiating with the laser beam, it is desirable that the mass spectrometry apparatus is configured to rapidly ionize the sample to smoothly move the fragment into an mass spectrometer. Seen from these viewpoints, the conventional sample separation area in which the channel is filled with polymer gel has the problems that a part of the polymer gel is ionized by the laser irradiation and the fragment derived from the sample is not efficiently emitted. Therefore, the conventional sample separation area is not always suitable for the use of the sample separation area of the present invention. That is, in the invention, it is important that the sample separation area is designed from the viewpoint different from the configuration used in the conventional separation apparatus. The adoption of such sample separation area of the invention enables to accurately obtain multilateral data including the two parameters of the on-microchip position A associated with the sample separation and the molecular weight B associated with the mass spectrometric analysis, which allows a novel analysis to be realized. The configuration of the sample separation area suitable for the mass spectrometric analysis by a principle of the invention will be described below.

In the mass spectrometry system of the invention, the channel may be provided on a surface of a substrate and the sample separation area may have plural columnar bodies. Thus, the interval between the adjacent columnar bodies acts as a sieve. The sample separation is performed by such method in the invention, the various minute size substances such as the nucleic acid and the protein which are hardly separated by the conventional art can be separated and fractionated. In the invention, the plural columnar bodies should mean the number of columnar bodies in which separation function can be exerted.

The separated sample is irradiated with the laser beam to efficiently perform the ionization by forming the sample separation area in the columnar bodies. At this point, when compared with the conventional separation methods such as the electrophoresis in which the filler such as gel and beads is used, the liquid sample is smoothly vaporized during the laser beam irradiation while the liquid sample is held in the separation channel to suppress drying during the separation. In the case of the use of the filler, sometimes measurement accuracy is remarkably decreased due to the ionization of the filler. According to the configuration in which the columnar bodies of the invention are used, such the problem can be solved and the analysis can be performed with high accuracy. The fragment derived from the sample is efficiently emitted from the sample separation area, which achieves the high-accuracy analysis. Further, according to the configuration, for example the molecule having the relatively larger size can be measured in the protein or the like by appropriately designing the interval and the arrangement of the columnar bodies.

In the mass spectrometry system of the invention, the sample separation area may include plural columnar body arrangement portions in which the plural columnar bodies are arranged and a path may be provided between the adjacent columnar body arrangement portions, the sample passing through the path. Accordingly, as the size of the substance to be separated becomes smaller, the substance is trapped easier by the columnar body in the sample separation area to pass through a long path. That is, the smaller-size substance is separated so as to be discharged subsequent to the larger-size substance. Since the larger-size substance passes relatively smoothly through the separation area, a clogging problem is reduced and throughput is largely improved. Therefore, it can be applied to the separation for the nucleic acid, the protein, and the like, which enables the secure performance of the mass spectrometric analysis of the sample including them. In the case of the adoption of the above configuration, each component in the sample is preferably separated in the sample separation area, even if measurement subject is the sample in which the larger component and the smaller component are mixed. As a result, the analytical data can efficiently be obtained by one-time analysis.

In the mass spectrometry system of the invention, a width of the path may be larger than an average interval between the columnar bodies in the columnar body arrangement portion. Accordingly, while the larger-size substance passes smoothly through the path in the sample separation area, the smaller-size substance passes through the columnar body arrangement portion and reaches the sample separation area through the long path according to the size of the substance.

In the mass spectrometry system of the invention, the plural columnar body arrangement portions may be combined and arranged such that a plane arrangement is to be a substantial rhombus, and the columnar bodies may be arranged such that the plane arrangement of each of the columnar body arrangement portions is to be a substantial rhombus. Therefore, separation ability can further be improved.

In the mass spectrometry system of the invention, density of the plural columnar bodies may be gradually increased toward the proceeding direction of the sample in the channel. Thus, because a residence time of the molecule trapped by the columnar body arrangement portion becomes longer in the columnar body arrangement portion, a difference in holding time becomes prominent between the molecule trapped by the columnar body arrangement portion and the molecule not trapped by the columnar body arrangement portion, which allows the separation ability to be improved.

On the contrary, in a mass spectrometry system of the invention, the density of the plural columnar bodies may be gradually decreased toward a proceeding direction of the sample in the channel. In this case, the clogging is suppressed in the columnar body arrangement portion, which allows the throughput to be improved.

In the mass spectrometry system of the invention, the sample separation area and an adjustment area may be alternately formed with respect to the proceeding direction of the sample in the channel, the columnar bodies being formed less densely in the adjustment area than in the sample separation area. Accordingly, since the shape of each separated band can further linearly be formed, the band can be condensed and the detection can be performed with high accuracy when the mass spectrometric analysis of each band is performed.

In the mass spectrometry system of the invention, a metal layer may be provided on the surface of the columnar body. Also, in the mass spectrometry system of the invention, the columnar body may be made of metal. Because a surface plasmon wave is generated on the surface of the columnar body by forming at least the surface of the columnar body with metal, ionization efficiency of the sample is improved. A strong electric field is also generated on the surface of the columnar body, which allows extraction efficiency of the ionized sample to be improved. In this case, it is preferable that a bottom portion is wider than a top portion in a sectional shape of the columnar body. Thus, the electric field can be concentrated on the top portion of the columnar body to further improve the extraction efficiency of the ionized sample.

In the mass spectrometry system of the invention, the laser beam may be an infrared laser beam or an ultraviolet laser beam. Thus, biopolymers having the relatively large molecular size such as the protein and the nucleic acid can further securely be ionized.

In the mass spectrometry system of the invention, the sample separation area may be configured to have plural cocaves. Thus, as the size of the substance to be separated becomes smaller, the substance is trapped easier by the cocave in the sample separation area to pass through the long path. That is, the smaller-size substance is separated so as to be discharged subsequent to the larger-size substance. Since the larger-size substance passes relatively smoothly through the separation area, the clogging problem is reduced and the throughput is largely improved. Particularly, in the separation of the nucleic acid, the protein, and the like, because an inertia radius of the molecule covers a wide range, the gigantic-size substance is easy to generate the clogging. Once the gigantic-size substance generates the clogging, even if washing is performed, it is difficult to release the gigantic-size substance. According to the invention, because the problem is solved, the invention can preferably be applied to the separation of the nucleic acid, the protein, and the like.

In the invention, the plural concaves should mean the number of concaves in which the separation function can be exerted. In the invention, an opening maximum diameter of the concave may be set at an extremely narrow value. In this case, various substances not even predicted can be separated and fractionated. For example, in separating the nucleic acid or the protein, it is desirable that the concave has a fine-opening having the dimension of the order of hundreds nanometer or less.

The shape of the opening is not particularly limited and for example, a circular shape, an elliptic shape, a polygonal shape and the like. In the invention, the opening maximum diameter of the concave should mean a length of the longest line among arbitrary lines which are formed by connecting one point of the opening and one of the other points. In the invention, a depth direction of the concave is not need to be similar to a direction of gravity. For example, it is also possible that the concave is provided in the direction parallel to the wall surface of the channel.

The mass spectrometry system of the invention may be configured to include a projecting portion in the sample separation area, the plural concaves being provided in the projecting portion. Accordingly, because an area of the surface having the concaves can be increased, the separation ability is improved.

In the mass spectrometry system of the invention, the concave may be formed by an anodic oxidation process. In the anodic oxidation process, the concave having the desired dimension and the sample separation area having the desired interval between the concaves can be realized by the smaller number of processes.

In the mass spectrometry system of the invention, the surface of an inner wall of the channel may be hydrophilized. Also, in the mass spectrometry system of the invention, the surface of the inner wall of the channel may be water repellent treated. Accordingly, because nonspecific adsorption of the sample component to the inner wall of the channel can be suppressed, the sample loss or the decrease in separation accuracy can be suppressed to exert the good separation ability. Further, since the sample loss is suppressed, the accuracy of mass spectrometric analysis can be improved.

In the mass spectrometry system of the invention, the inner wall of the channel is hydrophilized by a hydrophilic material adhered to the surface of the inner wall of the channel.

Also, in the mass spectrometry system of the invention, the inner wall of the channel may be hydrophilized by forming a silicon thermal oxide film on a surface of the channel. The formation of the thermal oxide film suppresses the nonspecific adsorption of the sample to the channel wall. Further, during the laser beam irradiation, the ionization of the hydrophilic substance adhering to the channel surface of the sample separation is suppressed. Therefore, a background of the mass spectrometric analysis can be decreased to further improve the measurement accuracy.

In the mass spectrometry system of the invention, the surface of the sample separation area may have plural first areas and a second area, the first areas being arranged while separated from one another, the second area occupying the surface of the sample separation area except for the first areas, and one of the first area and the second area may be formed in a hydrophobic area and the other may be formed in a hydrophilic area. Specifically, either (i) The configuration wherein the first area is the hydrophobic area and the second area is the hydrophilic area, or
(ii) The configuration wherein the first area is the hydrophilic area and the second area is the hydrophobic area, can be adopted. In the invention, the hydrophilic area should mean the area in which the hydrophilicity is higher than the hydrophobic area. For example, a degree of the hydrophilicity can be grasped by measurement of a water contact angle.

Then, the principle of the sample separation in the invention will be described by the case of (i) as an example. In this case, the sample to be separated is introduced into the channel while dissolved or dispersed in a solvent having the relatively high hydrophilicity. The solvent having the relatively high hydrophilicity keeps from the surface of the hydrophobic area (first area) and is distributed only in the hydrophilic area (second area) in the sample separation area. Therefore, a gap portion of the hydrophobic area becomes a path through which the sample to be separated passes. As a result, a time required to pass through the sample separation area is determined by a relationship between the size of the sample and the interval between the hydrophobic areas, which allows the sample separation to be performed according to the size.

In the invention, besides the separation according to the size, the separation according to sample polarity is also performed. That is, plural kinds of samples whose degrees of hydrophilicity/hydrophobicity differ from one another can be separated. In the example of (i), the sample having high hydrophobicity is easily trapped by the hydrophobic area and a discharge time becomes relatively longer. On the other hand, the sample having high hydrophilicity is hardly trapped by the hydrophobic area and the discharge time becomes relatively shorter. Thus, the invention can perform the separation not only in the sample size but in the polarity, so that the multi-component system separation which is conventionally difficult to perform can be realized.

Unlike the method in which the separation is performed by a structure of an obstacle, in the invention the sample separation area provided on the channel surface is formed as a separation unit. For example, in the conventional film separation, it is necessary to accurately control the dimensions of micro-holes in the film. However, it is not always easy to stably produce the film having the desired dimension and shape of the micro-hole. On the contrary, in the invention, the sample separation area can be formed by surface treatment of the channel, and the desired separation ability can be obtained by controlling the distance between the first areas. Therefore, the proper configuration can relatively easily be realized according to the purpose of the separation.

For example, in the mass spectrometry system of the invention, the sample separation area may be formed by providing a mask having an opening in at least the surface of the channel, depositing a compound having a hydrophilic group on the surface of the channel via the opening, and removing the mask, the hydrophilic area being arranged in the sample separation area. In this case, the interval between the hydrophobic areas can easily be adjusted by adjusting a mask opening width. That is, the interval between the hydrophobic areas is appropriately adjusted according to the purpose of the separation, and the configuration of the sample separation area can be formed according to the purpose of the separation. Particularly, in the separation of the protein or DNA, the separation of various substances from the gigantic-size substance to the substance having the size of the order of nanometer is required. Among others, in the conventional art, it is very difficult that the substance having the size of the order of nanometer is separated at short times with high resolution. In the invention, the separation size can be narrowed by narrowing the interval between the first areas. Because the interval between the first areas can easily be realized by utilizing fine processing technology, the separation of the substance having the size of the order of nanometer can preferably be realized. Further, in the mass spectrometry system of the invention, the sample separation area may be formed by providing a mask having an opening in at least a portion of the surface of the channel, depositing a compound having a hydrophobic group is via the opening on the surface of the channel, and removing the mask, the hydrophobic area being arranged in the sample separation area.

According to the above configuration, the separation can be performed at short times with the small amount of sample. Since the separation of the invention is performed by a surface property of the sample separation area, the accurate separation can be realized. Further, since the sample loss is little, the sufficiently high resolution can be realized with the small amount of sample and the excellent resolution ca be realized.

In the invention, the separation is performed by the surface property of the channel through which the sample passes, the problems of the clogging and the like are decreased. Further, after the use, for example the washing can easily be performed by the method of running a washing solution to the surface of the sample separation area.

In the invention, the separation of various functions can be realized by the relationship between the sample size of the separation target included in a liquid and the distance between the adjacent first areas. When the sample size is larger than the distance, the sample separation area functions as a sample condensing apparatus. The sample separation area acts as a filter to stem the sample on the upstream side of the sample separation area. As a result, the sample is condensed in high concentration on the upstream side of the sample separation area. On the other hand, when the sample size is smaller than the distance, the sample separation area functions as sample fractionation, the sample is fractionated in the sample separation area according to the size, the degree of hydrophilicity and the like. As a result, the fractionated sample flows out to the downstream side of the sample separation area.

The mass spectrometry system of the invention may be configured to include the plural sample separation areas. Accordingly, in designing the sample separation area, a degree of freedom can further be increased to select the shape of the sample separation area optimizing the sample, which allows the separation ability to be further improved. For example, in the mass spectrometry system of the invention, the plural sample separation areas may be arranged in a stripe shape.

In the mass spectrometry system of the invention, the hydrophobic area may be formed by a film containing a compound having a hydrophobic group. The compound having the hydrophobic group may be a silane coupling agent having a hydrophobic group. Also, it may be a silicone compound.

In the mass spectrometry system of the invention, the hydrophobic area may be formed by bringing a polydimethylsiloxane block into contact with the surface of the channel which is hydrophilic. When the polydimethylsiloxane block is brought into contact with the surface of the channel, the contact portion can selectively be hydrophobilized. Therefore, the hydrophobic area can securely and simply be formed.

In the mass spectrometry system of the invention, the hydrophobic area may be formed by printing a liquid silicone compound onto the surface of the channel which is hydrophilic. For example, silicone oil can be used as the liquid silicone compound. According to the method, a pattern in which the hydrophobic surface and the hydrophilic surface are mixed can be formed through the simple process.

In the mass spectrometry system of the invention, the hydrophilic area may be formed by the film containing a compound having a hydrophilic group. The compound having the hydrophilic group may be a silane coupling agent having a hydrophilic group.

In the mass spectrometry system of the invention, the plural channels may be provided and a liquid sample introducing channel intersecting the channels may be provided. Accordingly, the sample can be introduced into the plural channels by introducing the sample into one point, so that the analytical efficiency can largely be improved. At this point, the plural columnar bodies may be arranged between the sample separation area and a part where the channel and the liquid sample introducing channel intersect each other. In this case, the molecules in the sample reach the separation area through the area in which the plural columnar bodies are arranged, which allows the size of the molecule flowing in the channel to be limited. Therefore, the mass spectrometric analysis can rapidly and correctly be realized for the molecule having the desired size.

The mass spectrometry system of the invention may further include a damming portion in which columnar bodies are arranged in a line. Accordingly, the diffused sample can be collected in a predetermined area adjacent to the damming portion. Since the sample can be collected in the predetermined area to narrow the band of the sample prior to the separation, the separation ability can be improved.

In the mass spectrometry system of the invention, the damming portion may be arranged adjacent to the sample separation area. Accordingly, since the band of the sample can be narrowed before the sample passes through the sample separation area, the separation ability is improved, which allows the high accuracy separation to be realized. Further, because the band width is also narrowed in the separated sample, the separated sample can be condensed. Therefore, the mass spectrometric analysis can further securely be measured.

In the mass spectrometry system of the invention, the sample separation area may be divided into plural areas through a slit. Both the single slit and the plural slits may be used. Accordingly, the band shape becomes linear in the detection unit, which allows the detection area to be widened to improve detection sensitivity.

The mass spectrometry system of the invention may further include external force applying unit applying external force to the sample to move the sample in the channel. Accordingly, the separation accuracy can appropriately be set according to the degree in which the external force is loaded, and the time required for the separation can be appropriately set according to the purpose. It is convenient that pressure and electric force are used as the external force. This is because the large-scale external force applying member is not required.

The sample may be moved by utilizing capillary phenomenon. Accordingly, since the provision of the external force applying unit is not required, separation operation can easily be performed while the system configuration can be simplified. Therefore, the separation operation and the mass spectrometric analysis operation subsequent to it can be performed more efficiently. For example, the separation operation can easily be performed in the chamber in which the mass spectrometric analysis is performed. In the mass spectrometry system of the invention, a micro channel may be formed in the sample separation area, and the sample may be introduced from the channel to the sample separation area through the micro channel by capillarity.

In the mass spectrometry system of the invention, an upper portion of the channel may be coated with a thin film including a matrix for mass spectrometric analysis. Accordingly, the drying of the sample in the channel can preferably be suppressed during the separation. After the separation, because the sample may be irradiated with the laser beam without removing a coating, the operation in which the matrix is previously mixed in the sample or the operation in which the matrix is added to the sample separation area after the sample separation is not required.

According to the invention, there is provided a mass spectrometry system comprising a substrate; a sample separation area in which sample adsorption particles adhere to the substrate to develop a sample according to a specific property; a light irradiation unit irradiating with a laser beam while moving a light irradiation position along the sample separation area; and an analytical unit analyzing a fragment of the sample to obtain mass spectrometric data, a fragment of the sample being generated by a light irradiation. In the invention, the term of development should mean that the sample is distributed in the sample separation area according to the property of the sample, and the separation should be one of modes of the development.

The sample separation area in which sample adsorption particles adhere to the substrate can easily be formed in a simple manner when compared with the area in which the fine processing is performed into the channel. The sample can be developed according to affinity between the sample and a developing solution for developing the sample. The sample can also be developed according to the polarity. Therefore, the sample can securely be separated. Further, according to the invention, the separation can be started while the sample is dried to a certain degree. Therefore, the band width of the sample can be narrowed.

In the mass spectrometry system of the invention, the sample adsorption particles may be silica gels. Accordingly, the sample can securely be developed according to the property of the developing solution while securely adsorbed to the adsorption particles.

According to the invention, there is provided a method of analysis in which a mass spectrometric analysis is performed with the use of a microchip having a sample separation area, comprising: a step of separating a sample in the sample separation area according to a specific property of the sample; a step of irradiating with a laser beam while moving a light irradiation position along the sample separation area; and a step of analyzing a fragment of the sample to obtain mass spectrometric data, the fragment of the sample being generated by a light irradiation.

According to the invention, there is provided a method of analysis in which a mass spectrometric analysis is performed with the use of a microchip having a sample separation area, comprising: a step of developing a sample in the sample separation area according to a specific property of the sample; a step of irradiating with a laser beam while moving a light irradiation position along the sample separation area; and a step of analyzing a fragment of the sample to obtain mass spectrometric data, the fragment of the sample being generated by a light irradiation.

In the analytical method according to the invention, the analysis can be performed by combination of the position of each component in the sample separated or developed and the mass spectrometric analysis spectrum of the component, which allows the spectrum property of each component to be efficiently fully obtained. Therefore, the identification of the component in the sample and the like can rapidly be performed with high accuracy based on the obtained information.

The analytical method of the invention may further comprise a step of obtaining a first mass spectrometric data, the step of obtaining the first mass spectrometric data including a step of depolymerizing the sample after the step of separating a sample; a step of analyzing a fragment of the sample to obtain a second mass spectrometric data by performing the step of irradiating with a laser beam without performing the step of depolymerizing the sample after the step of separating a sample, the fragment of the sample being generated by a light irradiation; and a step of identifying the sample based on the first mass spectrometric data and the second mass spectrometric data.

The analytical method of the invention may further comprise a step of obtaining a first mass spectrometric data, the step of obtaining the first mass spectrometric data including a step of depolymerizing the sample after the step of developing a sample; a step of analyzing a fragment of the sample to obtain a second mass spectrometric data by performing the step of irradiating with a laser beam without performing the step of depolymerizing the sample after the step of developing a sample, the fragment of the sample being generated by a light irradiation; and a step of identifying the sample based on the first mass spectrometric data and the second mass spectrometric data.

When the sample to be analyzed is depolymerized prior to the separation or the development, because the sample is depolymerized while the components in the sample are mixed, in the conventional art, it is difficult to determine that the separated or developed fragment is derived from which component in the sample. On the contrary, in the invention, because the sample is depolymerized without moving the sample from the inside of the sample separation area after the sample is previously separated or developed, the mass spectrometric data for the depolymerized fragment can be obtained in each component contained in the sample, which enables the further detailed analysis. The sample is identified by combining the first mass spectrometric data obtained by depolymerizing each component in the separated or developed sample and the second mass spectrometric data obtained without depolymerizing each component. Therefore, the detailed information on each component in the sample can be obtained with higher accuracy.

The analytical method of the invention may further comprise a step of immobilizing the separated sample to the sample separation area prior to the step of irradiating with a laser beam after the step of developing a sample. Further, an analytical method of the invention may include a step of immobilizing the developed sample to the sample separation area prior to the step of irradiating with a laser beam after the step of developing a sample.

Accordingly, the sample can be irradiated with the laser beam while immobilized at the separated or developed position. Therefore, the diffusion of the separated or developed sample can be suppressed in the sample separation area, and the accuracy of the separated or developed position information can be improved. Further, even in depolymerizing the sample, the diffusion of the depolymerized sample is suppressed by immobilizing the sample to the sample separation area prior to the depolymerization, which allows the higher-accuracy information to be obtained.

The analytical method of the invention may further comprise a step of spraying a matrix for mass spectrometric analysis onto the sample separation area prior to the step of irradiating with a laser beam after the step of developing a sample. Further, an analytical method of the invention may further comprise a step of spraying a matrix for mass spectrometric analysis onto the sample separation area prior to the step of irradiating with a laser beam after the step of developing a sample. Accordingly, the matrix for mass spectrometric analysis can easily be added to the separated or developed sample, which allows the matrix assist-type mass spectrometric analysis to be efficiently performed.

Both arbitrary combinations of these configurations and the changes in expression of the invention in the method or apparatus should also be effective as the mode of the invention.

As described above, the technology in which the sample separation and the mass spectrometric analysis are easily performed with high accuracy is realized by the invention. Specifically, the novel mass spectrometry which can obtain the detailed information on the analytical target without performing the component identification and the system which achieves the mass spectrometry are realized.

BRIEF DESCRIPTION OF THE DRAWINGS

The above object, other objects, advantages, and features of the invention will become more apparent in the following embodiments and the accompanying drawings.

FIG. 12 is a view for explaining the method of forming the nanostructure shown in FIG. 10;

FIG. 13 is a view for explaining the method of forming the nanostructure shown in FIG. 10;

FIG. 20 is a view for explaining the microchip producing method;

FIG. 26 is a view for explaining a method of producing the separation channel of the microchip;

FIG. 27 is a view for explaining the method of producing the separation channel of the microchip;

FIG. 28 is a view showing an example of a columnar body arrangement method;

FIG. 33 is a view showing an example of the columnar body arrangement method;

FIG. 34 is a view showing a configuration of the microchip used for a mass spectrometry system according to an embodiment;

FIG. 41 is a view showing an example of a channel structure;

FIG. 53 is a view for explaining a shape of the concaves in the microchip used for the mass spectrometry system according to an embodiment;

FIG. 54 is a view showing an example of a configuration of the separation channel in the microchip;

FIG. 55 is a view showing an example of a configuration of the separation channel in the microchip;

FIG. 61 is a view showing a detailed configuration of the separation channel in the microchip according to an embodiment;

FIG. 64 is a view for explaining the microchip producing method;

FIG. 68 is a view for explaining the microchip producing method;

FIG. 70 is a view for explaining the microchip producing method;

FIG. 74 is a view showing an example of a configuration of the channel in the microchip;

FIG. 75 is a view for explaining a pillar mesh function;

FIG. 76 is a view showing a configuration of the microchip used for the mass spectrometry system according to an embodiment;

FIG. 82 is a view for explaining the fragment pattern obtained by the mass spectrometry system according to an embodiment;

FIG. 84 is a view showing a method of spraying a matrix solution into the channel;

FIG. 85 is a view for explaining a sample pretreatment method;

FIG. 86 is a view showing an example of a configuration of the columnar body; and FIG. 87 is a view showing a state in which the peripheral portion of the aluminum layer is covered with an electroconductive layer.

BEST MODE FOR CARRYING OUT THE INVENTION

Embodiments of the invention will be described below. In the following embodiments, any one of configurations shown in FIGS. 3, 21, 22, 23, 35, 37, and 76 may be adopted as the whole configuration of the microchip. In the embodiment of the specification, "pillar" is a shown as a mode of the columnar body, and "pillar" should mean micro-columnar body having a shape of a circular cylinder or an elliptical cylinder. "Pillar patch" and "patch area" are shown as a mode of columnar body arrangement portion, and "pillar patch" and "patch area" should mean an area where a large number of pillars are formed in a cluster.

First Embodiment

Figure 1:
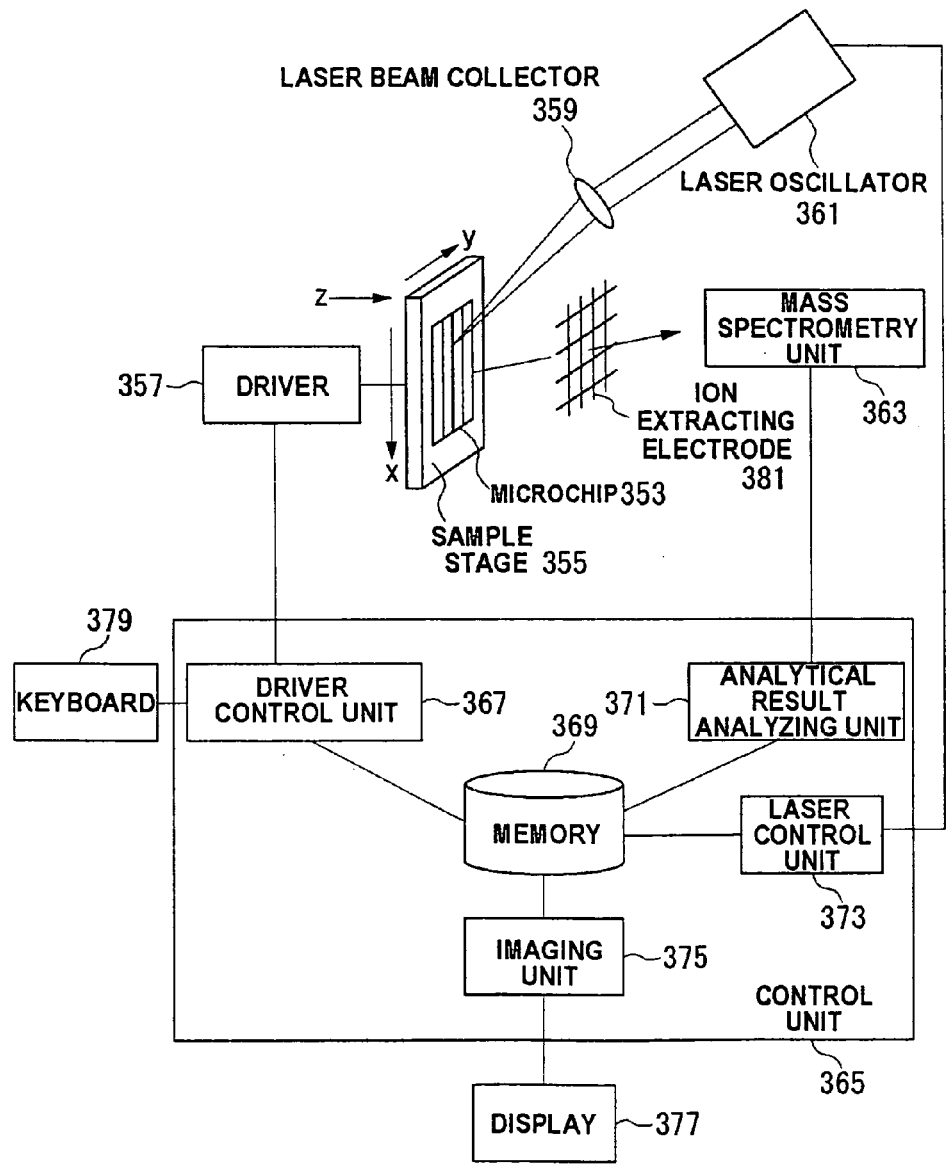
FIG. 1 is a view showing a configuration of a mass spectrometry system according to an embodiment.

FIG. 1 is a view showing a configuration of a mass spectrometry system according to the embodiment. In a mass spectrometry system 351 of FIG. 1, a channel (not shown) formed in a microchip 353 on a sample stage 355 is irradiated with a laser beam emitted from a laser oscillator 361, and a sample separated in the channel is ionized. At this point, the laser beam emitted from the laser oscillator 361 is condensed by a laser beam collector 359 and irradiated along the channel on the microchip 353. Therefore, after the sample is previously separated into plural components in the channel on the microchip 353, the channel is irradiated with the laser beam along a separation direction, which allows each separated fraction to be sequentially ionized. A mass spectrometry unit 363 detects the ionized fragment through an ion extracting electrode 381.

During the laser irradiation along the channel, the position of the channel on the microchip 353 is moved by a driver 357 which adjusts the position of the sample stage 355 on which the microchip 353 is placed. A driver control unit 367 controls action of the driver 357. In the driver control unit 367, a drive method may be inputted from a keyboard 379. A laser control unit 373 controls the laser irradiation from the laser oscillator 361. An analytical result analyzing unit 371 analyzes the signal detected by the mass spectrometry unit 363.

The analytical result performed by the analytical result analyzing unit 371 is stored in a memory 369 while associated with position information in the driver control unit 367 and information on laser beam irradiation condition in the laser control unit 373. The analytical result is imaged by an imaging unit 375. A display 377 displays the imaged analytical result.

A control unit 365 which controls the mass spectrometry system includes the driver control unit 367, the analytical result analyzing unit 371, the laser control unit 373, the memory 369, and the imaging unit 375.

Figure 2:
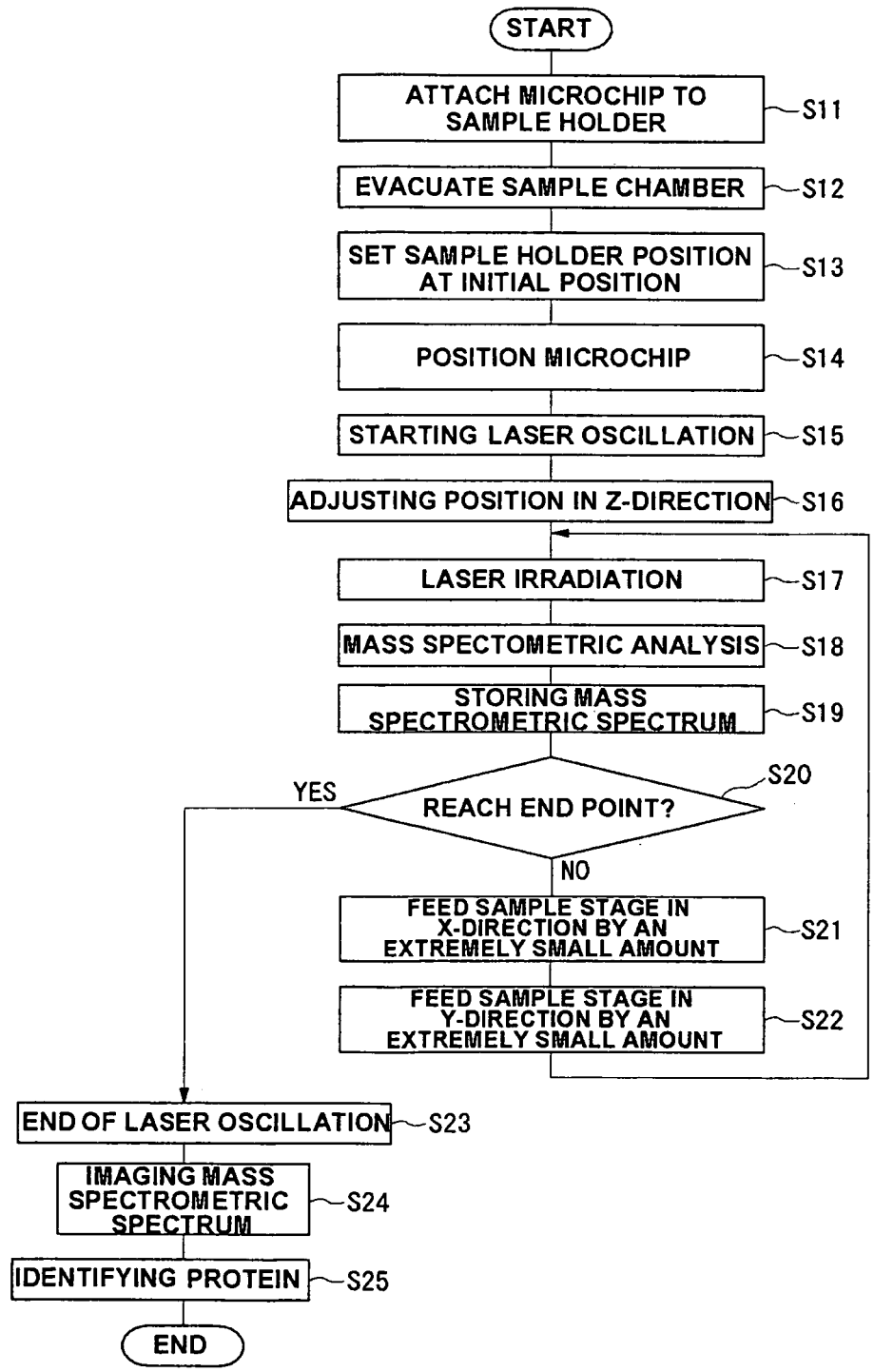
FIG. 2 is a view showing mass spectrometry in which the mass spectrometry system of FIG. 1 is used.

Then, a mass spectrometry system procedure with the mass spectrometry system 351 will be described with reference to FIG. 2. FIG. 2 is a view showing the mass spectrometry in which the mass spectrometry system of FIG. 1 is used. After the sample is separated into fractions by the channel (not shown) on the microchip 353, the microchip 353 is attached to a sample holder (not shown) on the sample stage 355 (S11). A pressure is reduced in a sample chamber (not shown) to form a vacuum (S12).

The driver 357 sets the position of the sample holder on the sample stage 355 as an initial state (S13), and positioning is performed such that the channel (not shown) on the microchip 353 is irradiated with the laser beam (S14). The laser oscillation of the laser oscillator 361 is started (S15), and the position of the microchip 353 is adjusted in a Z (height) direction (S16).

Then, the channel (not shown) on the microchip 353 is irradiated with the laser beam (S17), the mass spectrometric analysis is performed (S18), a spectrum obtained by the analytical result analyzing unit 371 is stored in the memory 369 (S19). Each step of STEPS 17 to 19 is repeated to an end point (NO in S20) while the sample stage 355 is sequentially moved by a micro length in an X direction and a Y direction (S21 and S22).

When the laser irradiation is performed to the end point (YES in S20), the laser oscillator 361 is stopped (S23), the obtained mass spectrum is imaged by the imaging unit 375 (S24). Identification of the protein and the like are performed based on the image for each component (S25).

In the mass spectrometric analysis of STEP 18, both LD (Laser Desorption Ionization) and MALDI (Matrix Assist Laser Desorption Ionization) may be used as long as the ionization method is one which is performed by the laser irradiation. There is no particular limitation to the method of separating the ionized sample which can be separated by a TOF (time of flight) method and other given methods. Instead of the mass spectrometric analysis (MS), MS/MS may be used in STEP 18. When MS/MS is used, the more detailed information can be obtained.

Examples of the matrix include sinapic acid, α-CHCA (α-cyano-4-hydroxycinnamic acid), 2,5-DHB (2,5-dihydroxybenzoic acid), a mixture of 2,5-DHB and DHBs (5-methoxysalicylic acid), HABA (2-(4-hydroxyphenylazo) benzoic acid), 3-HPA (3-hydroxypicolinic acid), dithranol, THAP (2,4,6-trihydroxyacetophenone), IAA (trans-3-indoleacrylic acid), picolinic acid, nicotinic acid, and the like. In the case where the sample is an unmodified protein, it is preferable that 2-DHB is used as the matrix and ionization is performed by infrared laser beam irradiation. Therefore, the sample can securely be ionized to improve the measurement accuracy.

In the case of the use of the matrix, the substance used as the matrix may be introduced in the channel at predetermined timing, or may previously added to a mobile phase such as a buffer solution. Further, the channel may be coated with the matrix solution by spraying or the like after the sample is separated.

FIG. 84(*a*) to 84(*c*) are a view showing the method of spraying the matrix solution onto the channel. Referring to FIG. 84(*a*), the microchip 353 is placed on a metal plate 383, and a matrix solution 387 is sprayed from a nebulizer 385 by an electro-spray method. The electro-spray method is one which utilizes a phenomenon in which liquid in a thin metal tube is sprayed into fine particles when high voltage is applied to the tube.

The voltage ranging from 500V to 5 kV is applied between the nebulizer 385 and the metal plate 383 to spray the matrix solution 387 from the position distant from the channel (not shown in FIG. 84(*a*)) on the microchip 353 in the range of about 5 mm to about 10 cm, which allows the matrix solution 387 to be sprayed onto the channel. At this point, for example the amount of spray can be set to about microliters per minute.

FIG. 84(*b*) shows the method of spraying the matrix solution 387 from a nebulizer 389 by pressure of nebulizer gas. For example, an inert gas such as $N_2$, Ar or the like can be used as the nebulizer gas.

FIG. 84(*c*) is the view showing a nebulizer 399 in which the electro-spray method and the pressure of the nebulizer gas can be used in combination. When the voltage is applied between the nebulizer 399 and the metal plate 383 like the case of FIG. 84(a), it can be used as the electro-spray method. It is also configured to be able to spray the matrix solution 387 without applying the voltage by the pressure of the nebulizer gas like the case of FIG. 84(b). Further, it can spray the matrix solution 387 by imparting the voltage and the gas pressure at the same time.

It is also possible that the matrix is formed in a sheet shape and the channel is coated with the sheet-like matrix. Therefore, drying of the sample is suppressed during the separation, and it is not necessary that the sheet on the upper portion of the channel is removed after the separation. Further, when the sample is irradiated with the laser beam while the sheet is provided, because the sample and the matrix are mixed, the operation in which the matrix is added to the post-separation sample is not required.

The configuration of the microchip 353 used for the mass spectrometry system 351 of FIG. 1 will be described below. In the microchip 353 used for the mass spectrometry system 351, the channel and the sample separation area can be formed in the surface of a silicon substrate, a glass substrate such as quartz, and a resin substrate such on silicone resin. For example, a groove portion is provided in the surface of the substrate and the groove portion is sealed by a surface member, which allows the channel and the sample separation area to be formed in a space surrounded thereby.

The plural columnar bodies are provided in the separation area. The columnar body can be formed by etching the substrate in a predetermined pattern shape. However, there is no particular limitation in the producing method thereof.

The shape of the columnar body includes various shapes, for example, pseudo-cylindrical shapes such as a circular cylinder and an elliptic cylinder; cones such as a circular cone, an elliptic cone, and a triangular cone; prisms such as a triangle prism and square prism; and a stripe-shaped projection. In the dimension of the columnar body, a width ranges from about 10 nm to about 1 mm, and a height ranges from about 10 nm to about 1 mm.

The interval between the adjacent columnar bodies is appropriately set according to the purpose of the separation. For example, in the processes of:
(i) The separation and the condensation of a cell and other components,
(ii) The separation and the condensation of a solid matter (fragment of cell membrane, mitochondria, and endoplasmic reticulum) and a liquid fraction (cytoplasm) in the components obtained by destroying the cell, and
(iii) The separation and the condensation of a high-molecular weight component (DNA, RNA, protein, and sugar chain) and a low-molecular weight component (steroid, glucose, and the like) in the liquid fraction component,
in the case of (i), it can be set in the range of 1 μm to 1 mm, in the case of (ii), it can be set in the range of 100 nm to 10 μm, and
in the case of (iii), it can be set in the range of 1 nm to 1 μm.

One or more columnar body arrangement portions can be provided in the sample separation area. The columnar body arrangement portion includes columnar body groups. The columnar body groups in each columnar body arrangement portion can arbitrarily be arranged in different dimensions at different intervals. The columnar bodies may be formed in the substantially same dimension and regularly arranged at even intervals.

A path through which the sample can pass is formed in the interval between the adjacent columnar body arrangement portions. At this point, when the interval between the columnar body arrangement portions is larger than the interval between the columnar bodies, the gigantic-size molecule and the like can smoothly be moved, so that the separation efficiency can further be improved.

Figure 3:
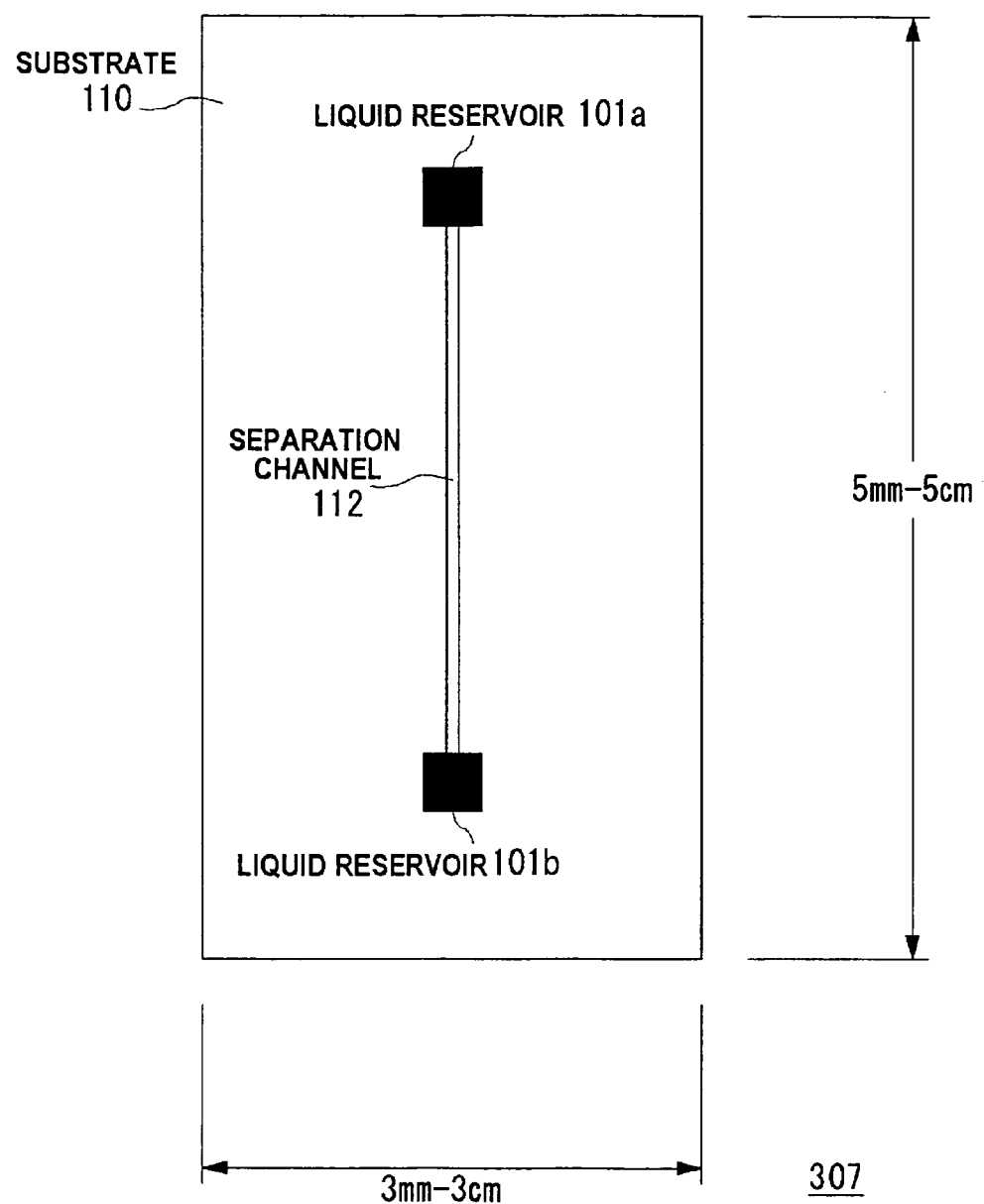
FIG. 3 is a view showing a configuration of a microchip used for the mass spectrometry system of FIG. 1.

FIG. 3 is a view showing the configuration of the microchip 307 which is placed as the microchip 353 on the sample stage 355 of the mass spectrometry apparatus 351. A separation channel 112 is formed on a substrate 110, and a liquid reservoir 101a and a liquid reservoir 101b are formed at both ends thereof. The plural columnar bodies (not shown) are arranged in the separation channel 112 to separate the sample. Electrodes (not shown) are provided in the liquid reservoir 101a and the liquid reservoir 101b, and the voltage can be applied to the both ends of the separation channel 112 by using the electrodes. Arbitrary values are selected as outside dimensions of the microchip 307 as usage. For example, as shown in FIG. 3, a longitudinal value ranges from 5 mm to 5 cm and a transverse value ranges from 3 mm to 3 cm.

Figure 4:
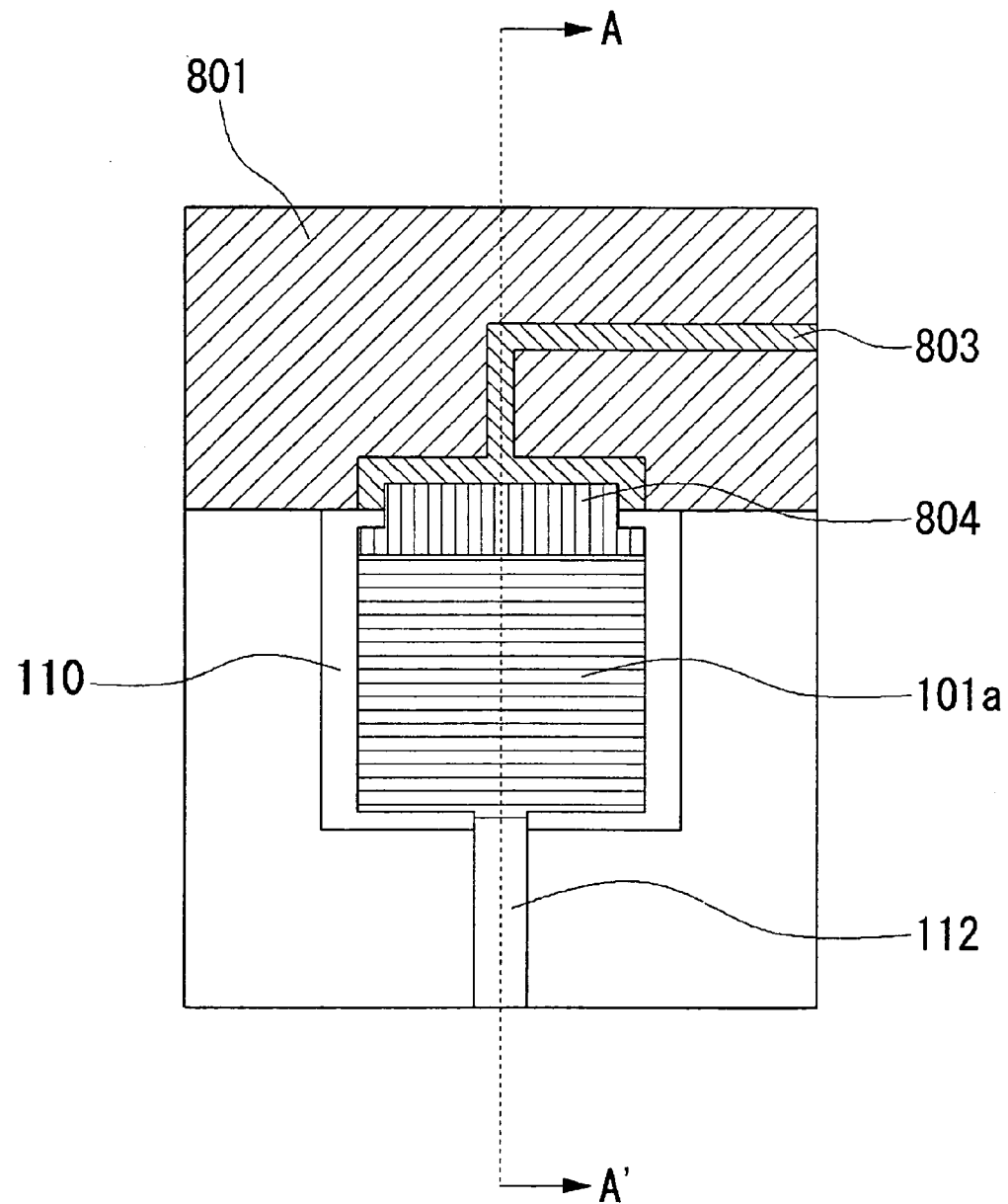
FIG. 4 is a view for explaining a configuration of a liquid reservoir in the microchip of FIG. 3.
Figure 5:
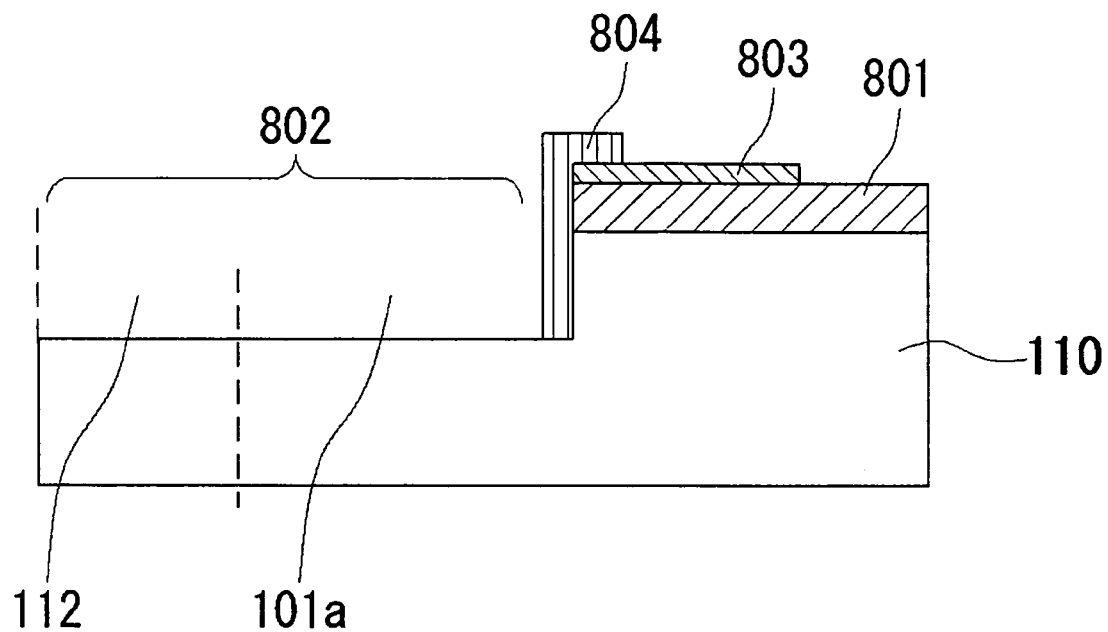
FIG. 5 is a sectional view taken on line A-A' of FIG. 4.

The configuration of the liquid reservoir in which the electrode is provided will be described by taking the liquid reservoir 101a as an example with reference to FIGS. 4 and 5. FIG. 4 is an enlarged view near the liquid reservoir 101a of FIG. 3. FIG. 5 is a sectional view taken on line A-A' of FIG. 4. As shown in FIGS. 4 and 5, a cover 801 is arranged on the substrate 110 in which the separation channel 112 and the liquid reservoir 101a are provided. An opening 802 through which the buffer solution is injected in is provided in the cover 801. The liquid reservoir 101a, the liquid reservoir 101b, and the separation channel 112 are not covered with the cover 801, and the upper portions thereof are opened. An conductive path 803 which can be connected to an external power supply is provided on the cover 801. An electrode plate 804 is arranged along a wall surface of the liquid reservoir 101a and the conductive path 803. The electrode plate 804 and the conductive path 803 are crimped and electrically connected. The liquid reservoir 101b can be formed in the same structure.

Returning to FIG. 3, the method of separating the sample with the microchip 307 will be described. First the liquid such as the buffer solution is introduced from the liquid reservoir 101a into the separation channel 112. The sample is injected in the liquid reservoir 101a. Then, the voltage is applied between the liquid reservoir 101a and the liquid reservoir 101b such that the sample flows toward the direction of the liquid reservoir 101b, which allows the sample to pass through the separation channel 112. During this time, the sample goes through the separation channel 112 at speed according to the molecular size, charge intensity, and the interval between the columnar bodies. As a result, the different molecular groups in the sample are separated in the bands which are moved at different speeds.

Figure 6:
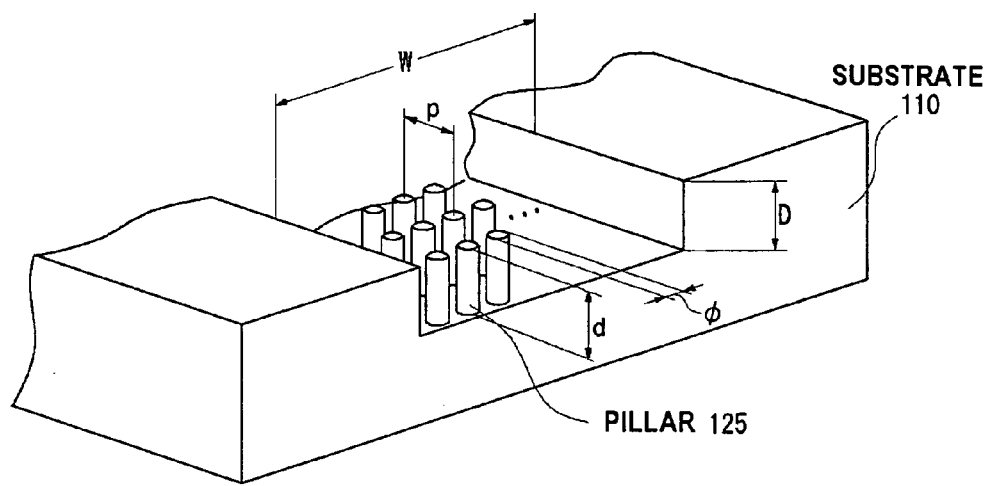
FIG. 6 is a view showing a detailed configuration of a separation channel in FIG. 3.

Then, the structure of the separation channel 112 in the microchip 307 will be described. FIG. 6 shows the detailed structure of the separation channel 112 in FIG. 3. The structure shown in FIG. 6 can be also applied to the drawings subsequent to FIG. 6. Referring to FIG. 6, a groove portion having a width W and a height D is formed in the substrate 110, cylindrical pillars 125 having diameters $\phi$ and the heights d are regularly formed therein at even intervals. The sample passes through the interval between the pillars 125. An average interval between the adjacent pillars 125 is p. For example, each dimension can be set in the range shown in FIG. 6.

Figure 7:
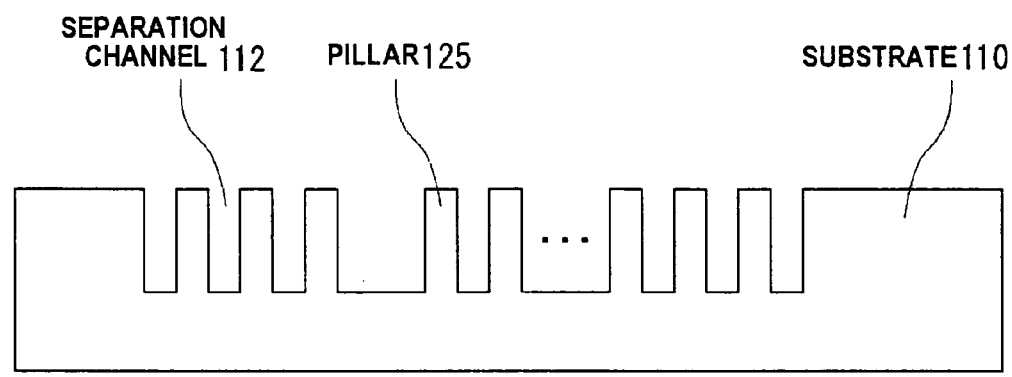
FIG. 7 is a sectional view of the separation channel of FIG. 6.

FIG. 7 is a sectional view of the separation channel 112 of FIG. 6. The many pillars 125 are formed in the space of the groove portion made in the substrate 110. The interval between the pillars 125 forms the separation channel 112.

Figure 8:
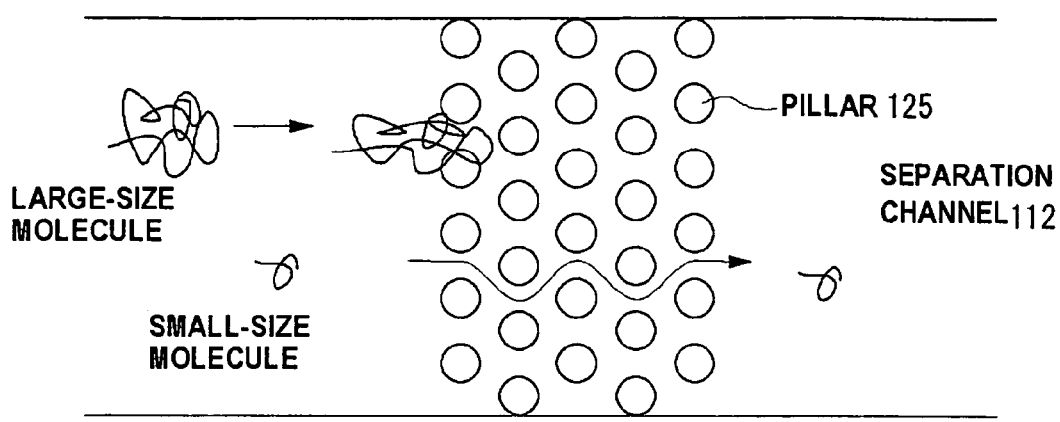
FIG. 8 is a view for explaining a sample separation method.

In the case where the structure in which the many pillars 125 are densely formed is used as the sample separation unit, mainly there are two separation methods. One is the separation method shown in FIG. 8. The other will be described in a fourth embodiment with reference to FIG. 25. In the method of FIG. 8, as the molecular size is increased, the pillar 125 becomes an obstacle and the passing time through the separation area in FIG. 8 becomes longer. When the molecular size is small, the molecule passes relatively smoothly through the interval between the pillars 125, and the molecule passes through the separation area at short times when compared to the molecule having the large molecular size.

The plural components in the sample can securely be separated by using the pillars 125. The sample is separated by using the microchip 307 as the microchip 353 in FIG. 1, then it is placed on the sample stage 355 of the mass spectrometry system 351 of FIG. 1 and is irradiated along the separation channel 112 with the laser beam from the laser oscillator 361, so that each of the separated bands is ionized. The separation operation may be performed on the sample stage 355 and the mass spectrometric analysis may be consecutively performed.

Thus, the extraction, the drying, and the structural analysis of the target component can be performed on one microchip 307 in this embodiment. The microchip 307 and the mass spectrometry system 351 are also useful to, for instance, proteome analysis.

A coating (not shown) may be provided in the upper portion of the separation channel 112 in performing the separation. Provision of the coating can suppress the sample drying during the separation. For example, a film made of PDMS (polydimethylsiloxane) can be used as a material used for the coating. Because the PDMS film has easy detachment and excellent sealing properties, the use thereof can preferably suppress the sample drying during the separation. The PDMS film can easily be peeled off from the substrate 110 after the separation is ended, so that the sample is rapidly dried to perform the mass spectrometric analysis after the separation. As described above, the matrix may be formed in the sheet shape to use the sheet-like matrix as the coating.

In the above descriptions, the columnar bodies are arranged at even intervals. However, the columnar bodies can be arranged at different intervals in the columnar body arrangement portion. Therefore, the molecules or ions having the plural sizes such as the large size, the medium size, and the small size can further efficiently be separated. For the arrangement of the columnar bodies, it is also effective to adopt the method of arranging the columnar bodies in a zigzag manner with respect to the sample forward direction. Therefore, the target component can efficiently be separated while the clogging can effectively be prevented.

In order to prevent the adhesion of the molecules such as DNA and the protein to a wall surface of the separation channel 112, it is preferable that the channel wall is coated. Therefore, the microchip 307 can exert the good separation ability. The substances having the structure similar to phospholipids constituting the cell membrane can be cited as an example of the coating material. An example of the substance includes LIPIDURE (registered trademark, product of NOF CORPORATION). When LIPIDURE (trademark) is used, it is dissolved in the buffer solution such as TBE (Tris-borate+ EDTA) buffer, at the concentration of 0.5 wt %, the separation channel 112 is filled with this solution, and is left for several minutes. Therefore, the channel wall can be coated. The molecules such as DNA can also be prevented from adhering to the channel wall by coating the channel wall with a repellent resin such as fluororesin or a hydrophilic substance such as bovine serum albumin.

It is preferable that the microchip 307 is used while the buffer solution is introduced in the microchip 307. When the channel surfaces such as the wall surface of the separation channel 112 and the coating portion of the wall surface is formed by the hydrophobic material such as plastic, usually it is not easy to introduce the buffer solution. For example, the method shown in FIG. 9 can be adopted as the method of smoothly introducing the buffer solution. In the method shown in the drawing, centrifugal separation is performed while a chip 150 is fixed into a holder 153 of a centrifuge tube 151, which allows the buffer solution to be introduced into the chip 150. The buffer solution can securely be introduced into the channel of the microchip 307 by applying the microchip 307 as the chip 150.

Figure 17:
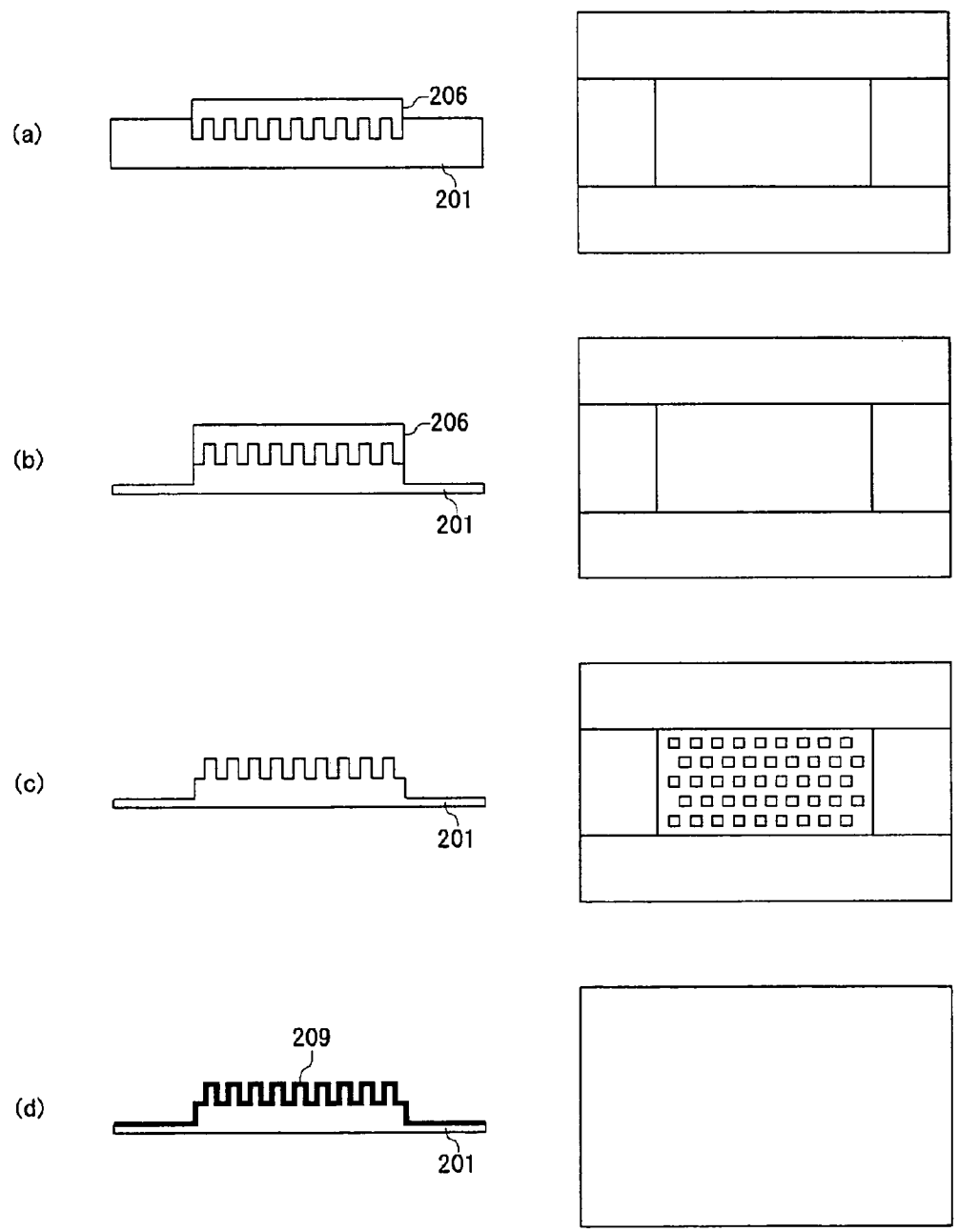
FIG. 17 is a view for explaining the microchip producing method.

The formation of the hydrophilic film such as a silicon oxide film and the like on the surface of the separation channel 112 is effective as the method of more securely introducing the buffer solution into the channel. The formation of the hydrophilic film enables the buffer solution to be smoothly introduced without particularly imparting the external force. This point will be described later with reference to FIG. 17 (silicon thermal oxide film 209 formed through a process of FIG. 17(d)).

When the mass spectrometric analysis is performed with the microchip 307 in which the channel wall is coated as described above, sometimes the coating substance is detected as the background. However, when the silicon thermal oxide film is formed to achieve the hydrophilic state of the channel surface, as described later the background can be decreased during the mass spectrometric analysis to further improve the measurement accuracy.

In the columnar body provided in the separation channel 112 of the microchip 307, it is preferable that the diameter of a top portion is smaller than that of a bottom portion. That is, it is preferable that the columnar body has the cone or pseudocone shape and the section is widened toward the end. Particularly, when the hydrophilic film such as the silicon oxide film is formed on the columnar body surface, the effect of the above shape becomes remarkable. For example, when the thermal oxide film is provided on the surface of the columnar body by performing the thermal oxidation of the columnar body, sometimes the oxidation progresses near the bottom portion of the columnar body and the height of the columnar body is decreased to decrease an aspect ratio. When the shape of the columnar body is formed in the above manner, the decrease in aspect ratio by the oxidation can effectively be prevented.

Figure 10:
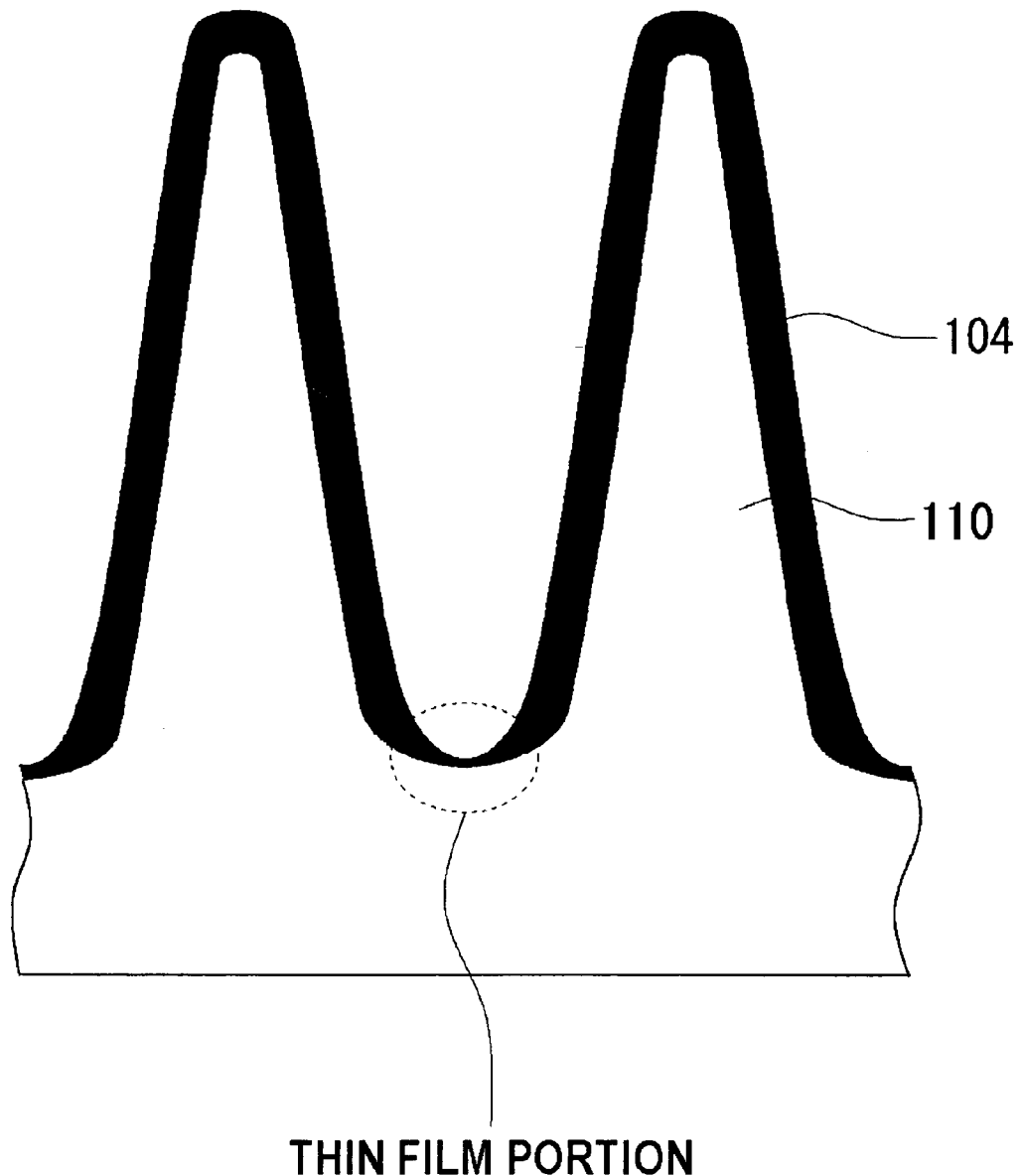
FIG. 10 is a sectional view of a nanostructure formed in the microchip.

When he above shape is adopted as the shape of the columnar body, it is preferable that the columnar body provided in the sample separation area is formed while side surfaces of the adjacent columnar bodies are brought close to each other to an extent in which the side surfaces are brought into contact with each other in the bottom portion of the columnar body. Therefore, the decrease in aspect ratio by the oxidation can further effectively be prevented. FIG. 10 shows an example of the columnar body in which the above structure is adopted. Referring to FIG. 10, the conical columnar body is provided on the surface of the substrate 110, and the surface of the columnar body is covered with a silicon oxide film 104. In the columnar body, the side surfaces of the adjacent columnar bodies are formed while brought close to each other to the extent in which the side surfaces are brought into contact with each other in the bottom portion of the columnar body.

Accordingly, when the surface is covered with the thermal oxide film by performing the thermal oxidation of the substrate 110, a film thickness of the silicon oxide film 104 get thinner in the bottom portion of the columnar body and the aspect ratio of the columnar body can be maintained in the good state. Although the reason is not always apparent, it is guessed that, due to the structure in which the side surfaces of the conical columnar bodies are brought into contact with each other, compressive stress is generated to make the progress of the further oxidation difficult when the oxidation progresses near the bottom portion of the columnar body.

Thus, the structure in which the columnar bodies are formed in the separation channel 112 of the microchip 307 is described above. When the separation channel 112 having the columnar bodies is irradiated with laser beam to ionize the sample, it is preferable that an ultraviolet laser beam having wavelengths of about 200 to about 400 nm or an infrared laser beam having wavelengths of about 800 to about 11000 nm are used as the laser beam. By using these laser beams, even if the sample is the gigantic molecule ranging from 300 kDa to 400 kDa, it can be securely ionized. With reference to the irradiation conditions, for example, the intensity ranges from 0.1 to 500 μJ/pulse, and a pulse width ranges from 1 to 500 ns. In the case of the ultraviolet laser, a spot diameter is 50 μm or less. In the case of the infrared laser, the spot diameter is 500 μm or less.

Figure 11:
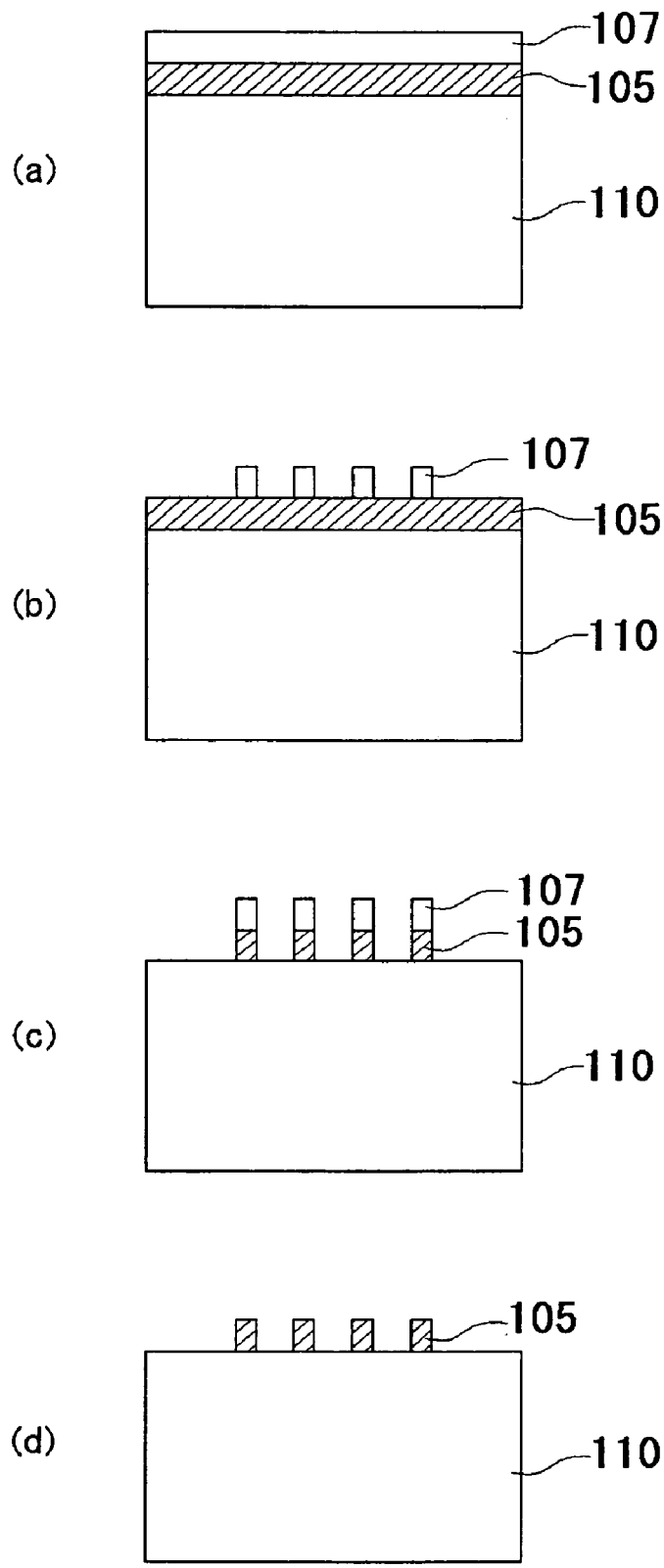
FIG. 11 is a view for explaining a method of forming the nanostructure shown in FIG. 10.

Then, the method of forming the nanostructure shown in FIG. 10 will be described with reference to FIGS. 11 and 12. As shown in FIG. 11(a), a silicon oxide film 105 and a resist film 107 are sequentially deposited on the substrate 110. Then, patterning is performed to the resist film 107 to form the pattern having a predetermined opening by an electron beam exposure and the like (FIG. 11(b)).

Then, dry etching of the silicon oxide film 105 is performed with the resist film 107, which forms a hard mask formed by the silicon oxide film 105 (FIG. 11(c)). After the resist film 107 is removed (FIG. 11(d)), the columnar body having the high aspect ratio is obtained by performing the dry etching of the substrate 110 (FIG. 12(e)). After the silicon oxide film 105 is removed (FIG. 12(f)), the surface is oxidized at high temperatures of 850 degree C. or more to form the silicon oxide film 104 (FIG. 12(g)). The nanostructure shown in FIG. 10 is obtained through the above processes. The nanostructures can be formed in the separation channel 112 of the microchip 307 and used for the sample separation.

In FIGS. 11 and 12, the substrate 110 is etched by the hard mask formed with the resist mask. However, the substrate 110 can directly be etched with the resist mask. FIG. 13 is a view showing the method. In the processes shown in FIG. 13, after a resist 900 is formed on the substrate 110 (FIG. 13(a)), the patterning is performed (FIG. 13(b)), and the columnar bodies are formed by etching the substrate 110 by using it as the mask (FIG. 13(c)).

Figure 14:
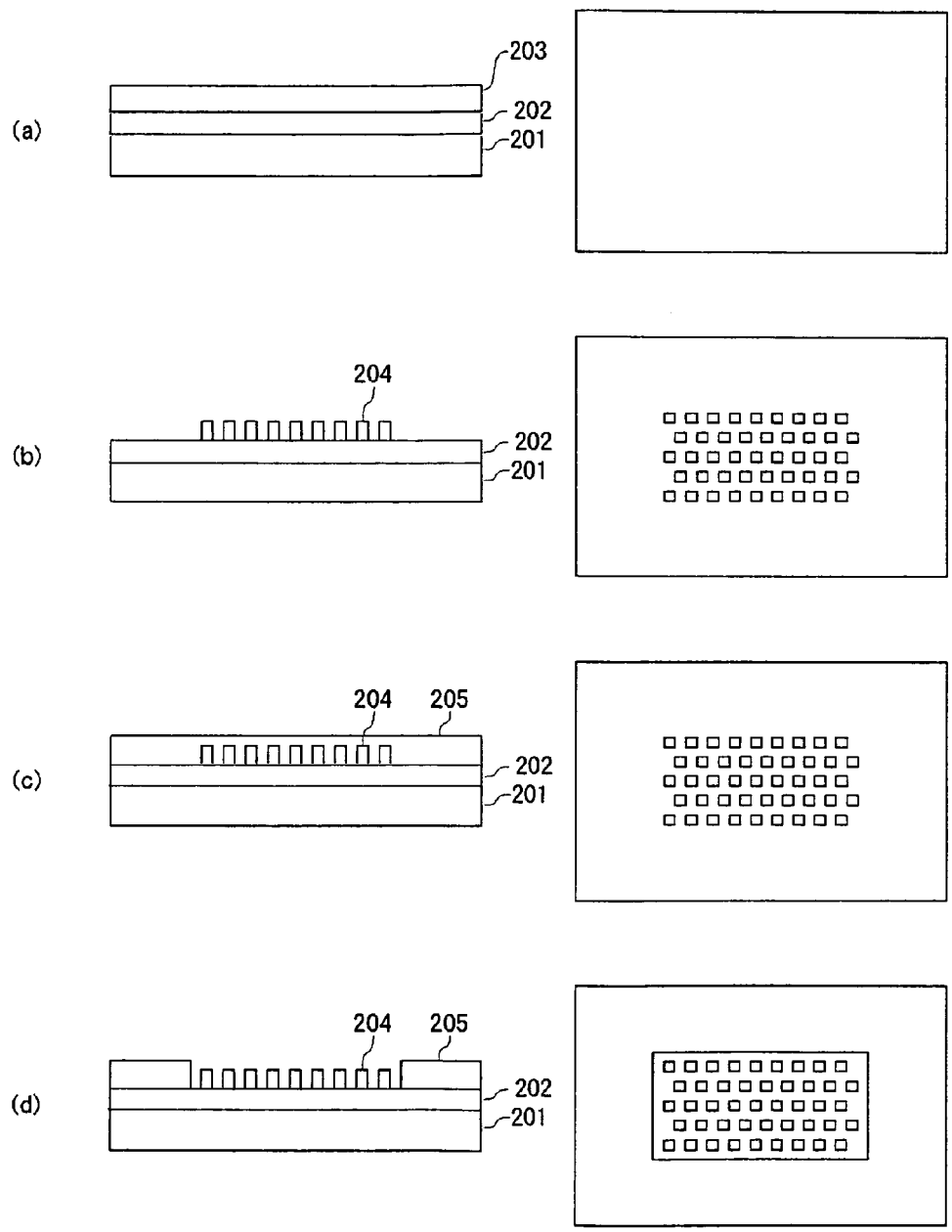
FIG. 14 is a view for explaining a microchip producing method.
Figure 15:
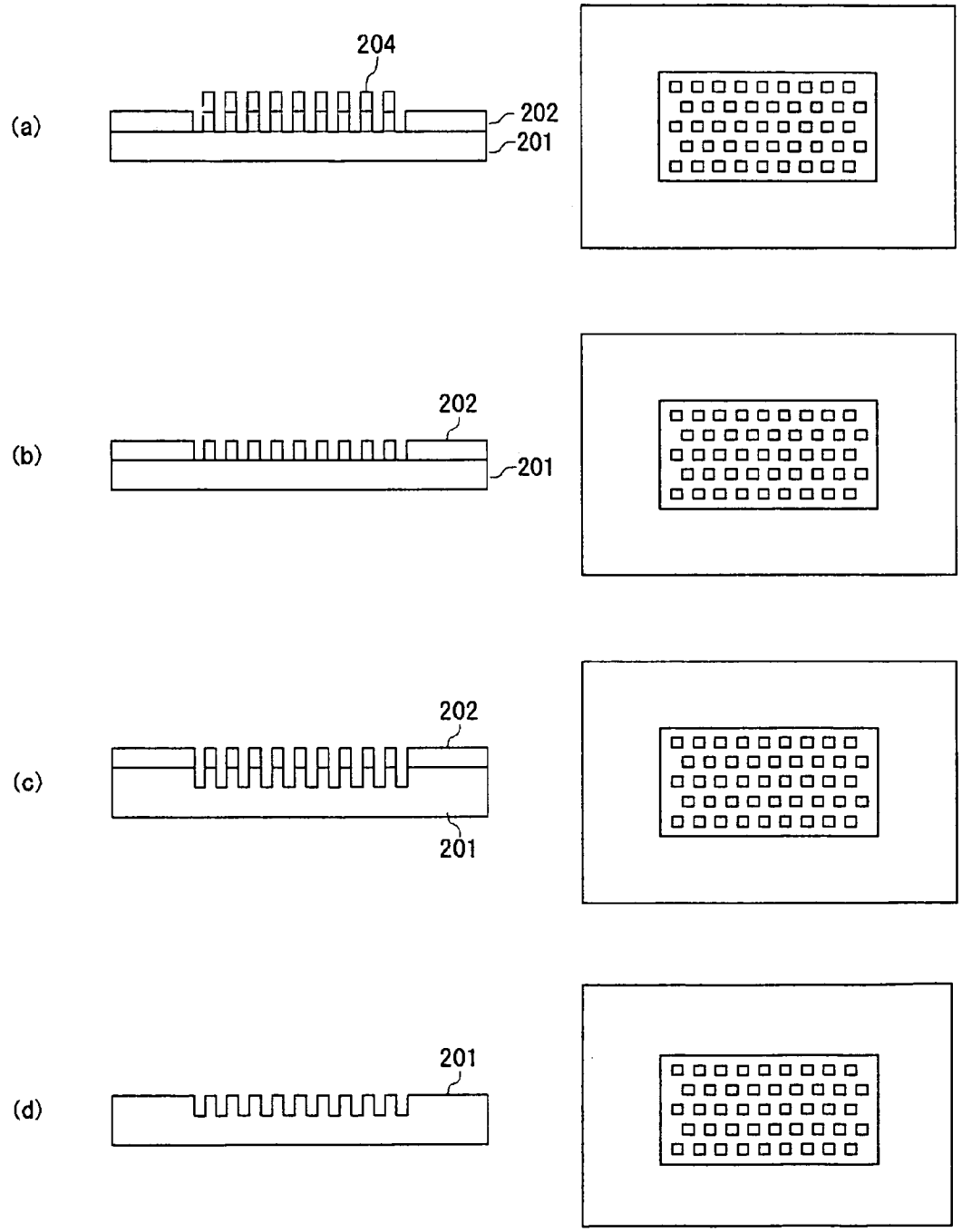
FIG. 15 is a view for explaining the microchip producing method.

Then, another method of forming the channel having the columnar bodies will be described with reference to FIGS. 14 to 18. In FIGS. 14 to 18, a view on the right side is a top view and a view on the left side is a sectional view. As shown in FIG. 14(a), a silicon oxide film 202 and a calix-arene electron beam negative resist 203 are sequentially formed on a silicon substrate 201. The file thicknesses of the silicon oxide film 202 and the calix-arene electron beam negative resist 203 are set at 35 nm and 55 nm respectively. Then, an array area which becomes the sample channel is exposed by the electron beam (EB). Development is performed by xylene, and rinsing is performed by isopropyl alcohol. A resist 204 in which the patterning is performed as shown in FIG. 14(b) is obtained through this process.

The calix-arene electron beam negative resist 203 having the structure shown below is used as an electron beam exposure resist, and the calix-arene electron beam negative resist 203 can preferably be utilized as a nano-processing resist.

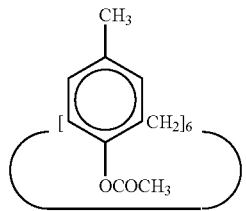

A positive photoresist 205 is coated over the surface (FIG. 14(c)). The film thickness is set at 1.8 μm. Then, mask exposure is performed such that the array area is exposed, and the development is performed (FIG. 14(d)).

RIE etching of the silicon oxide film 202 is performed by using mixture gas of $CF_4$ and $CHF_3$. The post-etching film thickness is set at 35 nm (FIG. 15(a)). The resist 204 is removed by organic washing with mixture solution of acetone, alcohol, and water, and then oxidation plasma treatment is performed (FIG. 15(b)). Then, ECR etching of the silicon substrate 201 is performed with HBr gas. The post-etching film thickness of the silicon substrate 201 is set at 400 nm (FIG. 15(c)). The silicon oxide film 202 is removed by performing wet etching with BHF buffered hydrofluoric acid (FIG. 15(d)).

Figure 16:
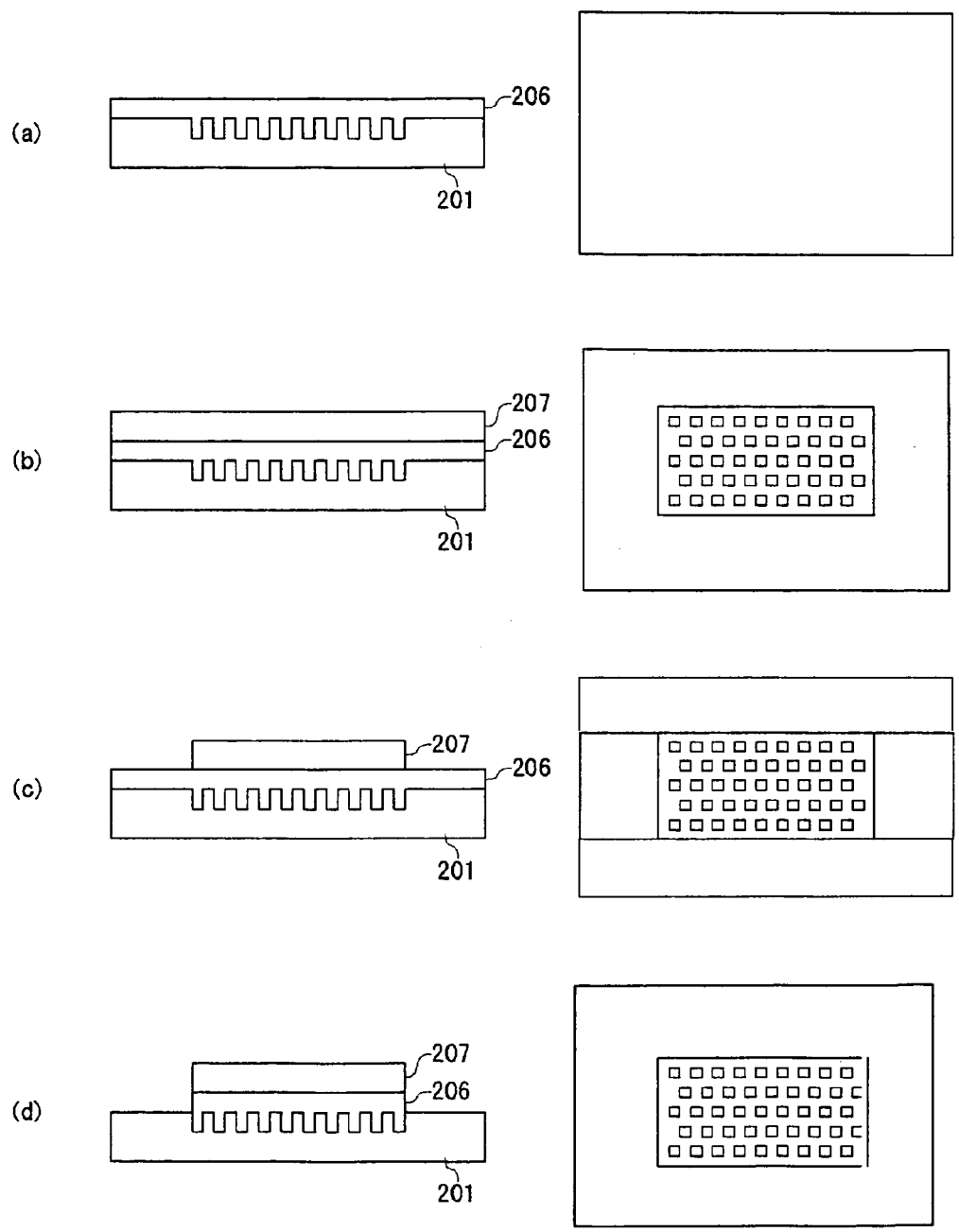
FIG. 16 is a view for explaining the microchip producing method.

A CVD silicon oxide film 206 is deposited on the silicon substrate 201 (FIG. 16(a)). The film thickness is set at 100 nm. Then, a positive photoresist 207 is applied over the surface (FIG. 16(b)). The film thickness is set at 1.8 μm. As shown in FIG. 16 (c), the mask exposure is performed to the channel area (array area is protected) and the development is performed. The wet etching of the CVD silicon oxide film 206 is performed with buffered hydrofluoric acid (FIG. 16(d)). The positive photoresist 207 is removed by the organic washing (FIG. 17(a)), and the wet etching of the silicon substrate 201 is performed with TMAH (tetra methyl ammonium hydroxide) (FIG. 17(b)). The CVD silicon oxide film 206 is removed by performing the wet etching with buffered hydrofluoric acid (FIG. 17(c)).

Figure 18:
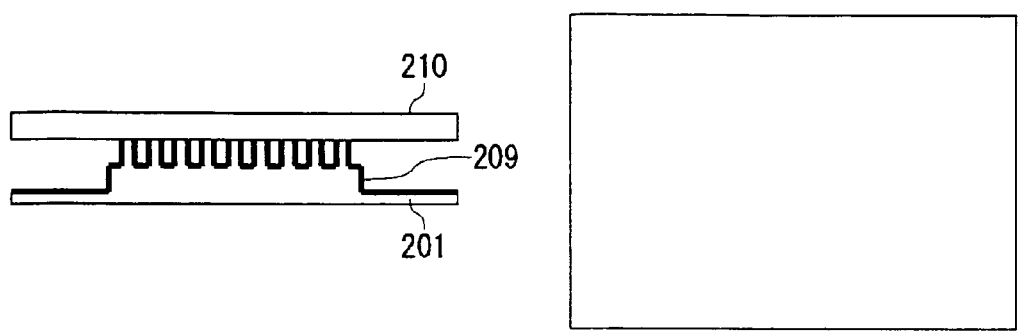
FIG. 18 is a view for explaining the microchip producing method.

Then, the silicon substrate 201 is put into a furnace to form a silicon thermal oxide film 209 (FIG. 17(d)). At this point, heat treatment conditions are selected such that the film thickness of the silicon thermal oxide film 209 is set at, specifically, 20 nm. The formation of such film causes the channel surface to be in the hydrophilic state to eliminate the difficulty in introducing the buffer solution into the channel. Then, a cover 210 may be provided on the channel (FIG. 18).

The channel having the columnar bodies is obtained by the above processes. The silicon substrate 201 is used as the substrate 110 and this method is adopted, which allows the fine columnar body array structure to be securely formed with high accuracy.

Figure 19:
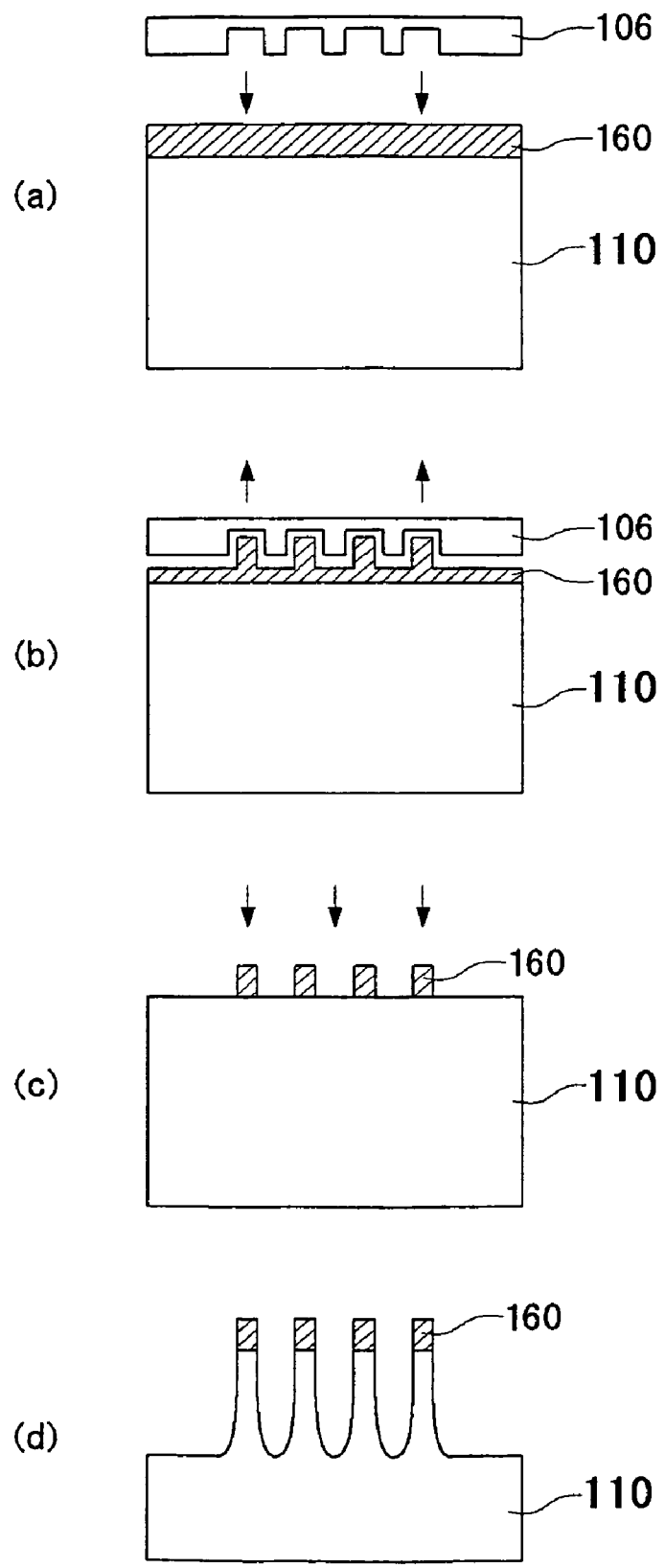
FIG. 19 is a view for explaining a method of forming the separation channel of the microchip.

Further, the method of performing the patterning of the mask with a metal mold will be described as another method of producing the channel having the columnar bodies. FIG. 19 is a process sectional view showing the method of producing the separation channel 112. The substrate 110 and a mold 106 are prepared as shown in FIG. 19(a). The substrate 110 is made of silicon, and a resin film 160 is formed on the surface thereof. A molding surface of the mold 106 is formed in a predetermined relief shape. A poly methyl methacrylate material is used as the material of the resin film 160, and the thickness threrof is set at about 200 nm. The material of the mold 106 is not particularly limited. For example, Si, $SiO_2$, and SiC can be used as the mold 106.

As shown in FIG. 19(b), while the molding surface of the mold 106 is caused to abut on the surface of the resin film 160, the mold is heated and pressed against the resin film 160. The pressure ranges from about 600 to about 1900 psi, and the temperature ranges from about 140 to about 180° C. Then, the substrate 110 is removed, and oxygen plasma ashing is performed to perform the patterning of the resin film 160 (FIG. 19(c)).

The dry etching of the substrate 110 is performed by using the resin film 160 as the mask (FIG. 19(d)). For example, halogen gas is used as etching gas. An etching depth is about 0.4 µm, and the interval between the columnar bodies formed by the etching is about 100 nm. An etching aspect ratio (ratio of height to width) is about 4:1. At this point, due to microloading effect, the progress of the etching slows down near the bottom portion of a concave generated by the etching, and a leading end of the concave is narrowed to form a curved surface. As a result, the columnar body is widened toward the bottom, and the bottom portion is wider than the top portion in the sectional shape of the columnar body. Since the distance between the columnar bodies is narrow, each columnar body is formed while the side surfaces of the adjacent columnar bodies are brought close to each other to the extent in which the side surfaces are brought into contact with each other at the bottom portion of the columnar body.

Subsequent to FIG. 19(d), the thermal oxidation is performed to form a silicon thermal oxide film (not shown in FIG. 19) on the side wall of the columnar body at the temperature from 800 degree C. to 900 degree C. in an annealing furnace. At this point, the shapes of columnar body and the concave are widened toward the bottom, as described in FIG. 10, the thickness of the oxide film is thinned in the bottom portion of the columnar body, so that the aspect ratio of the columnar body can be maintained in the good state.

The columnar body group is formed on the substrate 110 by the above processes. Accordingly, since the process of forming the mask opening by the electron beam exposure is not required, productivity is remarkably improved.

In FIG. 19, the mold is used in patterning the resin film 160 which becomes the mask. However, the columnar bodies can also directly be formed with the mold. Specifically, after the substrate is coated with a given plastic material, the molding can similarly be performed by the above processes. The material having the excellent moldability and appropriate hydrophilic property is preferably used as the plastic material with which the substrate is coated. Polyvinylalcohol resin, in particularly ethylene-vinylalcohol resin (EVOH), polyethylene terephthalate, and the like are preferably used. Even the hydrophobic resin can be utilized, because the channel surface can be formed in the hydrophilic state when the above coating is performed after the molding.

In the above channel forming method, there is a possibility that the film is not sufficiently formed depending on the oxidation condition in forming the silicon thermal oxide film. In this case, because the current leaks to the substrate, the required electric field is not obtained when the sample separation is performed by electrophoresis. In order to avoid this, as shown in FIG. 20, the separation channel and the liquid reservoir can be provided in the substrate.

First, as shown in FIG. 20(a), the silicon oxide film 202 is formed by the thermal oxidation of the silicon substrate 201. Polysilicon is deposited on the silicon oxide film 202 to form a polycrystalline silicon film 707, and then an oxide film 708 is formed by the thermal oxidation of the polycrystalline silicon film 707.

Then, the calix-arene electron beam negative resist is formed on the oxide film 708. The pattern exposure is performed to the area which becomes the liquid reservoir and the sample channel by the electron beam (EB), which allows the resist to be patterned. Then, the RIE etching of the oxide film 708 is performed, and the resist is removed to form the state shown in FIG. 20(b). The ECR etching of the polycrystalline silicon film 707 is performed by using the etched oxide film 708 as a protection film, and then the oxide film 708 is removed to form the state shown in FIG. 20(c). Then, the thermal oxidation of the etched polycrystalline silicon film 707 is performed and integrated with the silicon oxide film 202 to form the state shown in FIG. 20(d).

The separation channel formed by the above processes is completely insulated from the silicon substrate 201. Therefore, when the silicon substrate 201 is used as the substrate 110, the electric field can securely be ensured in imparting the electric field to separate the sample. The quartz substrate may be substituted for the silicon substrate 201 and the silicon oxide film 202. An SOI (Silicon On Insulator) substrate can be utilizes instead of the silicon substrate 201, the silicon oxide film 202, and the polycrystalline silicon film 707.

FIG. 86 is a view showing another configuration of the columnar bodies. Referring to FIG. 86(a), the substrate 110 and the columnar bodies are made of metal. Referring to FIG. 86(b), a metal film 397 is formed on the surface of the columnar body. Thus, when at least the surface of the columnar body is made of metal, the surface plasmon wave is generated on the surface of the columnar body, which allows the ionization of the separated sample to be promoted. The electric field is concentrated on the projection at the leading end of the columnar body, which improves the extraction efficiency of the ionized sample.

For example, the configuration shown in FIG. 86(a) can be formed by etching the metal substrate 110. For example, the processes to FIG. 12(f) are performed to the silicon substrate 110 by the method described in FIGS. 11 and 12, and metal such as silver is evaporated on the surface of the formed columnar body, which allows the configuration shown in FIG. 86(b) to be formed.

For the mass spectrometry system of this embodiment, the human serum is used as the sample and separated by using the microchip including the sample separation portion 112 having the configuration shown in FIG. 3, and the mass spectrometric analysis is performed. The existence of albumin is confirmed from the result of the mass spectrometric analysis.

Second Embodiment

Figure 21:
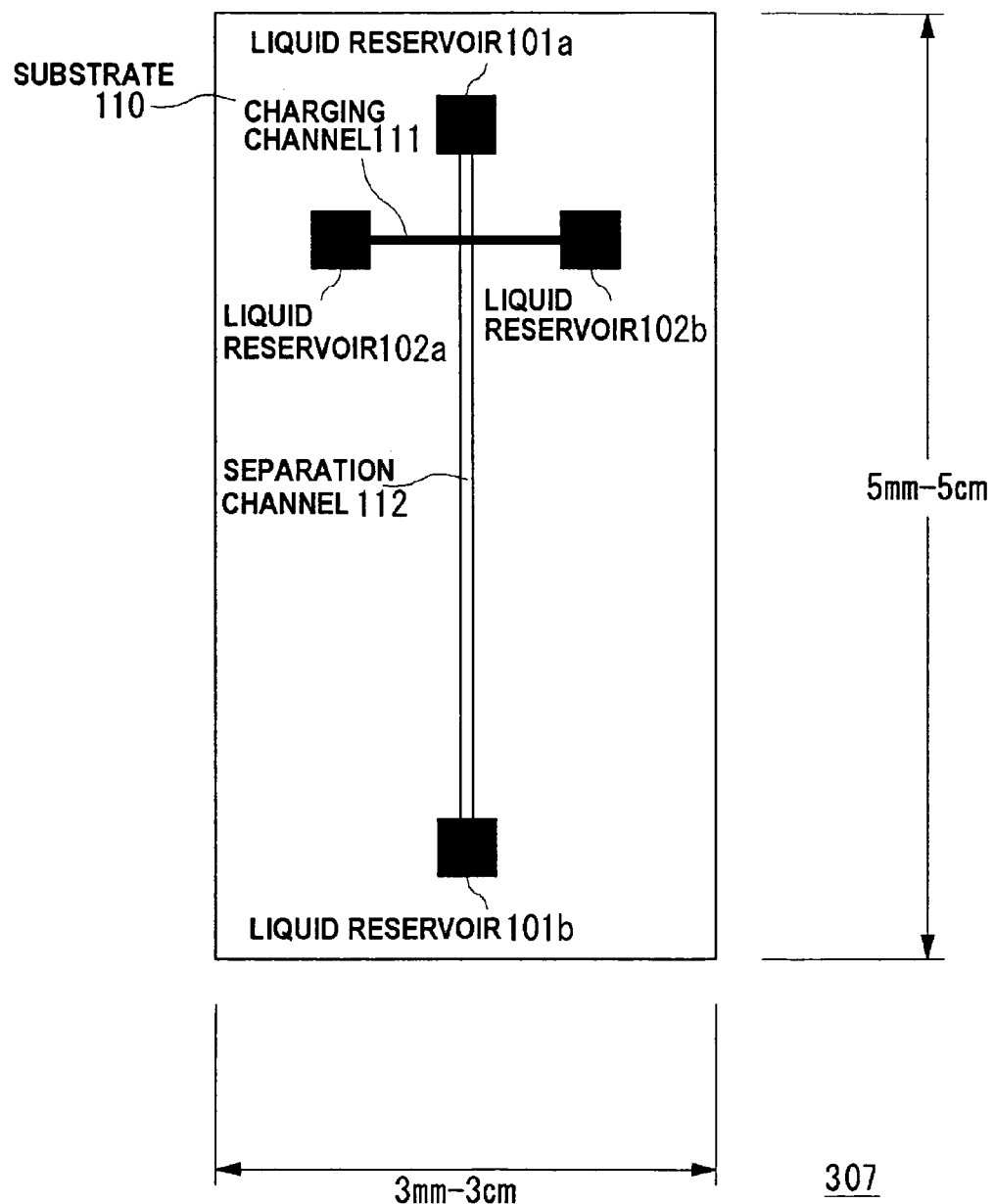
FIG. 21 is a view showing a configuration of the microchip used for the mass spectrometry system of FIG. 1.

In the mass spectrometry system of FIG. 1, the microchip 353 may be configured to have the plural channels intersecting one another. FIG. 21 is a view showing the configuration of the microchip 307 which can be applied to the mass spectrometry system 351.

Similarly to the microchip 307 of FIG. 3, in FIG. 21, the separation channel 112 is also formed in the substrate 110. An charging channel 111 is formed so as to intersect the separation channel 112. Liquid reservoirs 101a and 101b and liquid reservoirs 102a and 102b are formed at the both ends of the separation channel 111 and the charging channel 112. The electrode (not shown) is provided in each liquid reservoir, and the voltage can be applied to the both ends of the separation channel 112 in the same way as the first embodiment. Appropriate values are selected as the outside dimensions of the microchip 307 according to the application. Usually, as shown in FIG. 21, the longitudinal value ranges 5 mm to 5 cm and the transverse value ranges from 3 mm to 3 cm.

When the separation is performed with the microchip 307 of FIG. 21, the sample is injected in the liquid reservoir 102a or the liquid reservoir 102b. When injected in the liquid reservoir 102a, the voltage is applied such that the sample flows toward the direction of the liquid reservoir 102a, and when injected in the liquid reservoir 102b, the voltage is applied such that the sample flows toward the direction of the liquid reservoir 102b. Such configuration allows the sample to flow into the charging channel 111. As a result, the charging channel 111 is filled with the sample. At this point, in the separation channel 112, the sample exists only at an intersection point between the charging channel 111 and the separation channel 112, the sample forms the narrow band having the width of the charging channel 111.

Then, the voltage application between the liquid reservoir 102a and the liquid reservoir 102b is stopped, and the voltage is applied between the liquid reservoir 101a and the liquid reservoir 101b such that the sample flows toward the direction of the liquid reservoir 101b, which allows the sample to pass through the separation channel 112. During this time, the sample goes through the separation channel 112 at speed according to the molecular size, the charge intensity, and the interval between the columnar bodies. Thus, similarly to the microchip 307 of FIG. 3, in the microchip 307 of FIG. 21, the voltage is applied to the both ends of the separation channel 112, which allows the sample to be moved in the separation channel 112.

Figure 22:
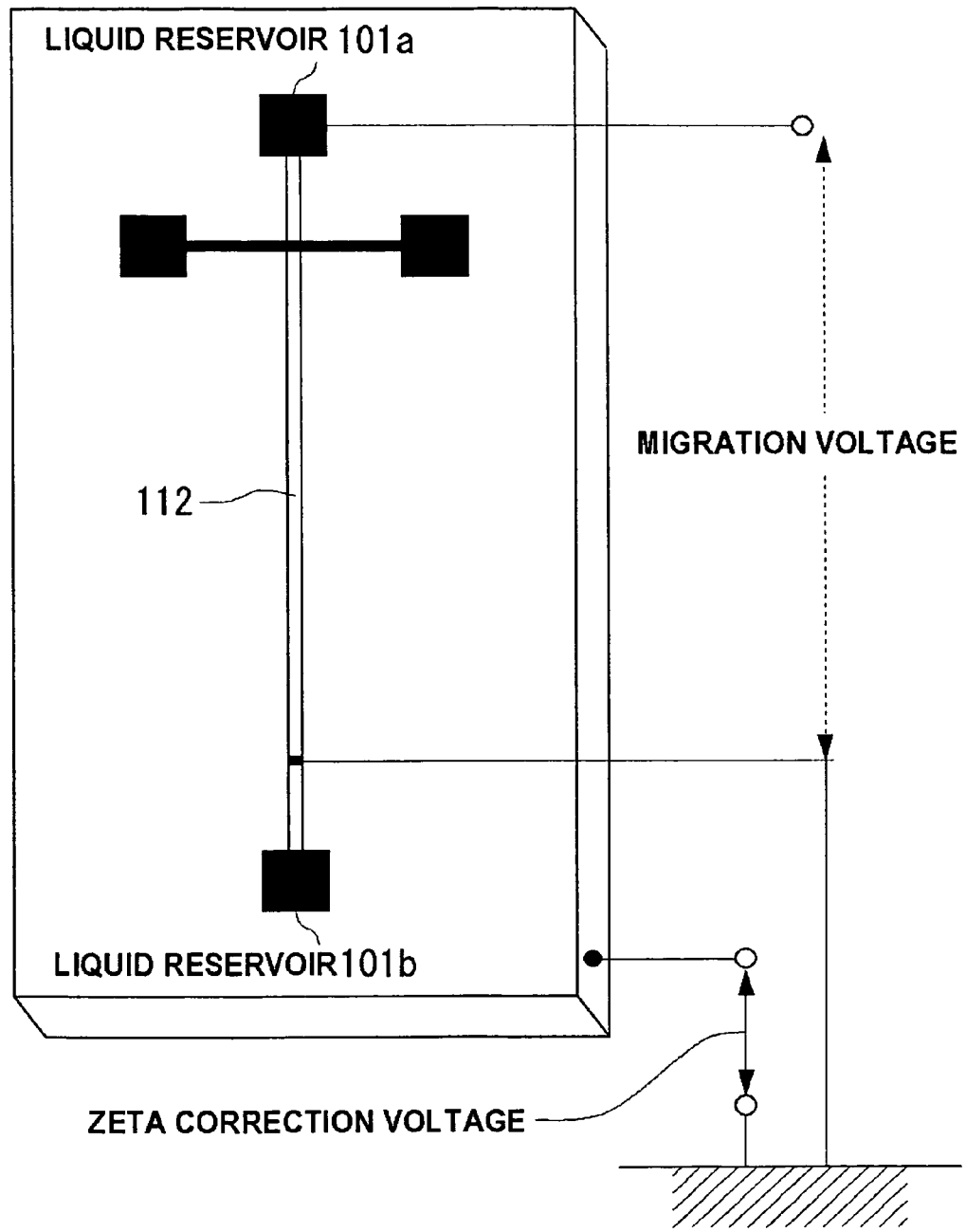
FIG. 22 is a view showing a method of applying correction voltage for adjusting electro-osmotic current.

As a result, the different molecular groups in the sample are separated in the bands which are moved at different speeds. At this point, in addition to the voltage for imparting the external force to the sample, the voltage for suppressing electroendosmotic flow may be applied. Referring to FIG. 22, for the purpose of the suppression of the electroendosmotic flow, zeta correction voltage is applied to the substrate. Accordingly, the electroendosmotic flow can be suppressed to effectively prevent a measurement peak from broadening.

In FIG. 21, the separation channel 112 is orthogonal to the charging channel 111. However, the angle between the separation channel 112 and the charging channel 111 is not limited. For example, the same effect is obtained, even if the configuration in which the separation channel 112 and the charging channel 111 intersect at an angle of 45 degrees is adopted.

After the sample is separated with the microchip 307 of FIG. 21, as with the first embodiment, the separated bands are ionized by irradiating the sample with the laser beam along the extending direction of the separation channel 112.

Third Embodiment

Figure 23:
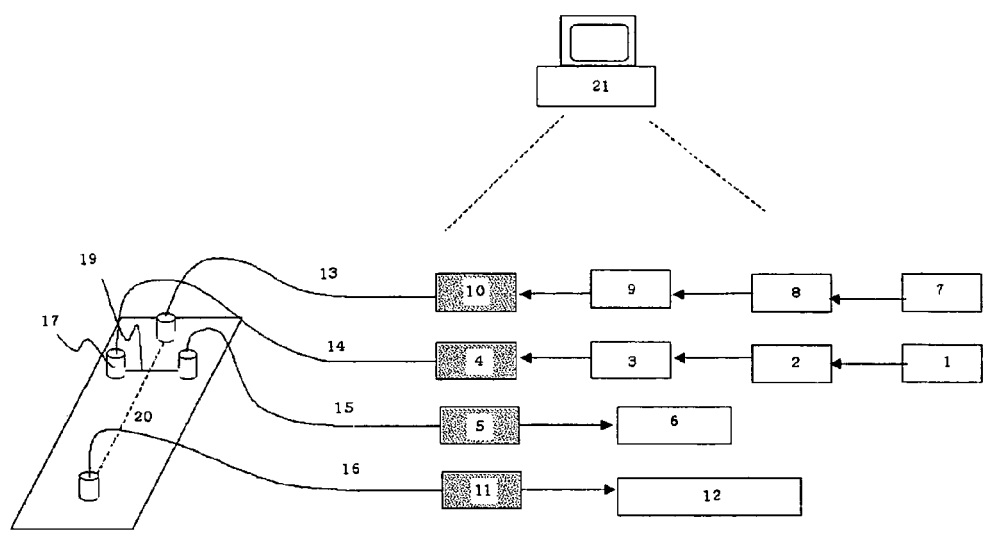
FIG. 23 is a view showing a configuration of the microchip used for the mass spectrometry system of FIG. 1.
Figure 24:
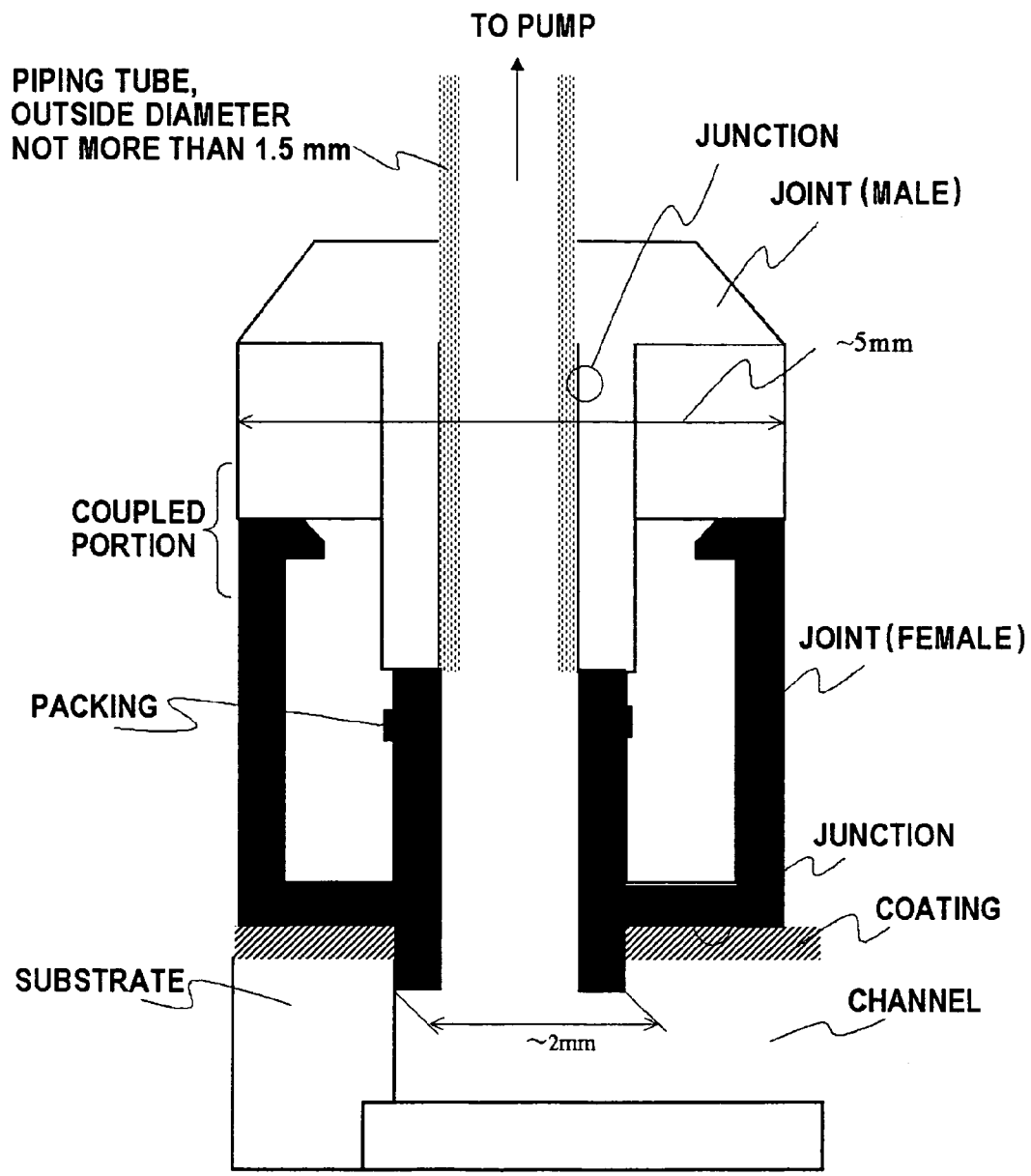
FIG. 24 is a view showing a specific configuration of a joint user for the microchip.

The method of moving the sample by applying the voltage is adopted in the microchip 307 described in the first embodiment and the second embodiment. The method of applying the pressure can also be adopted instead of the voltage. FIG. 23 shows an example of the microchip adopting the pressure applying method. Referring to FIG. 23, in the separation chip, female joints are fixed to liquid reservoir portions are located on the ends of a charging channel 19 and a separation channel 20. Male joints, which are coupled to a hollow tube 13, tubes 14 to 16, are connected to the female joints respectively. The reason why the joints 17 are used is to prevent liquid leakage is prevented. For example, FIG. 24 shows the specific configuration of the joint 17.

The tubes connected to the male joints are coupled to solenoid valves 10, 4, 5, 11 respectively. The buffer solution is supplied from a liquid reservoir 7 to the solenoid valve 10 through a separation pump 8 and a constant-rate injector 9. The sample delivered through a separation channel 20 is supplied to the solenoid valve 11, and the sample is introduced to a waste liquid reservoir 12. The sample is supplied from a sample reservoir 1 to the solenoid valve 4 through an charging pump 2 and a constant-rate injector 3. The sample delivered through an charging channel 19 is supplied to the solenoid valve 5, and the sample is introduced to a waste liquid reservoir 6.

A control unit 21 controls operating points of the solenoid valves 4, 5, 10, and 11, separation pump 8, the charging pump 2, and the constant-rate injectors 9 and 3.

The separation procedure with the apparatus shown in FIG. 23 will be described below. First the solenoid valves 10 and 11 are closed, which allows the sample to be prevented from flowing into the separation channel 20 from the charging channel 19. Then, the solenoid valves 4 and 5 are opened, and the sample is inputted to the sample reservoir 1.

Next, the charging pump 2 pressurizes the sample and introduces the sample to the charging channel 19 through the constant-rate injector 3, the solenoid valve 4, and the tube 14. The sample which leaks through the charging channel 19 is introduced to the waste liquid reservoir 6 through the tube 15 and the solenoid valve 5.

After the charging channel 19 is filled with the sample, the solenoid valves 4 and 5 are closed and the solenoid valves 10 and 11 are opened. Then, the separation pump 8 pressurizes the buffer solution to introduce the sample to the separation channel 20 through the constant-rate injector 9, the solenoid valve 10, and the tube 13. Thus, the separation operation is performed. In the configuration, since the pressure is utilized as the external force for moving the sample, the pressure is generated only by providing the relatively simple external force imparting device. Therefore, it becomes advantageous in production cost reduction and down-sizing of the apparatus.

The microchip of the third embodiment can also preferably be applied as the microchip 353 to the mass spectrometry system 351 shown in FIG. 1.

Fourth Embodiment

This embodiment has another configuration of the microchip 353 used for the mass spectrometry system 351 of FIG. 1. In the case where the separation channel 112 is configured as shown in FIG. 8 in the microchip 353, sometimes clogging occurs when the sample includes the gigantic-size substance. Once the clogging occurs, usually it is difficult to eliminate the clogging.

When the sample containing the many kinds of substances having the small molecular sizes is separated by the high separation ability, the clogging problem becomes significant. In order to separate the sample containing the many kinds of substances having the small molecular sizes by the high separation ability, it is necessary to decrease the interval between pillars 125 to some extent. However, in this case, the large-size molecule is easy to generate the clogging.

Figure 25:
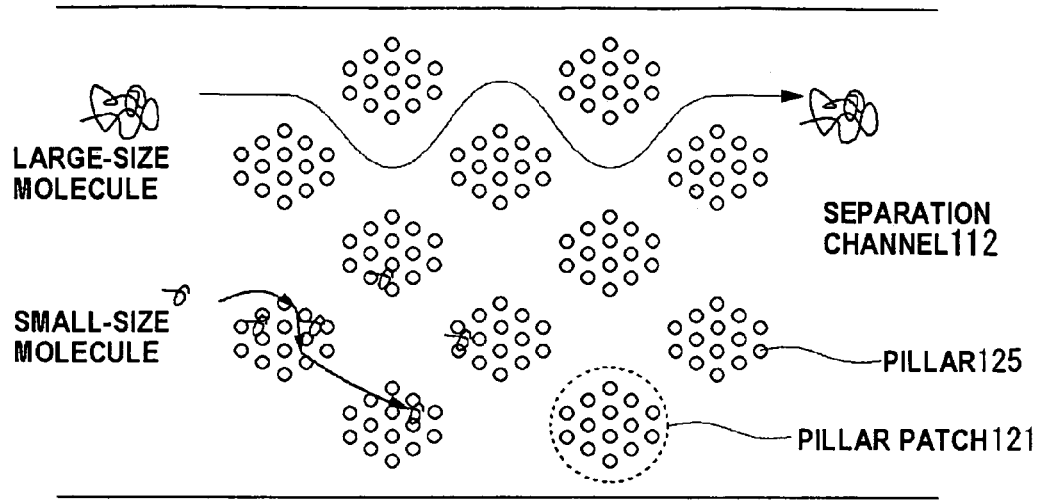
FIG. 25 is a view for explaining the sample separation method.

On the contrary, the clogging problem is solved in the separation method shown in FIG. 25. In FIG. 25, the plural columnar body arrangement portions (pillar patches 121) are formed in the separation channel 112 while separated from one another. In each columnar body arrangement portion, the pillars 125 having the same dimension are arranged at even intervals. The large molecule passes through the separation channel 112 before the small molecule. As the molecular size is decreased, the molecule is trapped in the separation area and passes through the longer path. On the other hand, the large-size substance passes smoothly through the path between the adjacent pillar patches 121.

As a result, the separation is performed such that the small-size substance is discharged after the large-size substance. Since the large-size substance passes relatively smoothly through the separation area, the clogging problem is decreased to remarkably improve the throughput. In order to exhibit the effect more remarkably, it is preferable that the width of the path between the adjacent pillar patches 121 is larger than the interval between the pillars 125 in the pillar patch 121. The width of the path is preferably 2 to 20 times the interval between the pillars 125, and more preferably 5 to 10 times the interval between the pillars 125.

For example, the separation channel 112 having the plural columnar body arrangement portions can be produced in the following manner. FIGS. 26 and 27 are a view showing a process of producing the channel in the microchip according to this embodiment. The silicon substrate 201 in these drawings is used as the substrate 110.

As shown in FIG. 26(a), the silicon oxide film 202 having the film thickness of 35 nm is formed on the silicon substrate 201. The calix-arene electron beam negative resist having the film thickness of 55 nm is formed, and the array area which becomes the sample channel is exposed by the electron beam (EB). The development can be performed with xylene, and the rinsing can be performed with isopropyl alcohol. As shown in FIG. 26(b), the resist 204 which is patterned is obtained through the process.

Then, the RIE etching of the silicon oxide film 202 is performed by using the mixture gas of $CF_4$ and $CHF_3$ (FIG. 26(c)). The resist is removed by the organic washing with the mixture solution of acetone, alcohol, and water, the oxidation plasma treatment is performed, and the ECR etching of the silicon substrate 201 is performed with HBr gas and oxygen gas (FIG. 27(d)). The silicon oxide film 202 is removed by performing the wet etching with BHF buffered hydrofluoric acid. The substrate obtained through the above processes is put into the furnace to form the silicon thermal oxide film 209 (FIG. 27(e)). Thus, the channel having the plural columnar body arrangement portions is obtained.

As with the first embodiment, in the fourth embodiment, the columnar bodies can be arranged at different intervals in the columnar body arrangement portion.

As shown in FIG. 28(a), it is possible to adopt the columnar body arrangement portion in which the interval between the pillars is decreased toward the flow direction. In this case, accumulation density of the columnar body is increased on the downstream side of the channel, and moving speed is decreased as the molecule which enters the columnar body arrangement portion is moved, so that a difference in holding time between the molecule which enters the columnar body arrangement portion and the large molecule which cannot enter the columnar body arrangement portion becomes significant. As a result, the improvement of the separation ability is realized. On the other hand, as shown in FIG. 28(b), it is possible to adopt the columnar body arrangement portion in which the interval between the pillars is increased toward the flow direction. Accordingly, the accumulation density of the columnar body is decreased on the downstream side of the channel, which allows the clogging to be suppressed in the columnar body arrangement portion. Therefore, the improvement of the throughput can be achieved. The mode in which the interval between the pillars is increased or decreased toward the flow direction can be applied to the separation area which does not have the columnar body arrangement portion.

Figure 29:
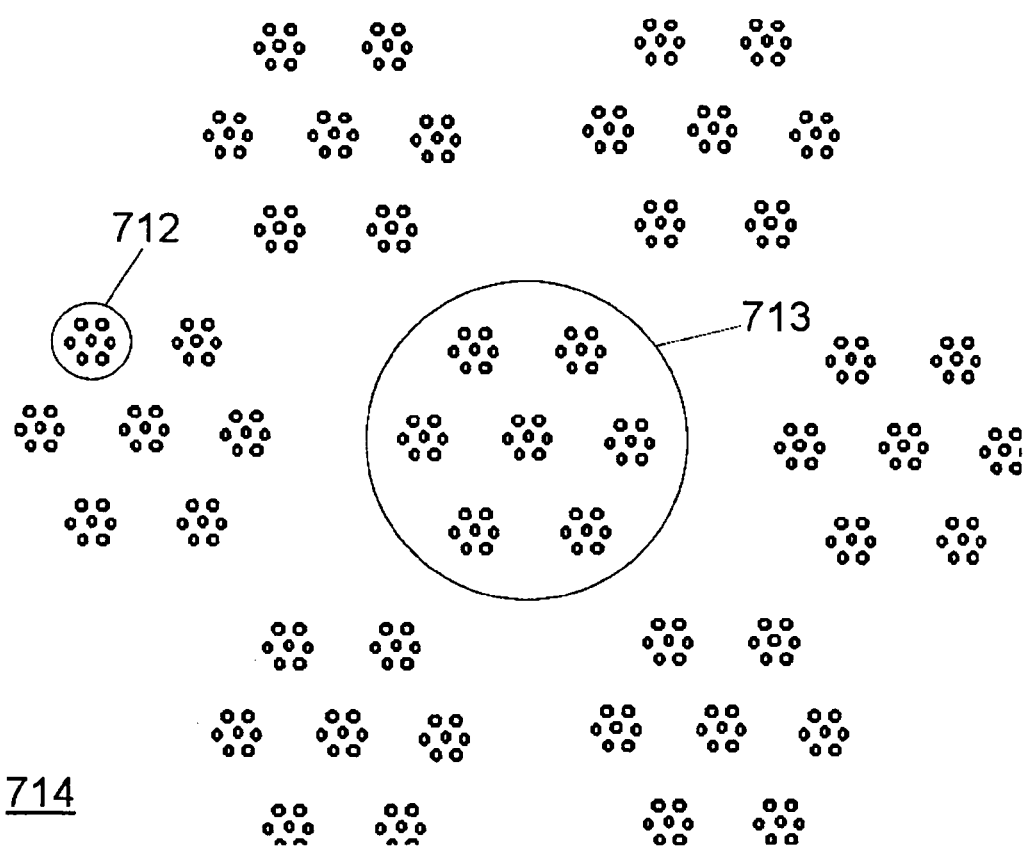
FIG. 29 is a view showing an example of the columnar body arrangement method.

It is also possible to make a hierarchical arrangement, in which the large columnar body arrangement portion is further formed by collecting the plural columnar body arrangement portions and the interval between the large columnar body arrangement portions is wider than the interval between the original columnar body arrangement portions. FIG. 29 shows an example of the hierarchical arrangement. A medium patch 713 is formed by collecting seven small pillar patches 712, and a large pillar patch 714 is formed by collecting the seven medium pillar patches 713. Thus, the columnar body arrangement portions are formed in the hierarchical manner, which allows the molecules having the various sizes to be simultaneously separated in the descending order of the size. That is, while the larger molecule passes between the larger columnar body arrangement portions, the medium-size molecule is trapped inside the medium-dimension columnar body arrangement portion and separated. Further, the small molecule is trapped inside the small columnar body arrangement portion and separated. As the molecular size is decreased, it takes longer time for the molecule to flow out. Therefore, the plural molecules having the different sizes can be separated in the descending order of the size.

Figure 30:
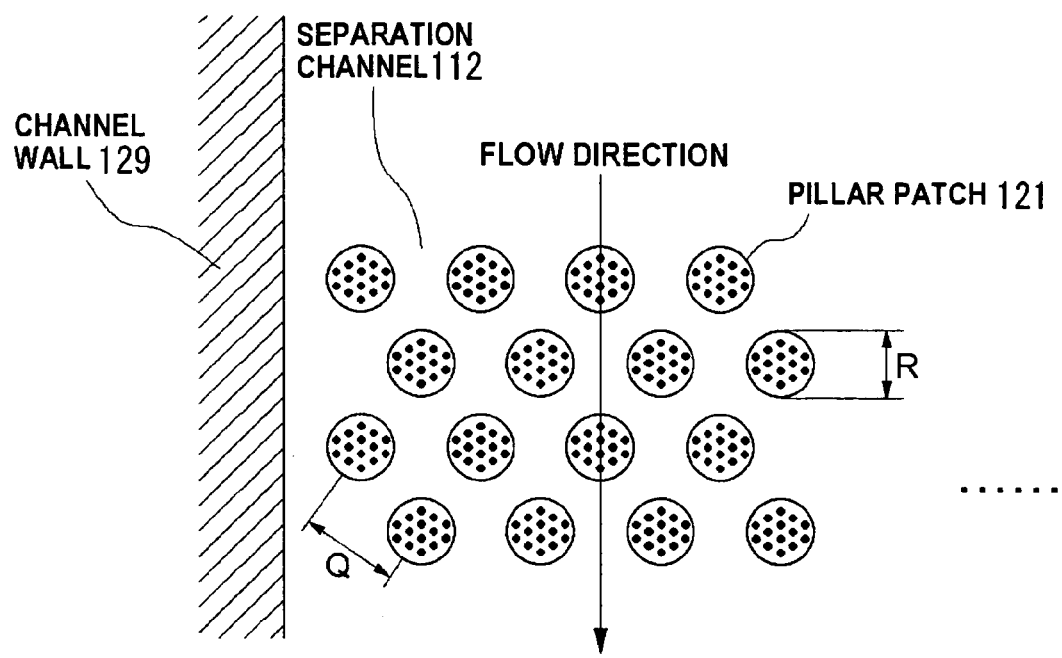
FIG. 30 is a plan view showing an arrangement of a pillar patch.

The structure of the sample separation area which realizes the separation method shown in FIG. 25 will be described with reference to FIG. 30. As shown in FIG. 30, the sample separation area has the structure in which the pillar patches 121 are arranged at even intervals in the space surrounded by channel wall 129. The pillar patch 121 includes the many pillars. In this case, a width R of the pillar patch 121 is set at values 10 μm or less, and an interval Q between the pillar patches 121 is set at values 20 μm or less.

Figure 31:
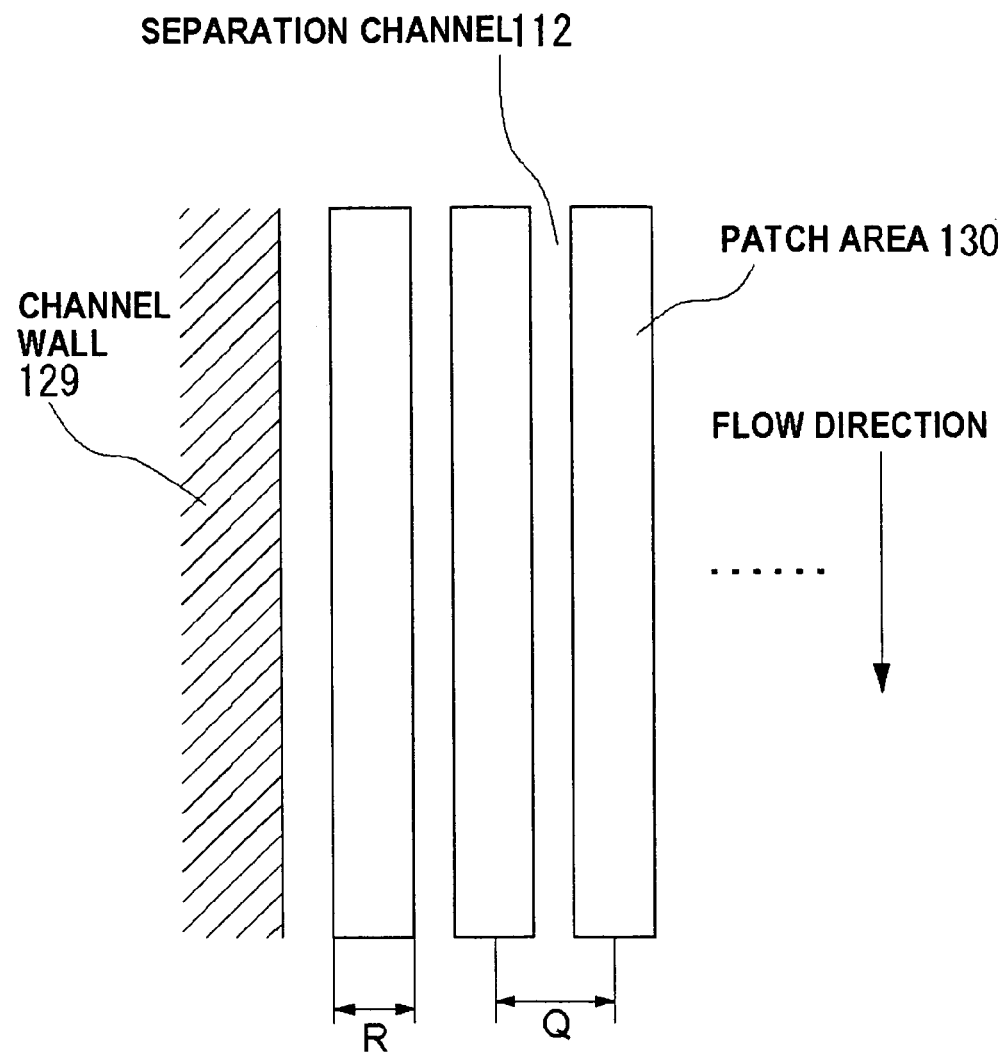
FIG. 31 is a plan view showing an arrangement of a pillar patch.

In FIG. 25, the pillar patch 121 formed by the dense pillars is formed in the circular area when viewed from the top surface. However, the shape of the pillar patch is not limited to the circle, but other shapes may be applied. In an example of FIG. 31, patch areas 130 are formed in the stripe shape when viewed from the top surface. In this mode, the width R of the patch area 130 is set at values 10 μm or less, and the interval Q between the patch areas 130 ranges from 10 to 100 μm.

Figure 32:
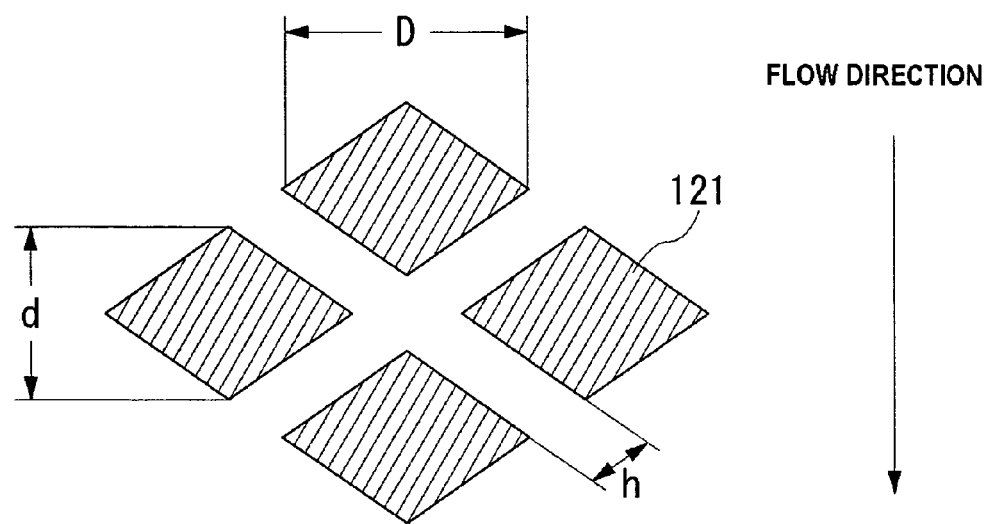
FIG. 32 is a view showing an example of the columnar body arrangement method.

FIG. 32 shows an example in which the plural rhombic pillar patches 121 are arranged in a rhombus. In this case, a constant angle is formed by the path and the flow direction to increase the contact frequency between the molecule and the pillar patch 121, which increases a probability that the molecule smaller than the interval between the pillars constituting the pillar patch 121 is trapped by the pillar patch 121. Therefore, the difference in holding time between the molecule trapped by the pillar patch 121 and the larger molecule which is not trapped by the pillar patch 121 becomes significant, which allows the separation ability to be improved. When R is the diameter of the target molecule of the separation, it is preferable that an interval h between the pillar patches, diagonal lines D and d of the pillar patch 121 and an interval p between the pillars constituting the pillar patch satisfies the following conditions. Accordingly, the target molecule can be separated with high accuracy.

h: $R \leq h < 10R$,
p: $0.5R \leq p < 2R$,
D: $5h \leq D < 20h$,
d: $5h \leq d < 20h$.

The constituent forming the patch area is not limited to the pillar. For example, it is also possible to form the patch area in which plate-shaped members are arranged at even intervals. FIG. 33 shows an example. FIG. 33(a) is a top view, and FIG. 33(b) is a sectional view taken on line A-A' of FIG. 33(a). The patch areas are arranged as shown in FIG. 33(c). Once the molecule is trapped in the patch area 130, the molecule resides in the patch area 130 until the molecule escapes to the separation channel 112. The difference in holding time between the molecule trapped by the patch area and the molecule which is not trapped by the patch area becomes significant, which improves the separation ability. When R is the diameter of the target molecule of the separation, it is preferable that an interval Λ between the patch areas 130 and an interval λ between the plate-shaped members constituting the patch area 130 satisfies the following conditions. Accordingly, the target molecule can be separated with high accuracy.

Λ: $R \leqq \Lambda < 10R$,
λ: $0.5R \leqq \lambda < 2R$.

The columnar body or the top portion of the plate-shaped member may be in contact with the upper surface of the channel or separated from the upper surface of the channel. When the columnar body or the top portion of the plate-shaped member is separated from the upper surface of the channel, there is a gap between the columnar body or the top portion of the plate-shaped member and the upper surface of the channel, so that passing opportunity of the large molecule is increased. Therefore, the clogging problem can further be solved. For the small molecule, the opportunity in which the small molecule enters the patch area from above through the gap is increased, so that the separation effect is further improved. The above mode can easily be realized by previously providing the groove portion in the member (cover glass and the like) which becomes the upper surface of the channel or by making the heights of columnar body and the plate-shaped member lower than the depth of the channel.

The width of the path between columnar body arrangement portions and the interval between the columnar bodies in the columnar body arrangement portion are appropriately selected according to the component to be separated, e.g. the organic molecule such as nucleic acid, amino acid, peptide, and protein or the molecule and ion such as chelated metal. For example, it is preferable that the interval between the columnar bodies is substantially equal to an inertia radius corresponding to a median of the dimensions of the molecular groups to be separated or the interval is slightly smaller or larger than the inertia radius. Specifically, the difference between the inertia radius corresponding to the median and the interval between the columnar bodies is set at values 100 nm or less, more preferably 10 nm or less, and most preferably 1 nm or less. The separation ability is further improved by appropriately setting the interval between the columnar bodies.

It is preferable that the interval (width of path) between the adjacent columnar body arrangement portions is equal to the inertia radius of the molecule contained in the sample or the interval is slightly smaller or larger than the inertia radius. Specifically, the difference between the inertia radius of the molecule contained in the sample and the interval between the columnar body arrangement portions is set within 10% of the inertia radius of the molecule, more preferably within 5%, and most preferably within 1%. When the interval between the columnar body arrangement portions is too widened, sometimes the separation of the small-size molecule is not sufficiently performed. When the interval between the columnar body arrangement portions is too narrowed, sometimes the clogging is easy to occur.

Fifth Embodiment

In the microchip used as the microchip 353 of FIG. 1, specifically, in the microchip 307 shown in FIG. 21, the columnar bodies may be arranged in one line or plural lines on the upstream side of the separation area provided in the separation channel 112, namely on the side to which the sample is introduced. FIG. 34 shows an example. As shown in FIG. 34(a), one pillar row 710 is arranged in front of a separation area 711 provided in the channel. The interval between the pillars in the pillar row 710 is configured to be substantially equal to the minimum-size molecule included in the molecular group 709 of the separation target. The following effects are obtained by adopting the above configuration. The separation area 711 may be formed by providing the patch area or the columnar body arrangement portion, or the separation area 711 may be formed by uniformly providing the columnar bodies.

In FIG. 34(a), when the weak drive force (for example, extremely weak electric field) is imparted to the separation target molecular group 709, the separation target molecular group 709 which diffuses widely is moved in the channel and when it reaches the pillar row 710, it is dammed, so that it forms the thin band in the narrow band-shaped area adjacent to the pillar row 710 (FIG. 34(b)).

Then, the separation target molecular group passes through the pillar row while holding the thin band state by temporarily imparting the strong drive force (for example, strong electric field) to the molecular group (FIG. 34(c)). That is, in the case of the macromolecule such as DNA and protein, even if the molecular size is larger than the interval between the pillars, the molecule can scrape through the interval between the pillars by the molecular extension when the pillar row is formed in one or several lines (reptation effect).

After the separation target molecular group passes through the pillar row, the drive force suitable for the separation is imparted to the molecular group, which allows the separation to be effectively performed (FIG. 34(d)). Because the molecular group holds the thin band state as described above, the peak overlap is decreased after the separation, which allows the separation to be realized with high accuracy.

In the case where the columnar body row is applied to the configuration described in the fourth embodiment, for example, it is also possible to for the configuration in which the pillar row 710 shown in FIG. 34 is provided in front of the separation area having the columnar body arrangement portion shown in FIG. 28(a).

Sixth Embodiment

Figure 35:
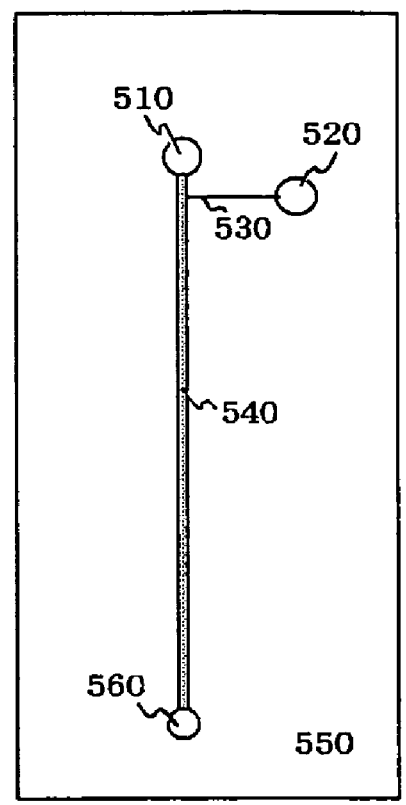
FIG. 35 is a view showing a configuration of the microchip used for a mass spectrometry system according to an embodiment.

This embodiment is another configuration of the microchip which can be applied to the mass spectrometry system 351 of FIG. 1. In this embodiment, the sample is separated by utilizing capillarity. FIG. 35 is a view showing the configuration of the microchip according to this embodiment. Separation pillars (not shown) are arranged in a separation channel 540 formed in the substrate 550. The material of the substrate 550 and the configuration of the separation pillars can be formed in the same way as for the first to fifth embodiments. An air hole 560 is made at one end of the separation channel 540, and a buffer inlet 510 is provided at the other end. The buffer inlet 510 injects the buffer solution during the separation. The separation channel 540 is sealed except for the portions of the buffer inlet 510 and air hole 560. A sample metering pipe 530 is connected to a start portion of the separation channel 540, and a sample inlet 520 is provided at the other end of the sample metering pipe 530.

Metering pillars (not shown) are arranged in the sample metering pipe 530. The metering pillars are arranged less densely than the separation pillars, and the sample separation never occurs in the metering pillars. The sample metering pipe 530 is sealed except for the portion of the sample inlet 520.

Figure 36:
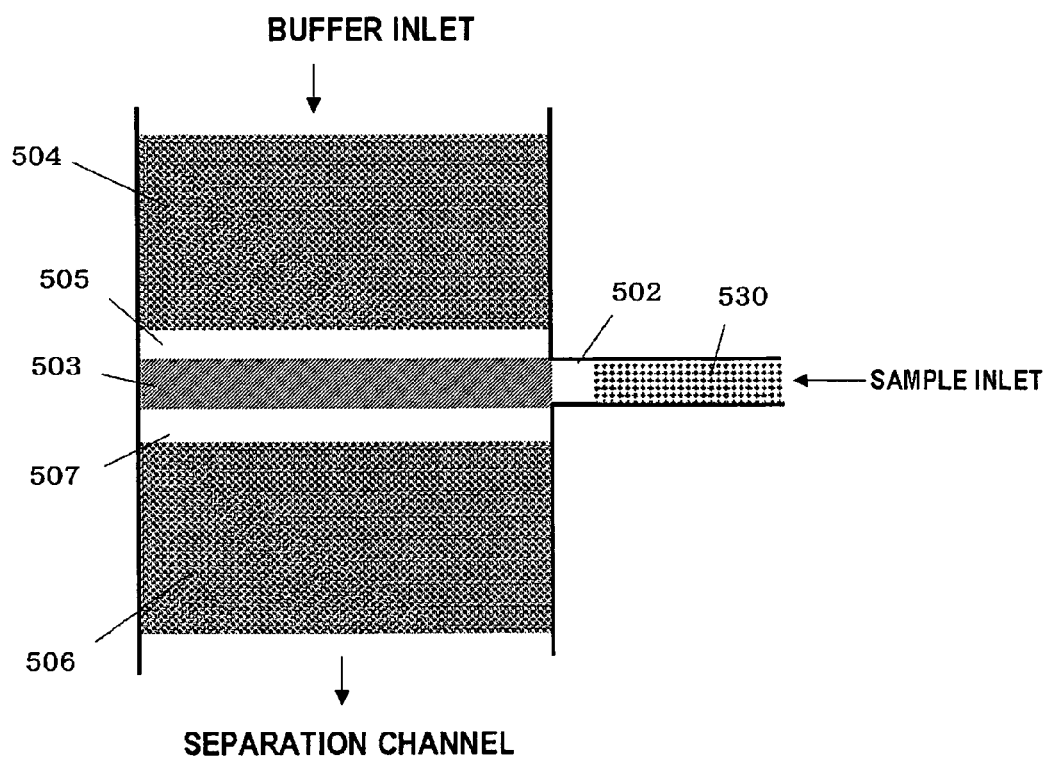
FIG. 36 is a view showing a configuration of the microchip used for a mass spectrometry system according to an embodiment.

FIG. 36 is an enlarged view showing the surroundings of the sample metering pipe 530 shown in FIG. 35. The metering pillars in the sample metering pipe 530 and a sample holder portion 503 is partitioned by a temporary stop slit 502. In the sample holder portion 503 are arranged pillars (not shown) denser than the pillars arranged in a buffer introduction portion 504 and a separation portion 506. The pillars (not shown), collected to the same extent as the separation pillar, are arranged in the buffer introduction portion 504. The sample holder portion 503, the buffer introduction portion 504, and the separation portion 506 are partitioned by temporary stop slits 505 and 507. A cavity volume of the sample holder portion 503 is substantially equal to the sum of the cavity volume of the sample metering pipe 530 and the volume of the temporary stop slit 502. The width of the temporary stop slit 505 is narrower than that of the temporary stop slit 502.

Next, the separation operation procedure with the device of FIG. 35 will be described. The sample is gradually injected in the sample inlet 520 to fill the sample metering pipe 530 with the sample. At this point, the liquid level is adjusted so as not to rise. In the sample injection operation, the sample is held between the sample metering pillars arranged in the sample metering pipe 530. After the sample metering pipe 530 is filled with the sample, the sample seeps gradually to the temporary stop slit 502. When the sample seeping to the temporary stop slit 502 reaches the surface of the sample holder portion 503, all the amount of sample in the temporary stop slit 502 and the sample metering pipe 530 is absorbed to the sample holder portion 503 having the larger capillarity effect. The reason why the sample holder portion 503 is larger than the sample metering pipe 530 in the capillarity effect is that the pillars are densely formed and the sample holder portion 503 has the larger surface area. The sample never flows into the buffer introduction portion 504 or the separation portion 506 in filling the sample holder portion 503 with the sample because the temporary stop slits 505 and 507 exist.

After the sample is introduced in the sample holder portion 503, the separation buffer solution is injected into the buffer inlet 510. The buffer introduction portion 504 is temporarily filled with the injected buffer solution, and an interface to the sample holder portion 503 becomes linear. When the buffer introduction portion 504 is further filled with the buffer solution, the buffer solution seeps to the temporary stop slit 505 and flows into the sample holder portion 503. Then, the buffer solution goes to the separation portion 506 across the temporary stop slit 507 while dragging the sample. At this point, the width of the temporary stop slit 502 is larger than the widths of the temporary stop slit 505 and 507. Therefore, even if the buffer solution flows back to the temporary stop slit 502, back flow of the little amount of sample occurs, because almost all the amount of sample already goes ahead of the sample holder portion 503.

The separation buffer solution further goes through the separation portion 506 toward the air hole by the capillary phenomenon, and the sample is separated through this process.

Figure 37:
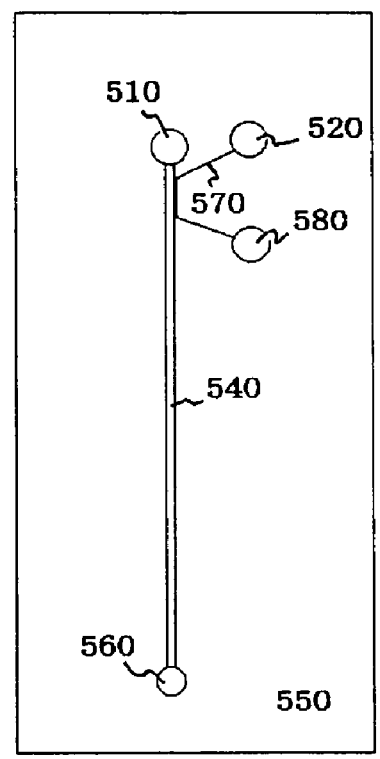
FIG. 37 is a view showing a configuration of the microchip used for a mass spectrometry system according to an embodiment.
Figure 38:
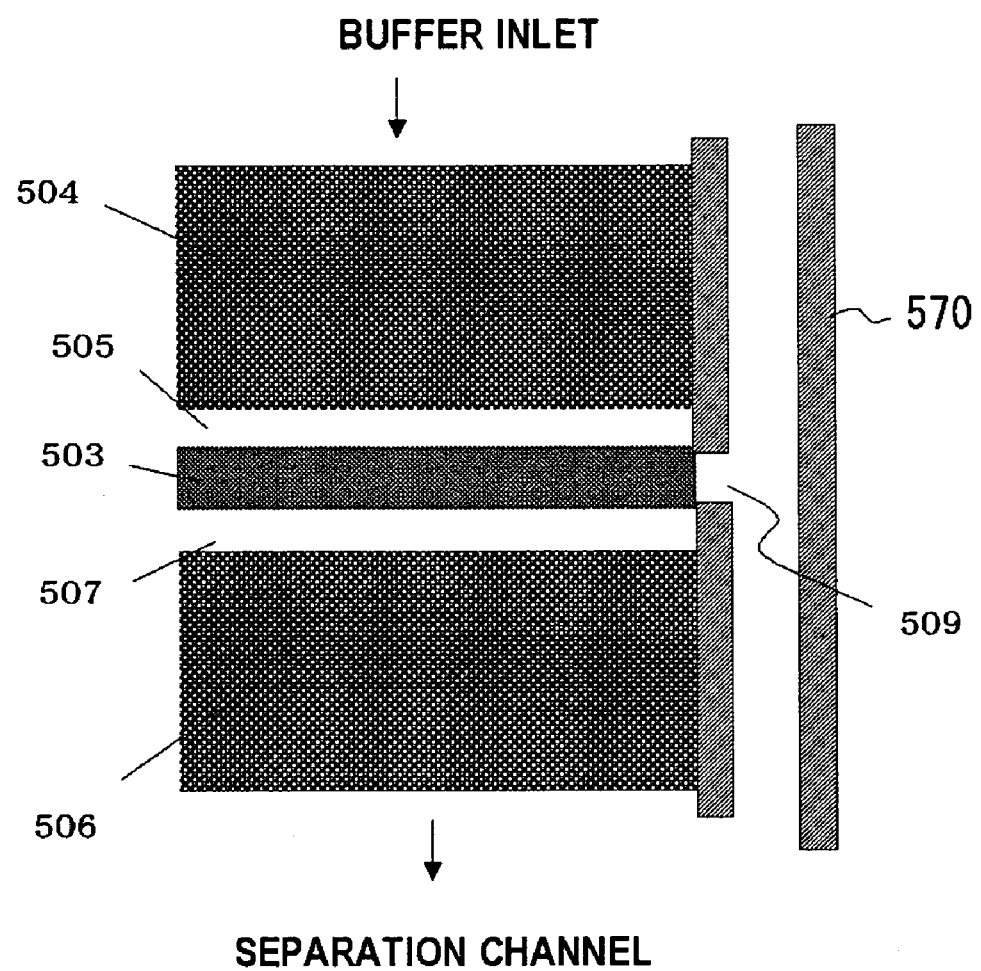
FIG. 38 is a view showing a configuration of the microchip used for a mass spectrometry system according to an embodiment.

Another example of the sample injection which utilizes the principle of the sample metering injection by the capillary phenomenon will be described with reference to FIGS. 37 and 38. In the device shown in FIGS. 37 and 38, a sample input pipe 570 is provided instead of the sample metering pipe 530 in FIG. 36. The sample inlet 520 and an outlet 580 are provided at the both ends of the sample input pipe 570. The pillars are not arranged inside the sample input pipe 570. The sample input pipe 570 is opened to the sample holder portion 503 through an input hole 509.

The separation procedure with this device will be described. The sample is inputted to the sample inlet 520 to fill the outlet 580. During this period, the sample is absorbed in the sample holder portion 503 through the input hole 509.

The air is injected in the sample inlet 520 to discharge the sample from the outlet 580, the sample is evacuated from the inside of the sample input pipe 570, and the inside of the sample input pipe 570 is dried. In the case of the separation by the capillarity, the separation buffer solution is injected as described above. In the case of the separation by the electrophoresis, the migration buffer solution is introduced to the liquid reservoir corresponding to the buffer inlet 510 and the liquid reservoir corresponding to the air hole 560 prior to the sample input. Because the widely-formed temporary stop slits 505 and 507 exist, the buffer solution does not flow into the sample holder portion 503.

At a stage in which the sample hold is ended in the sample holder portion 503, the extremely small amount of migration buffer solution is further added to the liquid reservoirs at one end of the separation channel, or vibration is lightly imparted to the surroundings of the sample holder portion 503, which allows the migration buffer solution to be continued. Therefore, the voltage is applied to perform the separation.

Thus, in the microchip of this embodiment, the sample can be separated by the capillary phenomenon. Therefore, it is not necessary to form the electrode on the substrate, so that the device configuration can be further simplified.

Seventh Embodiment

Figure 39:
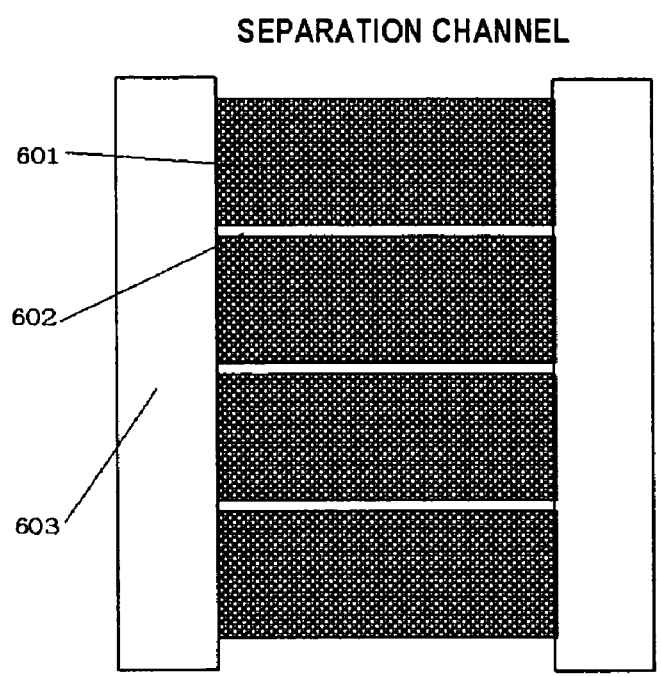
FIG. 39 is a view showing a configuration of the microchip used for a mass spectrometry system according to an embodiment.

This embodiment has another configuration of the microchip which can be applied to the mass spectrometry system 351 of FIG. 1. In this embodiment, the separation is performed by using the microchip, in which the separation area divided into the plural portions through slits is provided in the channel. FIG. 39 is a view showing the configuration of the channel in the microchip according to this embodiment. Referring to FIG. 39, a sample separation area 601 is formed in the channel so as to block up the channel. The sample separation area 601 is divided into the plural portions through slits 602. There is no gap between a wall 603 and the sample separation area 601. In the case where this configuration is adopted, the band shape of the separated sample becomes preferable, and the separation ability is improved. This point will be described with reference to FIG. 40.

Figure 40:
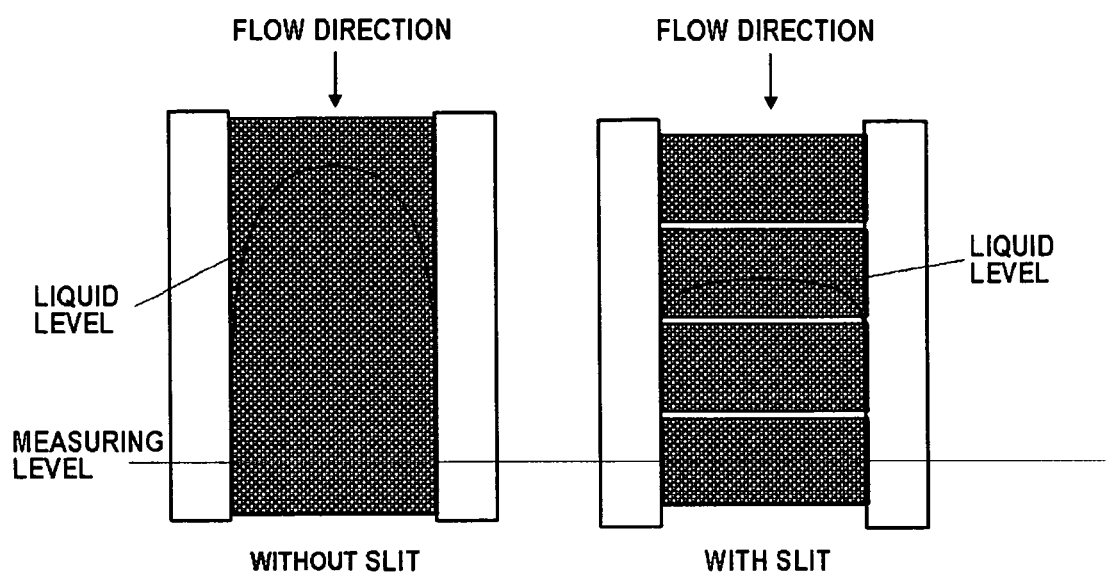
FIG. 40 is a view showing a configuration of the microchip used for a mass spectrometry system according to an embodiment.

When the single sample separation area 601 is provided with no slit, as shown in the left view of FIG. 40, the liquid level of the sample flowing from the upper portion to the lower portion becomes the curved surface. This is because the little effect of the capillarity acts on the central portion of the channel section while the sample movement is promoted by the capillarity in the portion along the wall. Since the sample flow speed is increased near the wall, the band shown in the drawing is formed. On the contrary, when the sample separation area 601 is divided into the plural portions through the slits 602, the liquid during the separation is temporarily held in the sample separation area above the slit due to the existence of the slit. Because the air exists in the slit, the liquid movement is started from the sample separation area to the slit when the pressure of the sample existing the sample separation area above the slit exceeds the pressure derived from the air in the slit.

Thus, since the liquid including the sample is temporarily held in the sample separation area, even if the difference in movement distance between the wall portion and the central portion is generated, the difference is eliminated during the time in which the liquid is held. As a result, at the stage in which the passage of the liquid through the slit is ended, the liquid level becomes the plane substantially perpendicular to the separation direction (right view of FIG. 40). Accordingly, the band perpendicular to the separation direction is formed to improve the separation ability. The configurations described in the first embodiment to the fourth embodiment can arbitrarily be adopted as the sample separation area 601. For example, the sample separation area in which the patch area or the columnar body arrangement portion is provided or the sample separation area in which the columnar bodies are uniformly arranged may be formed.

Figure 42:
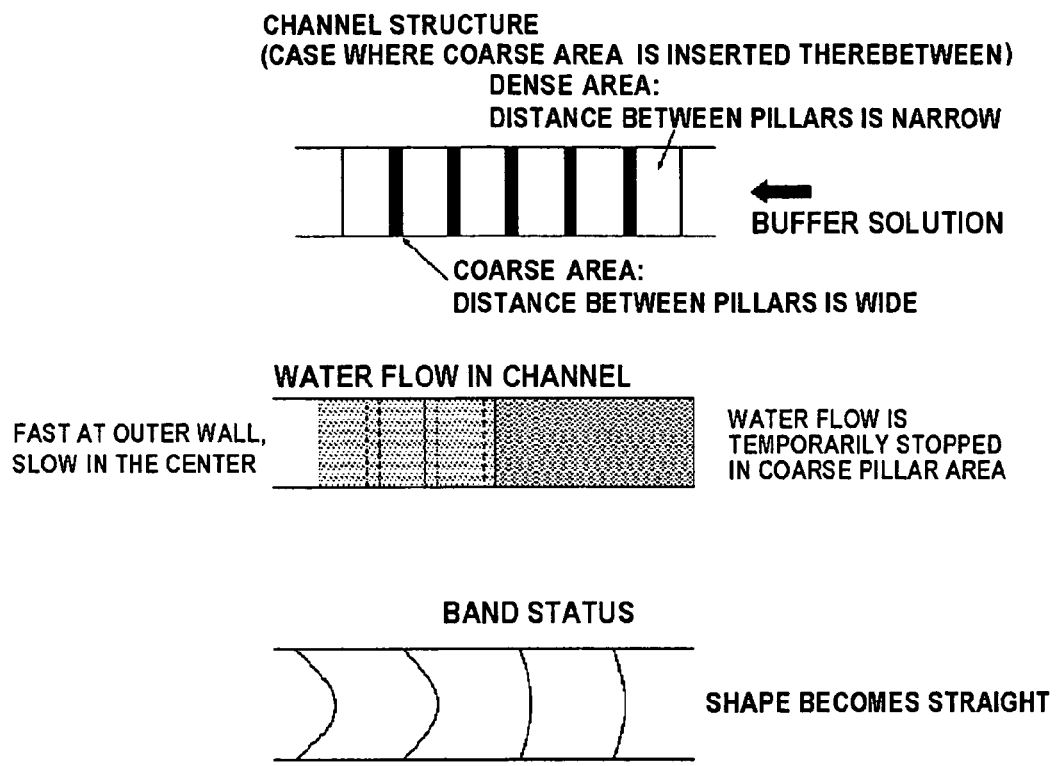
FIG. 42 is a view showing an example of a channel structure.

FIGS. 41 and 42 are a view showing the difference in band shape of the sample by the capillarity. As shown in FIG. 41, when single artificial gel which is conventionally used as the sample separation area is provided, the band shape becomes one in which is curved toward the sample progress direction. On the contrary, referring to FIG. 42, there is adopted the configuration, in which the area where the pillars are coarsely formed and the area where the pillars are densely formed are alternately formed. The area where the pillars are coarsely formed act as the slit in FIGS. 39 and 40. That is, the liquid including the sample is temporarily stopped just before the area where the pillars are coarsely formed, and the difference in movement distance of the liquid generated in the area where the pillars are densely formed is eliminated during this period, which results in the band shape of the substantial plane with respect to the sample progress direction.

Thus, the effect of the area where the slits and the pillars are coarsely formed is described in the case where the sample is introduced by the capillary phenomenon. In the case where the electric field is used for the sample movement, the same effect can also be obtained by providing the slits and the like. In the case of the separation by the electrophoresis, it is well known that the band is curved as the migration proceeds. The band shape can be adjusted by the slit and the like. In this case, even if the slit is filled with the buffer solution, the effect of the band shape adjustment can be obtained.

Eighth Embodiment

The mode, in which the sample is separated with the separation channel 112 in which the projections projected from the bottom surface toward the cannel are formed, is described in the above embodiment. However, the sample can also be separated with the separation channel 112 in which the concaves are formed instead of the projections.

The microchip having the separation channel 112 in which the concaves are formed will be described below. The microchip having the separation channel 112 in which the concaves are formed can also be applied to the mass spectrometry system 351 of FIG. 1. Because the basic configuration of the microchip can be formed in the same manner as for the above embodiments, the different configuration will mainly be described below.

The recess shaped as the circular cylinder, the elliptic cylinder, the circular cone and the elliptic cone can preferably be used, various shape such as the rectangle and the triangular pyramid can be adopted. The dimension of the concave is appropriately set according to the purpose of the separation. For example, in the processes of:

(i) The separation and the condensation of a cell and other components,
(ii) The separation and the condensation of a solid matter (fragment of cell membrane, mitochondria, and endoplasmic reticulum) and a liquid fraction (cytoplasm) in the components obtained by destroying the cell, and
(iii) The separation and the condensation of a high-molecular weight component (DNA, RNA, protein, and sugar chain) and a low-molecular weight component (steroid, glucose, and the like) in the liquid fraction component,
in the case of (i), the interval can be set in the range of 1 µm to 1 mm,
in the case of (ii), the interval can be set in the range of 100 nm to 10 µm, and
in the case of (iii), the interval can be set in the range of 1 nm to 1 µm.

The depth of the concave can appropriately be set according to the application. For example, the depth of the concave can be set in the range of 5 to 2000 nm. The interval between the adjacent concaves is set at values 200 nm or less, more preferably 100 nm or less, and further preferably 70 nm. The lower limit of the interval is not particularly limited. For example, the interval can be set at values 5 nm or more. The interval between the concaves should mean the distance between the center points of the concaves.

Figure 43:
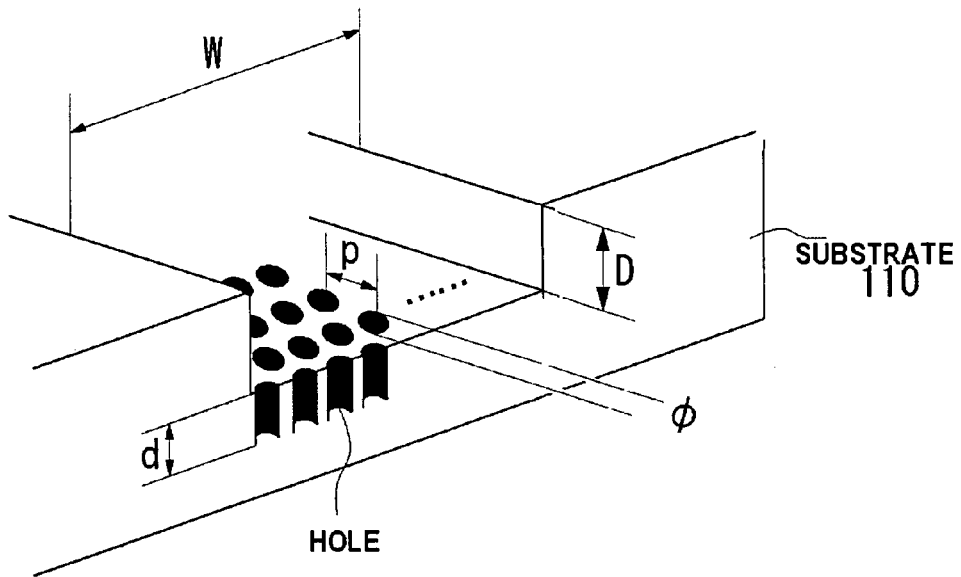
FIG. 43 is a view showing a detailed structure of the separation channel in FIG. 3.

FIG. 43 shows the detailed structure of the separation channel 112 in the microchip according to an eighth embodiment. Referring to FIG. 43, the groove portion having the width W and the depth D is formed in the substrate 110, and the cylindrical holes having the diameter $\phi$ and depth d are regularly formed at constant interval p in the bottom portion of the groove. For example, the width W of the channel, the depth D of the channel, the diameter $\phi$ of the hole, the depth d of the hole, and the interval p between the holes can be set at the dimensions shown in FIG. 43. In the later-mentioned modes shown in FIGS. 46, 47, 48, 49, and 52, W, D, $\phi$, d, and p can be set at the same dimensions.

Figure 44:
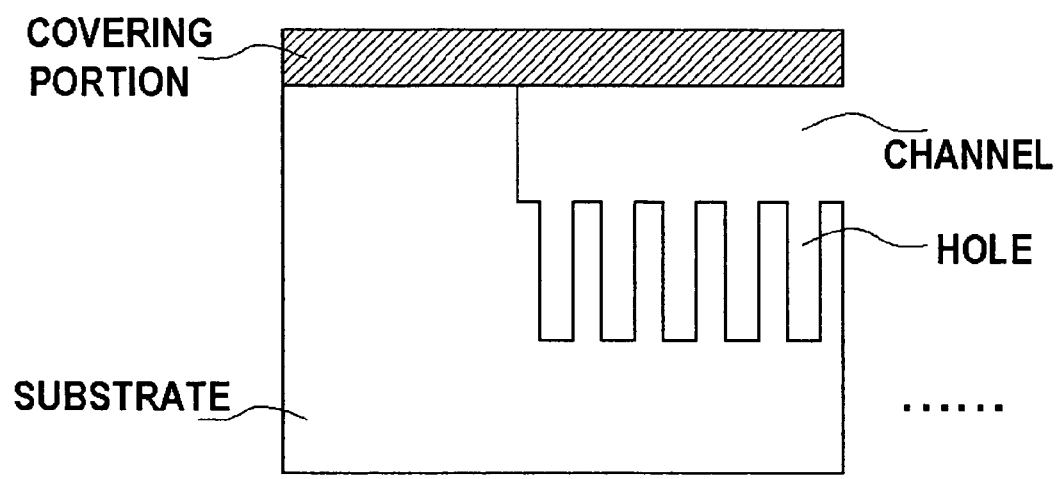
FIG. 44 is a view showing the detailed structure of the separation channel in FIG. 3.

The channel may be covered with a covering portion as shown in FIG. 44 during the separation. At this point, the channel formed in the substrate is sealed by the covering portion to form the space, and the sample is moved in the space. The covering portion performs the function of preventing the vaporization of water contained in the sample. In the later-mentioned embodiment with reference to FIG. 56, it is necessary that the electrode is provided above the channel, so that the covering portion having the transparent electrode is required as a part of the constituents in the sample separation.

Figure 45:
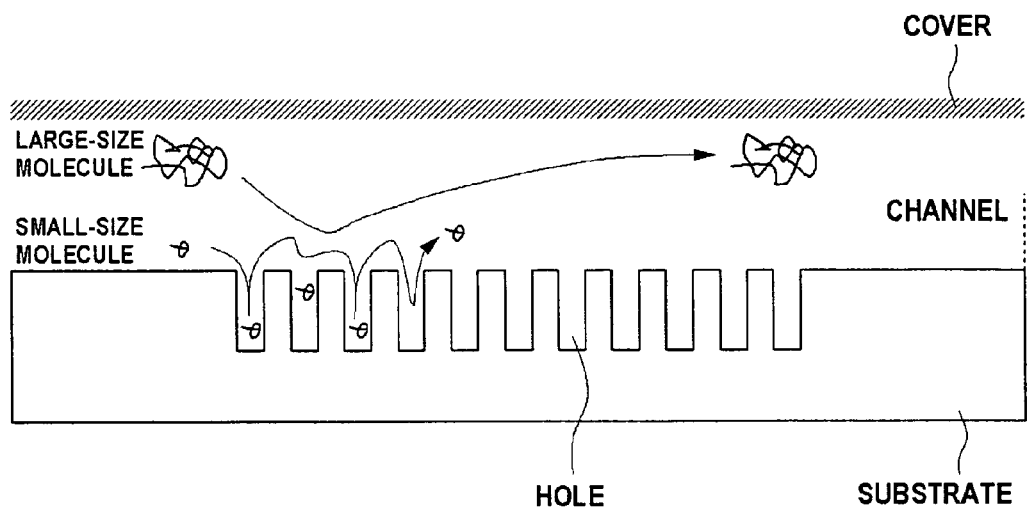
FIG. 45 is a view for explaining the sample separation method.

Then, the reason why the structure in which the many holes are made functions as the sample separation unit will be described with reference to FIG. 45. Referring to FIG. 45, the plural hole portions are made at predetermined intervals in the sample separation area. When the molecule having the size larger than the hole diameter passes through this area, the molecule is not trapped by the hole, but directly passes through the channel. Therefore, the molecule passes through this area at short times. On the other hand, the small-size molecule is trapped by the hole made in the substrate to pass through the long path. As a result, the sample is separated while the small-size substance is discharged after the large-size substance.

Thus, in the configuration in which the concaves are formed in the separation channel 112, since the large-size substance which is easy to cause the clogging passes relatively smoothly through the separation area, the clogging problem is reduced to remarkably improve the throughput.

Figure 46:
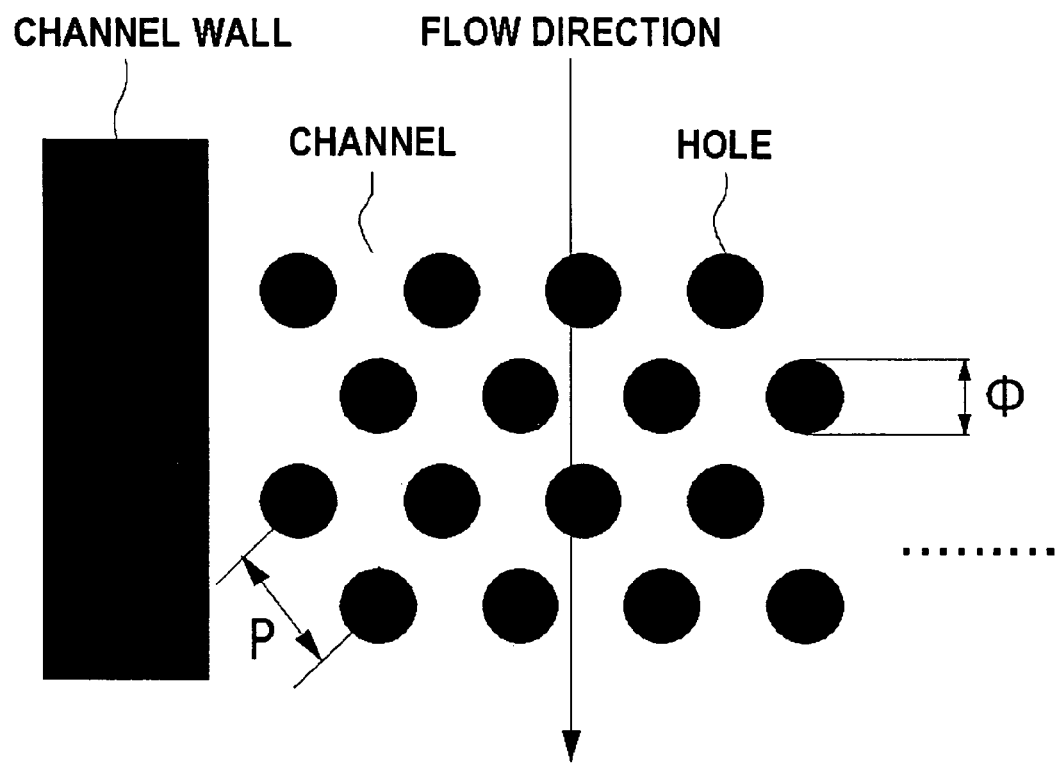
FIG. 46 is a view showing an arrangement of concaves in a sample separation area.

An example of the structure of the sample separation area which realizes the separation method shown in FIG. 45 will be described with reference to FIG. 46. As shown in FIG. 46, in the sample separation area, the concaves having opening maximum diameters $\phi$ are regularly formed at intervals p.

Figure 47:
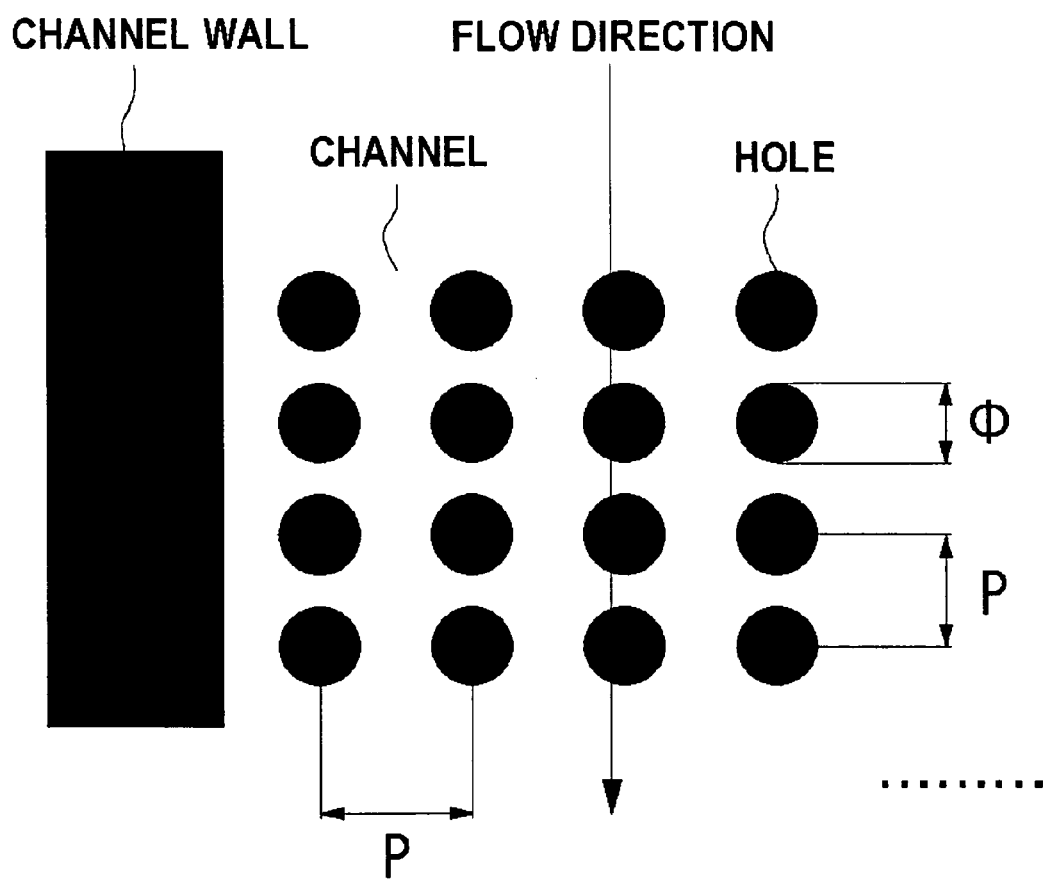
FIG. 47 is a view showing an arrangement of the concaves in the sample separation area.

FIG. 47 shows another example of the sample separation area. In this example, the concaves are orderly arranged in lines.

Figure 48:
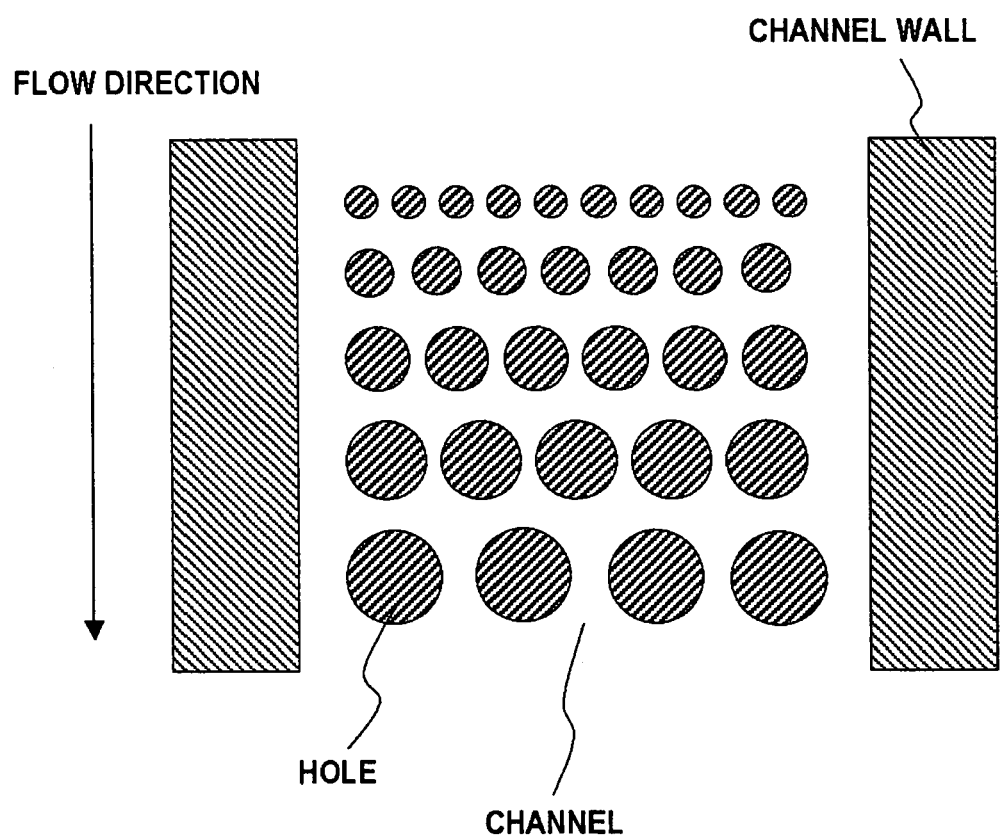
FIG. 48 is a view showing an arrangement of the concaves in the sample separation area.

FIG. 48 shows another example of the sample separation area. This example has the configuration in which the concaves are arranged while the dimensions of concaves are increased toward the flow direction.

Figure 49:
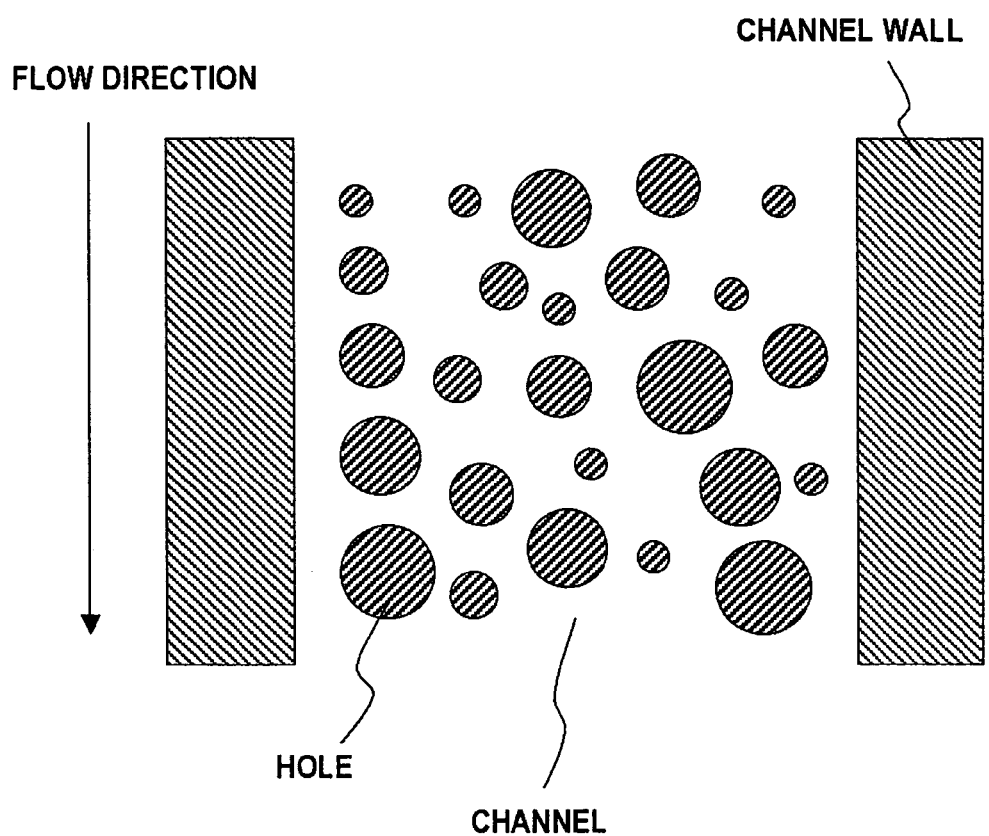
FIG. 49 is a view showing an arrangement of the concaves in the sample separation area.

FIG. 49 shows another example of the sample separation area. This example has the configuration in which the concaves having the different opening diameters are randomly arranged.

Figure 50:
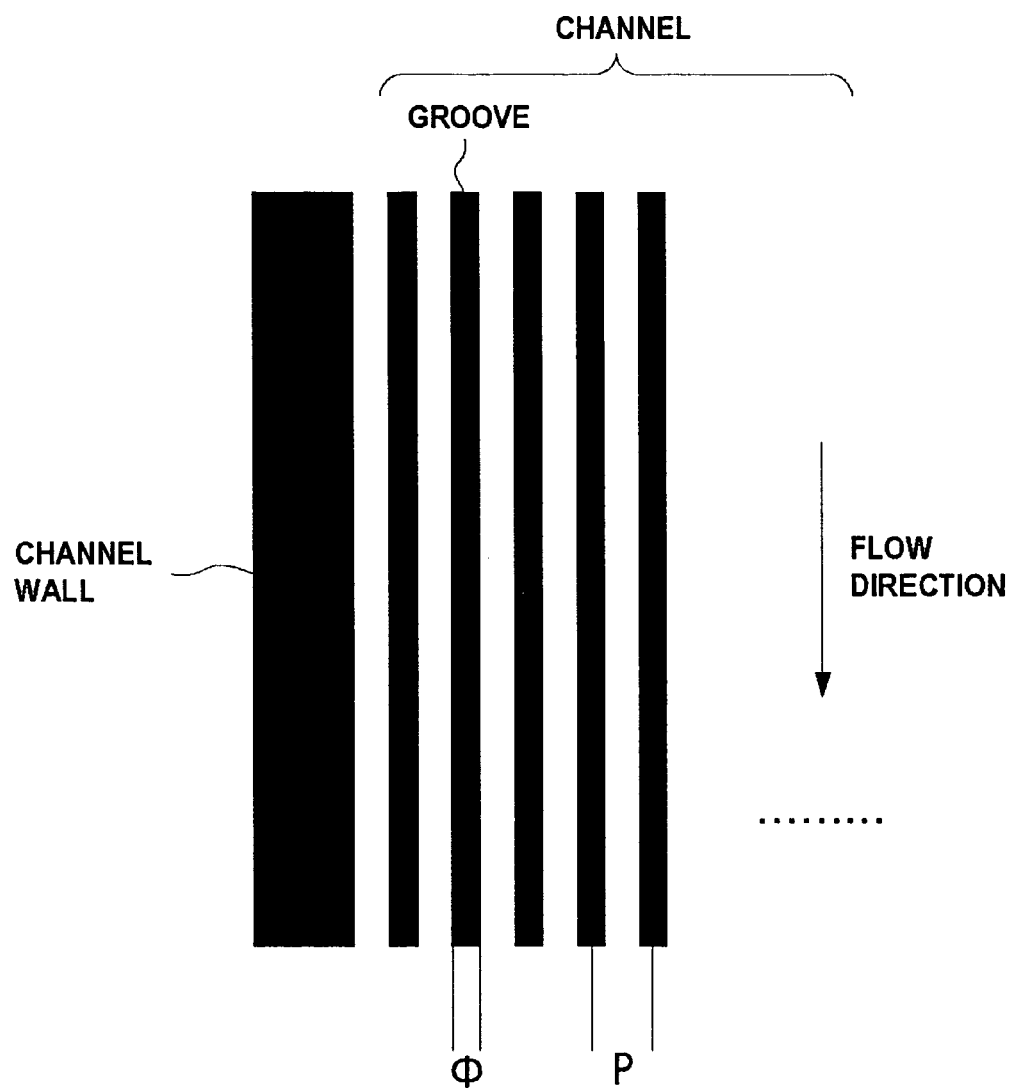
FIG. 50 is a view showing an arrangement of the concaves in the sample separation area.

FIG. 50 shows another example of the sample separation area. In this example, the concaves are formed in the stripe shape. That is, the concave is formed not in the hole but in the groove. In this case, φ and p indicate the width of the groove and the interval between the grooves respectively.

Figure 51:
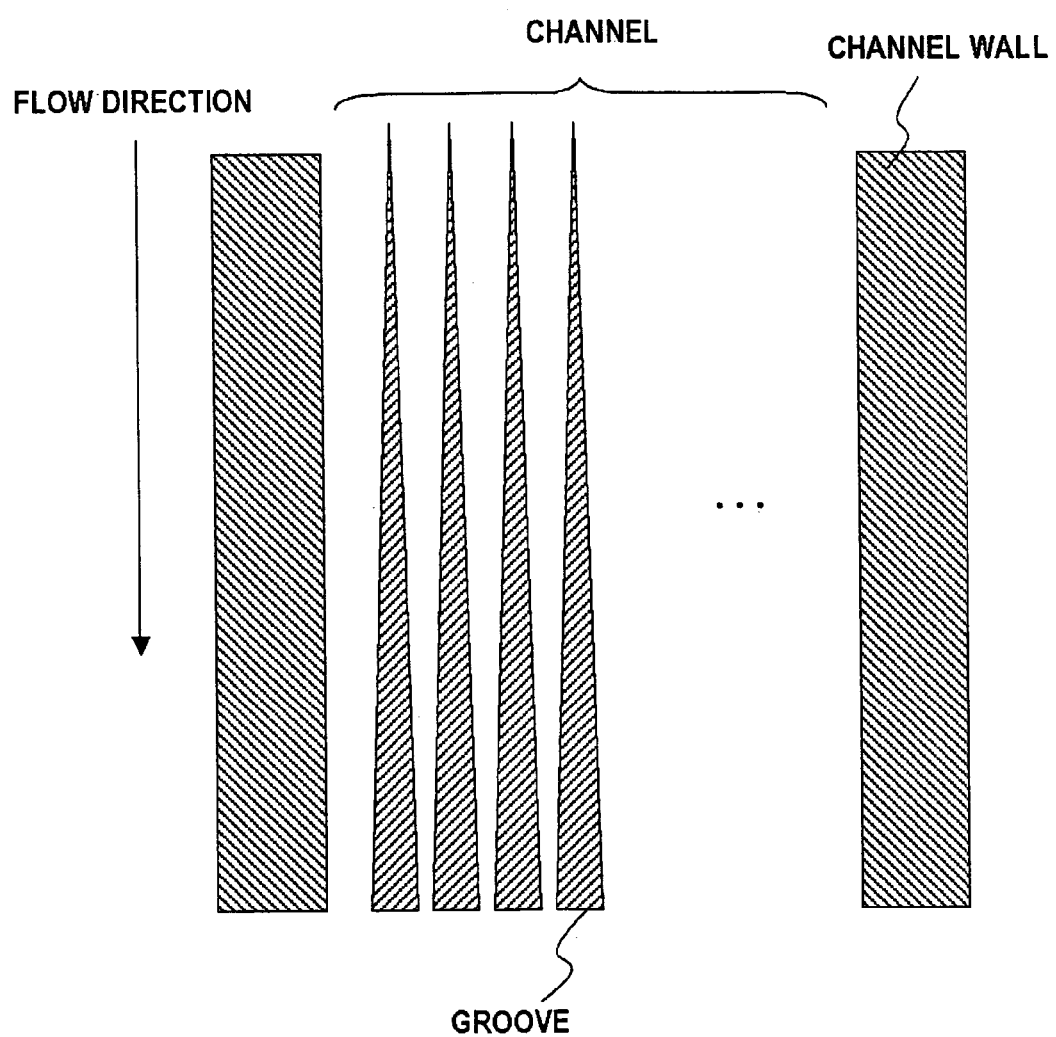
FIG. 51 is a view showing an arrangement of the concaves in the sample separation area.

FIG. 51 shows another example of the sample separation area. This example has the configuration in which the concaves the grooves whose widths are widened toward the flow direction are provided in the channel.

Figure 52:
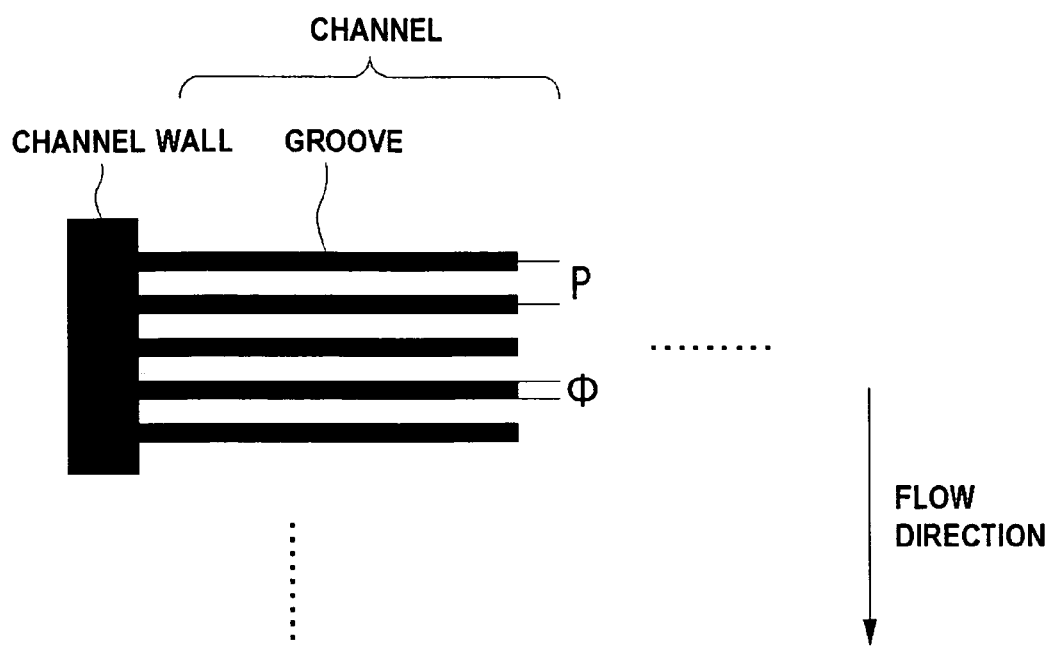
FIG. 52 is a view showing an arrangement of the concaves in the sample separation area.

FIG. 52 shows another example of the sample separation area. Similarly to FIG. 50, the concaves are formed in the stripe shape. Although the strip direction is parallel to the flow direction of the sample in FIG. 50, the strip direction is perpendicular to the flow direction of the sample in FIG. 52. In this case, φ and p also indicate the width of the groove and the interval between the grooves respectively.

The following effects are obtained by forming the sample separation area in the configuration shown in FIGS. 48, 49 and 51.

The separation effect by the hole is hardly obtained for the molecule larger than the dimensions of the hole and the groove. Accordingly, when the dimensions of the hole and the groove are set constant, the resolution for the molecule larger than the dimensions of the hole and the groove is decreased compared with the small molecule. Further, when the dimensions of the hole and the groove are set constant, the molecular size range in which the large separation effect is obtained becomes narrowed. Therefore, the channel is formed in the structures shown in FIGS. 48, 49, 51. Accordingly, the molecular size range in which the sufficient separation effect is obtained can be widened while the resolution for the large-size molecule can be increased The opening maximum diameter of the concave is appropriately selected according to the size of the component to be separated. For example, the opening maximum diameter of the concave may be substantially equal to the inertia radius corresponding to the median of the sizes of the molecular groups to be separated, or the opening maximum diameter may be slightly smaller or larger than the inertia radius. Specifically, the difference between the inertia radius corresponding to the median and the opening maximum diameter of the concave is set at values 100 nm or less, more preferably 10 nm or less, and most preferably 1 nm or less. The separation ability is further improved by appropriately setting the opening maximum diameter of the concave.

In the above configurations, the concaves are arranged at predetermined intervals. However, the concaves can also be arranged at different intervals in the sample separation area. Accordingly, the molecules and ions having the plural sizes such as the large size, the medium size, and the small size can efficiently be separated. For the arrangement of the concaves, as shown in FIG. 46, it is also effective to adopt the method in which the concaves are arranged in the zigzag manner with respect to the sample progress direction. Accordingly, the contact opportunity between the concave and the molecule is increased, so that the target component can efficiently be separated while the clogging is effectively prevented.

In the above configurations, the concaves are formed in the cylindrical shape. However, the shape of the concave is not limited to the cylindrical shape. For example, it is also possible to adopt the tapered shape in which an inner diameter of the concave is decreased toward the bottom surface. Specifically, the shape in which the inner diameter of the concave is decreased in a step manner as shown in FIG. 53(*a*) or the shape in which the inner diameter of the concave is continuously decreased as shown in FIGS. 53(*b*) and 53(*c*) can be cited as an example. In these cases, because the smaller molecule can be moved to the deep portion of the concave, the smaller molecule resides in the concave for longer time. As a result, the separation ability is further improved.

The tapered concaves can be provided by various techniques. For example, when the concaves are provided by the anodic oxidation process, the voltage is gradually lowered, which allows the tapered concave to be provided.

The tapered concaves can be provided by the etching. For example, when silicon is used as the substrate, a vertical hole having the substantially same inner diameter as the inner diameter of the bottom surface of the concave to be provided is made by the dry etching. Then, the wet etching is performed to the vertical hole with an isotropic etching solution. An exchange rate of the etching solution in the vertical hole becomes the minimum at the bottom surface of the vertical hole, and the exchange rate is gradually increased from the bottom surface of the vertical hole to the opening. Therefore, side etching is hardly generated near the bottom surface of the vertical hole, and the inner diameter is hardly enlarged. On the other hand, the degree of the side etching is gradually increased from the bottom surface to the opening, which results in the enlargement of the inner diameter. Thus, the tapered concave can be provided.

In the above configurations, the concaves are arranged on the plane. However, the concaves can stereoscopically be arranged. For example, the channel is divided into two layers by providing a separation plate in the channel, and the concaves are provided in the separation plate and the channel wall.

The configuration of this embodiment has a characteristic that the outflow is delayed as the molecular size is decreased. In order to perform preparative isolation of the small-size molecule at speed as fast as the large-size molecule, through holes having the diameters similar to the target molecular size can be provided in the separation plate. Therefore, because the target small-size molecule can bypass the channel provided in the channel, while the preparative isolation of the small-size molecule can be performed at speed as fast as the large-size molecule, the separation of other molecules can be realized.

FIG. 54 is a view showing an example of the configuration in which the channel is divided into the two layers. FIG. 54(*a*) is a vertically sectional view with respect to the flow direction. A channel 409 provided in a silicon substrate 417 is divided into the two layers by a separation plate 419. FIG. 54(*b*) is a sectional view taken on line A-A' of FIG. 54(*a*). Through holes 420 and concaves 421 are partially provided in the separation plate 419, and the molecule which can pass through the through hole 420 is moved to the channel 409 located in the lower portion of the drawing. The adaptation of such structure enables the rapid preparative isolation of the small-size molecule in which the outflow time is slow in the structure having the single-layer channel. Concaves 422 smaller than the concaves 421 can be provided in the separation plate 419 (FIG. 54(*c*)). Accordingly, the precise separation of the small-size molecule can be realized in the lower channel 409.

As shown in FIGS. 55(*a*) and 55(*b*), the pillars or the projections are provided in the channel, and the concaves can be provided in the pillar or the projection and the channel wall. Accordingly, the area of the separation area having the concaves is increased, so that the improvement of the separation ability can be achieved.

Figure 9:
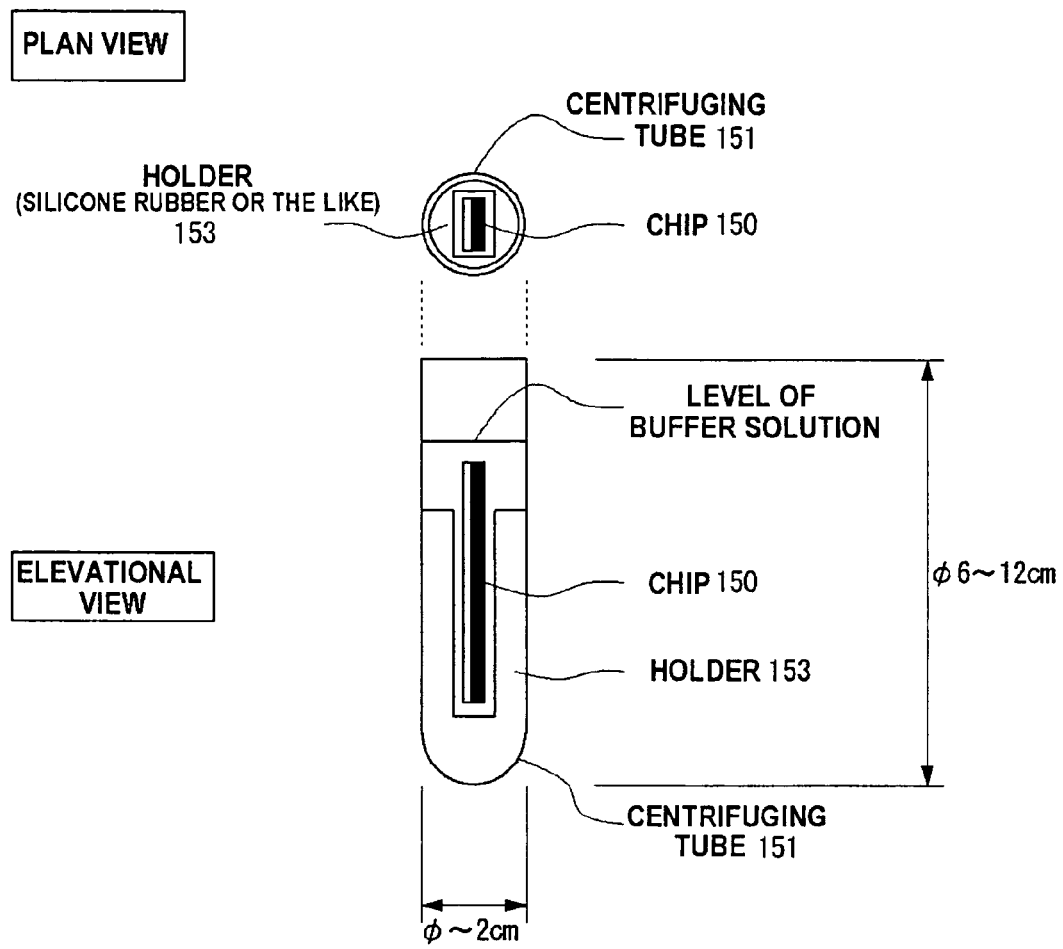
FIG. 9 is a view for explaining a method of introducing a buffer solution in the microchip.

In this embodiment, as with the first embodiment, the buffer solution can securely be introduced into the channel by the method described with reference to FIG. 9. The voltage may be applied in moving the sample by the method described with reference to FIG. 22. The means which applies the external force to the sample is not limited to the voltage. For example, in the case where the buffer solution containing the separation target sample is introduced while the buffer solution is not introduced in the channel, the buffer solution flows automatically into the channel by the capillarity. The separation can also be realized during this process.

In the case where the sample is separated and preparative isolation is realized, it is necessary to introduce the relatively large amount of sample, so that the depth of the channel is set at a deeper value. In this case, because the contact frequency between the separation target sample and the concave is small, sometimes the sufficient separation effect cannot be expected. Therefore, in this case, it is preferable that the molecule is positively introduced to the concave by applying the voltage between the upper surface and the bottom surface in the channel.

Figure 56:
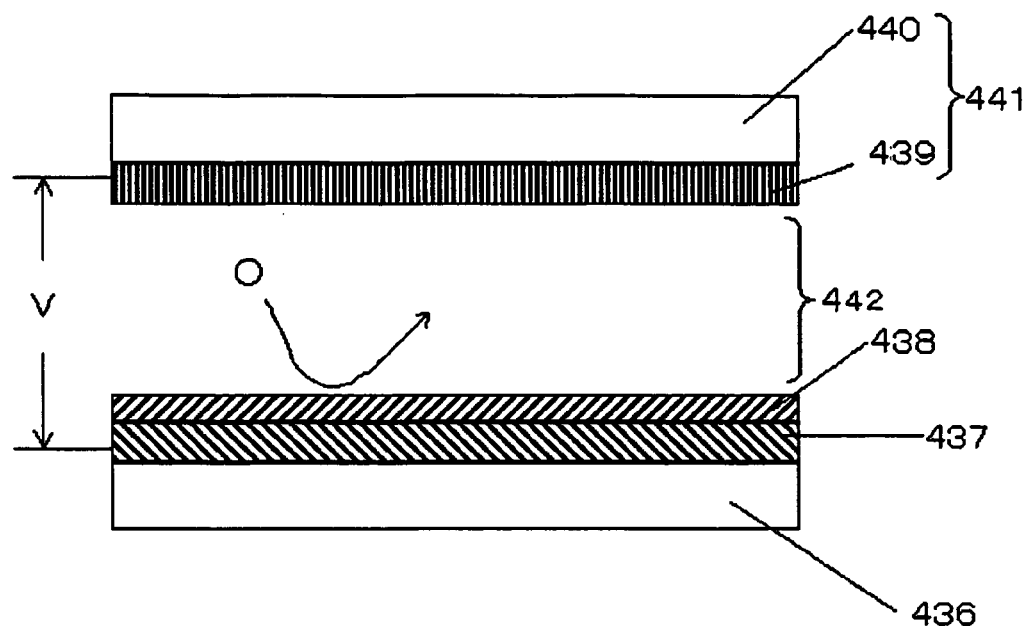
FIG. 56 is a view showing an example of a configuration of the separation channel in the microchip.

FIG. 56 shows an example of such embodiments. A gold electrode 437 is arranged on a glass substrate 436, and a porous alumina layer 438 is provided on the gold electrode 437. On the other hand, a covering portion 441 is provided on a channel 442, and the covering portion 441 includes a cover glass 440 and a transparent electrode 439 arranged beneath it. The gold electrode 437 is set at an anode and the transparent electrode 439 is set at a cathode. When the voltage is applied, the target molecule of the separation is moved in the channel while subjected to the external force from the transparent electrode 439 toward the gold electrode 437. Therefore, the contact frequency can be raised between the molecule and the concave, so that the improvement of the separation ability is realized. For the voltage, the direct-current voltage is used in the above description. However, both the direct-current voltage and the alternating voltage can be applied.

In the case where the direct-current voltage is adopted, usually the biomolecules such as DNA and the protein are negatively charged, so that the voltage is applied while the side on which the concave is provided is set at the positive electrode. When the excess voltage is applied, because the target molecule of the separation is difficult to escape from the concave, the outflow is extremely delayed. Therefore, it is preferable the applied electric field strength is 50 V/cm or less.

Figure 57:
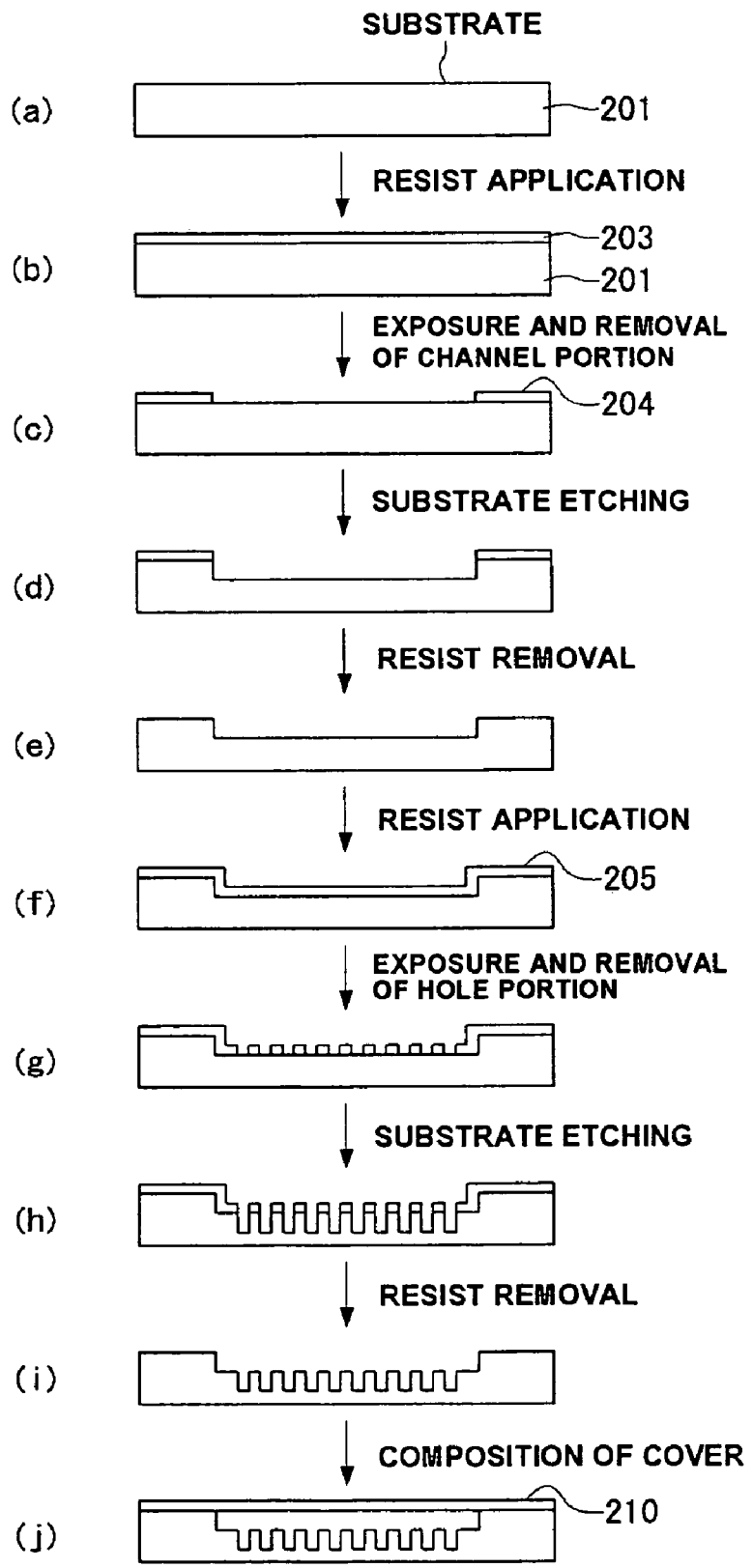
FIG. 57 is a view for explaining a process of producing the concave in a substrate.

Then, the method of forming the concaves in the substrate will be described. The concaves can be produced by etching the substrate. FIG. 57 is a view for explaining the method of forming the concaves in the substrate.

As shown in FIG. 57(a), the silicon substrate 201 is prepared, and the calix-arene electron beam negative resist 203 is applied thereon (FIG. 57(b)). Then, a portion which becomes the sample channel is exposed by the electron beam (EB). The development is performed by xylene, and the rinsing is performed by isopropyl alcohol. The resist 204 in which the patterning is performed as shown in FIG. 57(c) is obtained through this process.

Then, the silicon substrate 201 is etched by using it as the mask (FIG. 57(d)). After the resist is removed (FIG. 57(e)), the posi-type photoresist 205 is applied over the surface again (FIG. 57(f)). Then, the mask exposure is performed such that the channel portion is exposed, and the development is performed (FIG. 57(g)). The posi-type resist 205 is patterned such that the desired concaves (hole portions) are formed in the silicon substrate 201.

The RIE etching of the silicon substrate 201 is performed by using the mixture gas of $CF_4$ and $CHF_3$ (FIG. 57(h)). The resist is removed by the organic washing with the mixture solution of acetone, alcohol, and water (FIG. 57(i)). Then, the cover 210 is provided as required, and the concaves are finished (FIG. 57(j)).

Figure 58:
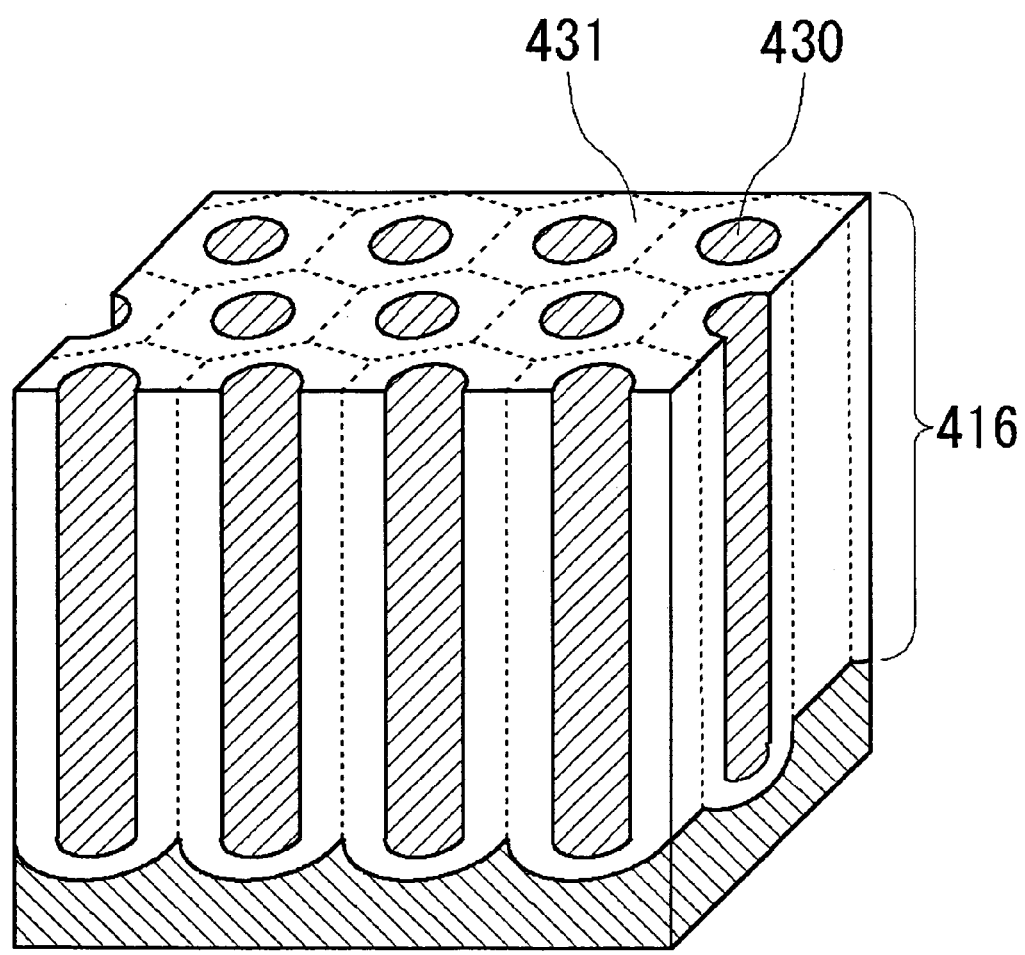
FIG. 58 is a view showing porous alumina.

The concave can also be formed by the anodic oxidation process. The anodic oxidation process is the treatment, in which the metal (For example, aluminum, titanium, zirconium, niobium, hafnium, tantalum) to be oxidized is set at the anode and current passage and oxidation is performed in an electrolytic solution. In this oxidation process, the acid electrolytic solution is used and water electrolysis by the current passage generates hydrogen in the cathode. However, oxygen is not generated in the anode, but an oxide coating layer is formed on the metal surface. In the case of aluminum, the oxide coating layer is called porous alumina. As shown in FIG. 58, a porous alumina layer 416 has a periodic structure in which a fine pore 430 is located in the center of each cell 431. These structures are formed in a self-organizing manner, so that the nanostructure can easily be obtained without performing the patterning. The interval between the cells is proportional to oxidation voltage (2.5 nm/V). In the case of aluminum, sulfuric acid (up to 30V), oxalic acid (up to 50V), and phosphoric acid (up to 200V) are used as the acid electrolytic solution according to the oxidation voltage.

On the other hand, the dimension of the fine pore depends on the oxidation conditions and the post-oxidation surface treatment. The diameter of the fine pore is enlarged as the oxidation voltage is increased. For example, when the oxidation voltage is set at 5V, 25V, 80V, and 120V, the fine pore has the maximum diameters of about 10=m, about 20 nm, about 100 nm, and about 150 nm respectively. The opening thereof can be formed in the circular or elliptic shape. After the porous alumina is formed, the surface treatment is performed such that the surface of the porous alumina is etched by for example 3 wt % phosphoric acid. The diameter of the fine pore is enlarged as the surface treatment time is increased.

Thus, the concaves having the desired diameter can regularly be provided at desired intervals by appropriately selecting the oxidation voltage and the surface treatment time.

Figure 59:
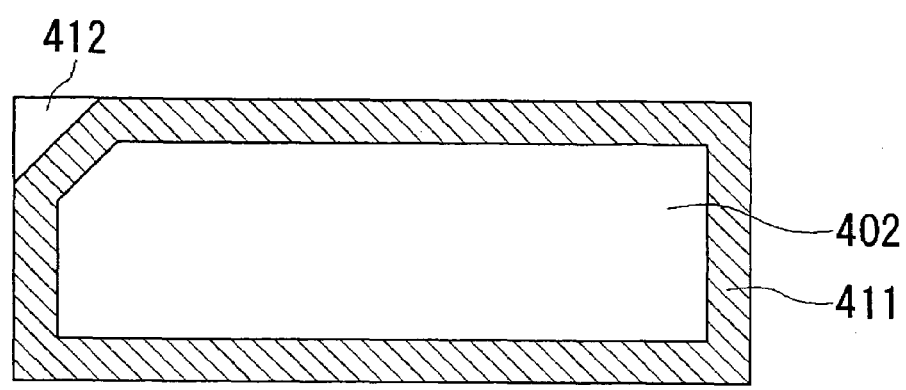
FIG. 59 is a view showing a state in which a peripheral portion of an aluminum layer is covered with an insulating film.

In order to form the more homogeneous porous alumina, as shown in FIGS. 59 and 87, it is preferable that the anodizing oxidation is performed while a peripheral portion of the target aluminum layer of the anodic oxidation process is of covered with an insulating film. FIG. 59 is a top view showing the state in which the peripheral portion of the aluminum layer 402 formed on the insulating substrate is covered with an insulating film 411. Insulating resins such as photosensitive polyimide can be used as the insulating film 411. Accordingly, it is possible to suppress the phenomenon that the anodizing oxidation reaction progresses rapidly only in the periphery of an electrode attachment portion 412 while an inoxidizable area is formed in the portion far away from the anode, so that the homogeneous porous alumina can be provided over an aluminum layer 402.

According to the method described by Asou et al. (J. Vac. Sci. Technol., B, 19(2), 569(2001)), it is also possible that the porous alumina is provided in the desired arrangement such that the anodizing oxidation is performed after a concave is previously formed with the mold at the point where the porous alumina is provided. In this case, the desired concave maximum diameter can also be formed by controlling the voltage.

FIG. 87 is a view showing the state in which the peripheral portion of the aluminum layer 402 is covered with an electroconductive layer 413. FIG. 87(a) is a top view and FIG. 87(b) is a sectional view. As shown in FIGS. 87(a) and 87(b), the electroconductive material (gold and the like) to which the anodic oxidation process cannot be performed is evaporated on the aluminum layer 402 provided on a slide glass 401 to form the electroconductive layer 413, and the anodizing oxidation is performed, which allows the homogeneous porous alumina to be provided over the aluminum layer 402. In the case where gold is used as electroconductive material, the electroconductive layer 413 is removed by a gold etchant after the anodizing oxidation is performed. The gold etchant is obtained by mixing potassium iodide, iodine, and water. A mixture ratio is set at potassium iodide:iodine:water=1:1:3 (weight ratio).

In this embodiment, in order to prevent the adhesion of the molecules such as DNA and the protein to the wall surface of the separation channel 112, it is preferable that the channel wall is hydrophilically treated such as coated. As a result, the good separation ability can be exerted. The substances having the structure similar to phospholipids constituting the cell membrane can be cited as an example of the coating material. An example of the substance includes LIPIDURE (registered trademark, product of NOF CORPORATION). When LIPIDURE (trademark) is used, LIPIDURE is dissolved at the concentration of 0.5 wt % in the buffer solution such as TBE buffer, the channel is filled with the solution, and is left for several minutes. Therefore, the channel wall can be coated.

The molecules such as DNA can also be prevented from adhering to the channel wall by coating the channel wall with the repellent resin such as fluororesin or the hydrophilic substance such as bovine serum albumin.

Ninth Embodiment

Figure 60:
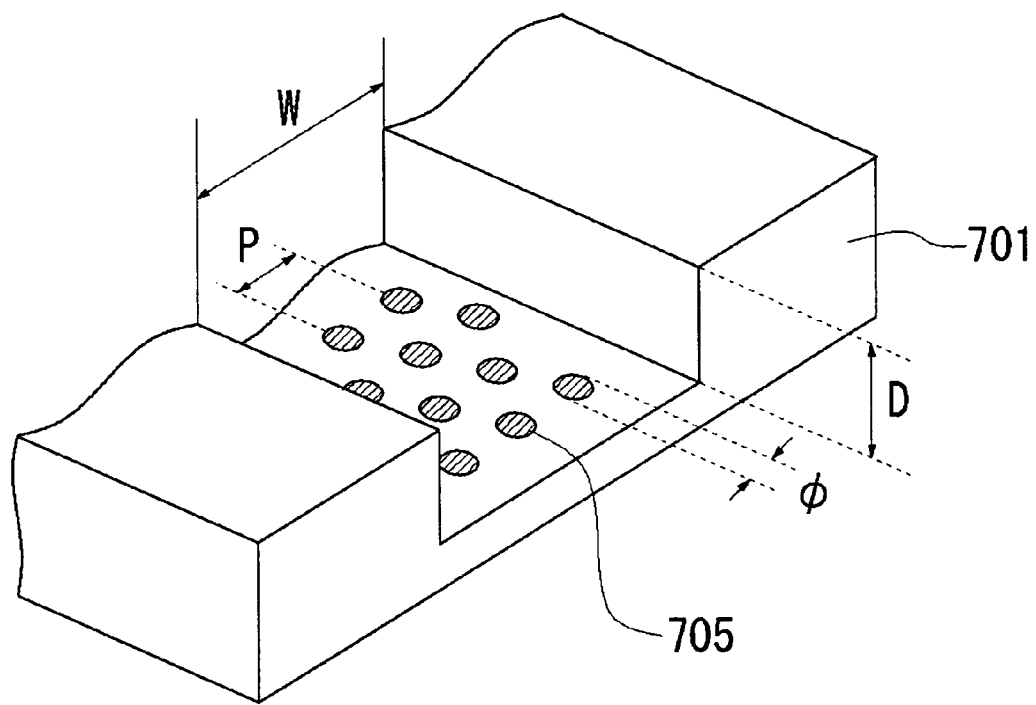
FIG. 60 is a view showing a detailed configuration of the separation channel in the microchip according to an embodiment.

In the microchip used for the mass spectrometry system 351 of FIG. 1, the hydrophilic area and the hydrophobic area may be formed on the surface of the channel. For example, the sample separation area where the hydrophilic area and the hydrophobic area are formed may be formed in the separation channel 112 or separation channel 540 provided in the microchip having the configurations of FIGS. 3, 21, 22, 23, 35, and 37 or the like. The surface of the sample separation area includes the plural hydrophobic areas and the hydrophilic area. The hydrophobic areas are two-dimensionally formed at substantially even intervals. The hydrophilic area occupies the surface of the sample separation portion except for the hydrophobic areas. FIG. 60 shows the detailed structure of the separation channel 112 or the separation channel 540 in FIG. 3, FIG. 21, FIG. 22, FIG. 35, or FIG. 37. Referring to FIG. 60, the groove portion having the depth D is formed in a substrate 701, and the hydrophobic areas 705 having the diameters $\phi$ are regularly formed at even intervals. In this embodiment, the hydrophobic areas 705 are formed by causing the coupling agent having the hydrophobic group to adhere to the surface of the substrate 701 or by bonding the coupling agent to the surface of the substrate 701. A cover, not shown in FIG. 60, may be provided in the upper portion of the channel during the separation, which allows the solvent to be prevented from vaporizing. The pressure enables the movement of the sample in the channel. However, it is also possible to form the structure in which the cover is not provided. In the case of the structure in which the cover is not provided, the operation in which the cover is removed is not required before the mass spectrometric analysis is performed, which improves the operability.

For example, the dimensions of the portions in FIG. 60 are set as follows:
W: 10 to 20 µm,
D: 50 nm to 10 µm,
$\phi$: 10 to 1000 nm, and
p: 50 nm to 10 µm.

The dimension of each portion is appropriately set according to the purpose of the separation. For example, about p, in the processes of:
(i) The separation and the condensation of a cell and other components,
(ii) The separation and the condensation of a solid matter (fragment of cell membrane, mitochondria, and endoplasmic reticulum) and a liquid fraction (cytoplasm) in the components obtained by destroying the cell, and
(iii) The separation and the condensation of a high-molecular weight component (DNA, RNA, protein, and sugar chain) and a low-molecular weight component (steroid, glucose, and the like) in the liquid fraction component,
in the case of (i), it can be set in the range of 1 µm to 1 mm,
in the case of (ii), it can be set in the range of 100 nm to 10 µm, and
in the case of (iii), it can be set in the range of 1 nm to 1 µm.

The magnitude of the depth D is an important factor which dominates the separation performance. It is preferable that the depth D is about one to about ten times as the inertia radius of the separation target sample, and it is more preferable that the depth D is about one to about five times as the inertia radius.

FIG. 61 is a top view (FIG. 61(a)) and a side view (FIG. 61(b)) showing the structure of FIG. 60. Usually the hydrophobic area 705 has the film thickness ranging from 0.1 to 100 nm. The surface of the substrate 701 is exposed in the portions except for the hydrophobic areas 705. In the structure of FIG. 60, the hydrophobic surface is formed with the predetermined pattern on the hydrophilic surface by selecting the hydrophilic material such as the glass substrate for the substrate 701, which develops the sample separation function. That is, when the hydrophilic buffer solution and the like are used as a carrier solvent, the sample passes only through the hydrophilic surface and the sample does not pass through the hydrophobic surface. Therefore, the hydrophobic area 705 functions as an obstacle of the sample passage to develop the sample separation function.

The separation method by the pattern formation of the hydrophobic area 705 will be described by focusing on the molecular size. It is thought that two methods are mainly adopted as the separation method. One is the separation method shown in FIG. 62. In this method, as with FIG. 8, the larger the molecular size, the larger the hydrophobic area becomes the obstacle. Therefore, it takes a longer time for the larger-size molecule to pass through the separation portion shown in the picture. The small-size molecule passes relatively smoothly through the gap between the hydrophobic areas 705, and the small-size molecule passes through the separation area at short times when compared with the large-size molecule.

Figure 62:
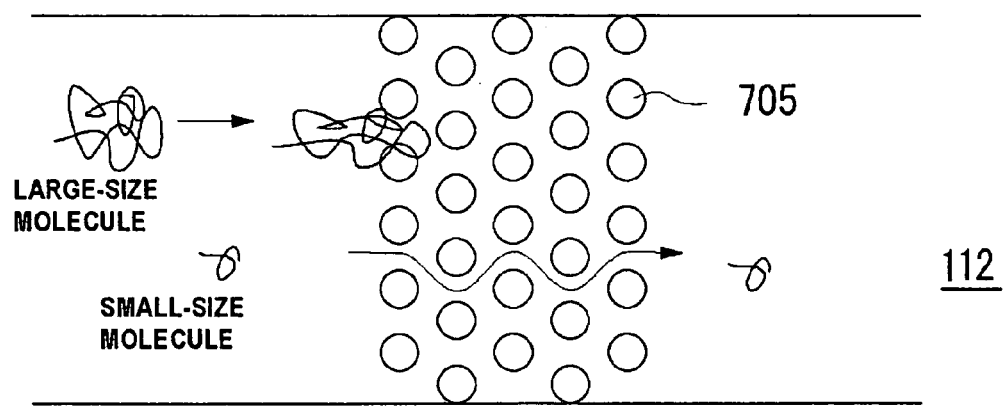
FIG. 62 is a view for explaining the sample separation method.
Figure 63:
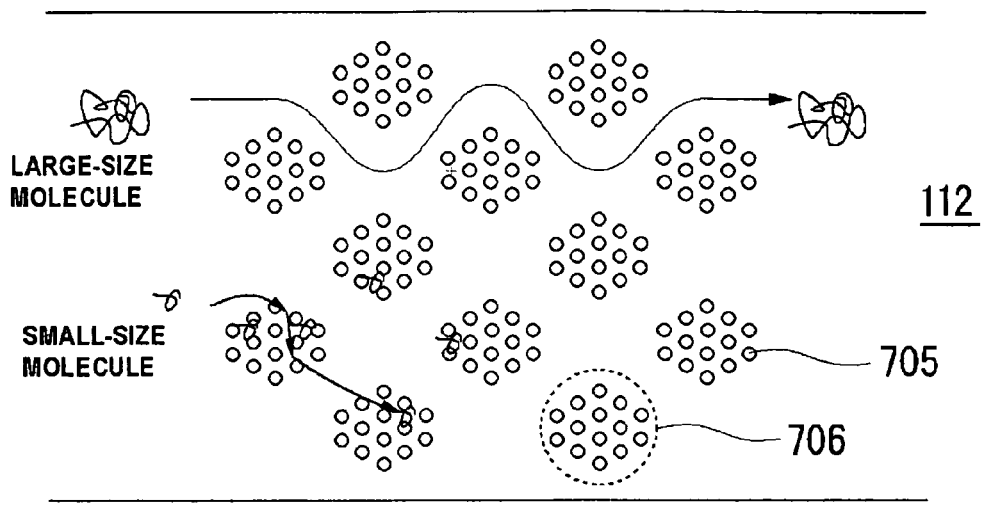
FIG. 63 is a view for explaining the sample separation method.

On the contrary to FIG. 62, the separation method shown in FIG. 63 is one in which the large-size molecule flows out rapidly while the small-size molecule flows out slowly. In the separation method of FIG. 62, as with FIG. 25, when the gigantic-size substance is contained in the sample, the gigantic-size substance closes up the interval between the hydrophobic areas 705, and sometimes the separation efficiency is decreased. In the separation method shown in FIG. 63, this problem is solved. Referring to FIG. 63, plural sample separation portions 706 are formed in the separation channel 112 while separated from one another. In each sample separation portions 706, the hydrophobic areas 705 having the substantially same dimensions are arranged at even intervals.

Since the wide path through which the large-size molecule passes is provided between the sample separation portions 706, contrary to FIG. 62, the large-size molecule flows out rapidly and the small-size molecule flows out slowly. This is because the large-size molecule passes smoothly through the path between the sample separation portions 706 while the smaller-size molecule is trapped in the separation area to pass through the longer path. As a result, the small-size substance is separated while discharged after the large-size substance. Since the large-size substance passes relatively smoothly through the separation area, the problem that the large-size molecule is trapped between the hydrophobic areas 705 to decrease the separation efficiency is decreased, and the separation efficiency is significantly improved. In order to enhance the effect more significant, it is preferable that the width of a path between the adjacent sample separation portions 706 is larger than the gap between the hydrophobic areas 705 in the sample separation portion 706. The width of the path is preferably about 2 to about 200 as times the gap between the hydrophobic areas 705, more preferably about 5 to about 100 times as the gap.

In the example of FIG. 63, the hydrophobic areas 705 having the same dimensions are formed at even intervals in each sample separation area. However, the hydrophobic areas 705 having the different dimensions may be formed at different intervals in each sample separation area.

When the substance having the molecular-order size is separated, the width of the path between the sample separation portions and the interval between the hydrophobic area 705 in the sample separation portion are appropriately selected according to the size of the component to be separated (organic molecule such as nucleic acid, amino acid, peptide, and protein, or molecule and ion such as chelated metal). For example, it is preferable that the interval between the hydrophobic areas 705 is substantially equal to the inertia radius of the minimum-size molecule included in the sample or is slightly smaller or larger than it. Specifically, the difference between the inertia radius of the minimum-size molecule included in the sample and the interval between the hydrophobic areas 705 is set at values 100 nm or less, more preferably 50 nm or less, and most preferably 10 nm or less. The separation ability is further improved by appropriately setting the first interval.

It is preferable that the interval (width of path) between the adjacent sample separation portions 706 is substantially equal to the inertia radius of the molecule contained in the sample or is slightly smaller or larger than it. Specifically, the difference between the inertia radius of the largest-sized molecule contained in the sample and the interval between the sample separation portions is set within 10% of the inertia radius of the molecule, more preferably within 5%, and most preferably within 1%. When the interval between the sample separation portions 706 is too widened, sometimes the separation of the small-size molecule is not sufficiently performed. When the interval between the sample separation portions 706 is too narrowed, sometimes the clogging is easy to occur.

In this embodiment, the hydrophobic areas are arranged at constant intervals. However, the hydrophobic areas can also be arranged at different intervals in the sample separation portion 706. Accordingly, the molecules and ions having the plural sizes such as the large size, the medium size, and the small size can efficiently be separated. For the arrangement of the hydrophobic areas, it is also effective to adopt the method in which the hydrophobic areas are arranged in the zigzag manner with respect to the sample progress direction. Accordingly, the target component can efficiently be separated.

In this embodiment, similarly to the above embodiments, as shown in FIG. 22, the voltage is applied to the both ends of the separation channel 112, which allows the sample to be moved in the separation channel 112. At this point, the voltage for suppressing electroendosmotic flow may be applied except for the voltage for imparting the external force to the sample. In the configuration of FIG. 22, for the purpose thereof, the zeta correction voltage is applied to the substrate. Accordingly, the electroendosmotic flow can be suppressed to effectively prevent the measurement peak from broadening.

The method of producing the microchip of this embodiment will be described taking the channel shape of the microchip 307 of FIG. 21 as an example with reference to FIGS. 64 to 69.

A groove portion 730 is provided in the surface of the substrate 701 as shown in FIG. 64(*a*) and a sample separation area 731 is formed at a predetermined point in the groove portion 730 as shown in FIG. 64(*b*), which obtains the channel shape of FIG. 21. Then, the process of forming the groove portion 730 in the substrate 701 of FIG. 64 (*a*) will be described with reference to FIG. 65. An example in which the glass substrate is used as the substrate 701 will be described in this embodiment.

Figure 65:
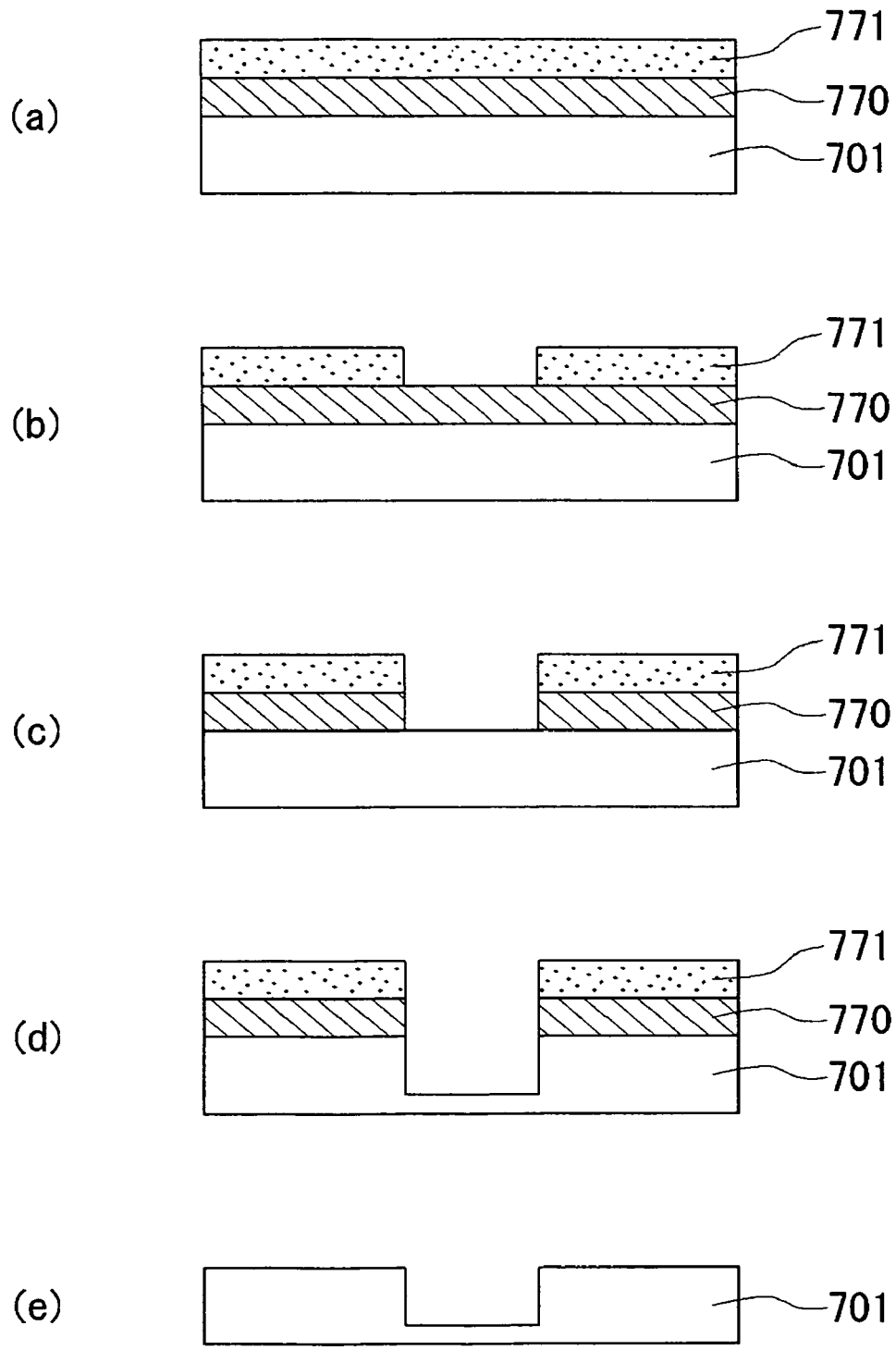
FIG. 65 is a view for explaining the microchip producing method.

First a hard mask 770 and a resist mask 771 are sequentially formed on the substrate 701 (FIG. 65(*a*)). A predetermined opening is provided in the resist mask 771 (FIG. 65(*b*)). The dry etching is performed by using the resist mask 771, in which the opening is provided, as the mask to obtain the state shown in FIG. 65(*c*). $SF_6$ and the like are used as the etching gas. Then, the wet etching is performed to the substrate 701 using the etching solution such as buffered hydrofluoric acid. Usually the etching depth is set at about 1 μm. FIG. 65(*d*) shows the state in which the wet etching is ended. Finally the hard mask 770 and the resist mask 771 are removed (FIG. 65(*e*)). The groove portion 730 shown in FIG. 64(*a*) is formed through the above processes.

In the process of forming the groove portion 730 in FIG. 64(*a*), it is also possible that the surface of the groove portion 730 is formed in the hydrophilic state and the surface except for the groove portion 730 is formed in the hydrophilic surface. Then, the process of forming this structure will be described with reference to FIG. 66. A hydrophobic surface treatment film 720 is formed over the surface of the structure obtained in FIG. 65(*e*) (FIG. 66(*a*)). 3-thiol propyl triethoxysilane can be cited as an example of the material constituting the hydrophobic surface treatment film 720.

Figure 66:
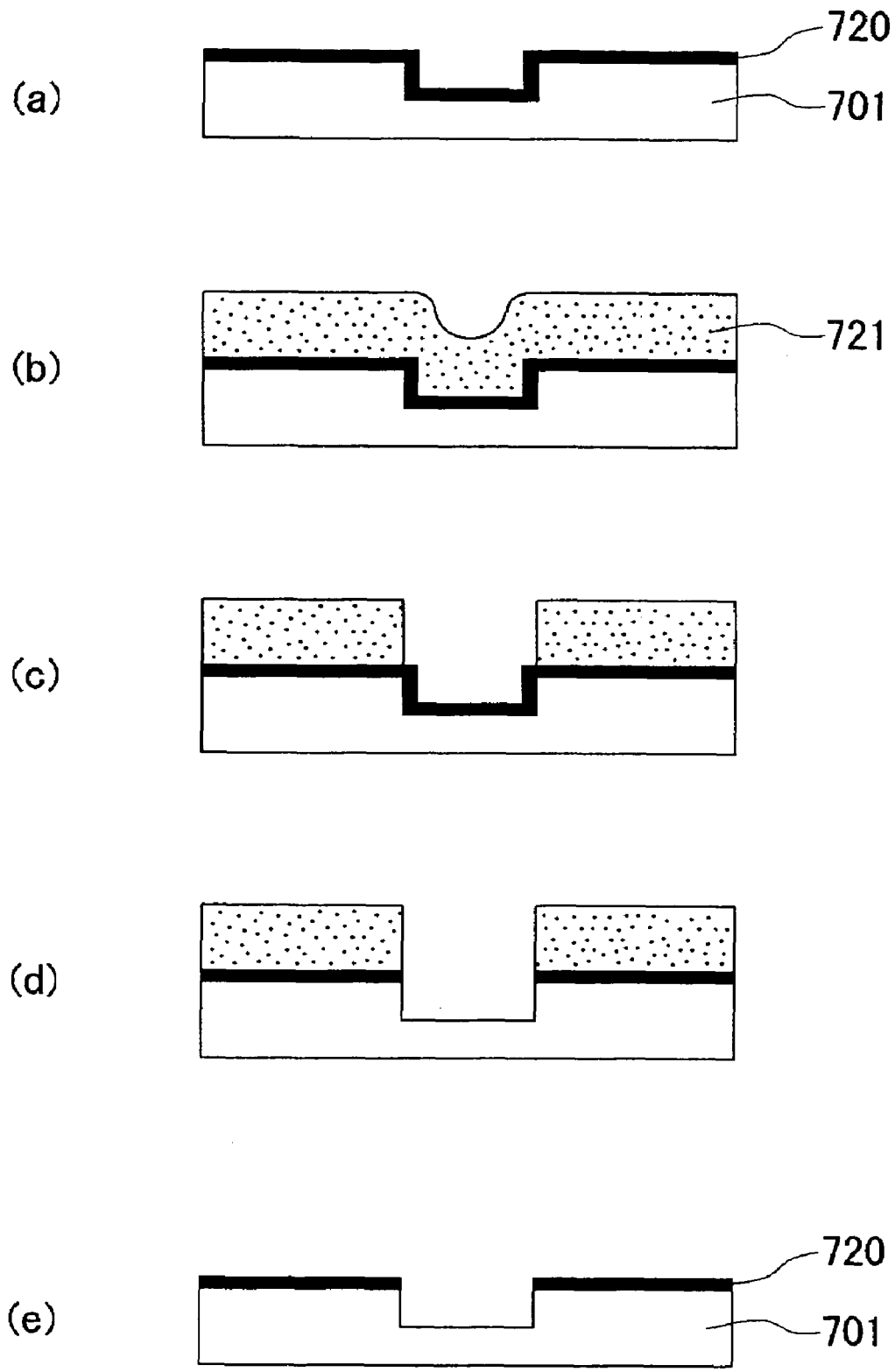
FIG. 66 is a view for explaining the microchip producing method.

Then, a resist 721 is applied to the surface of the substrate by spin coating method, and the resist 721 is dried (FIG. 66(*b*)). The opening corresponding to the groove portion is provided in the resist 721 (FIG. 66(*c*)). The dry etching is performed by using the resist 721 in which the opening is provided as the mask (FIG. 66 (*d*)). The resist 721 is removed by an ashing and stripping solution process. The state shown in FIG. 66(*e*) is obtained by performing the above processes. That is, the inner wall of the sample channel groove has the structure in which the hydrophilic surface of the substrate 701 made of the glass material is exposed while other portions are covered with the hydrophobic surface treatment film 720. Therefore, when the hydrophilic solvent is used as the carrier solvent, the sample never leaks outside the groove.

Figure 67:
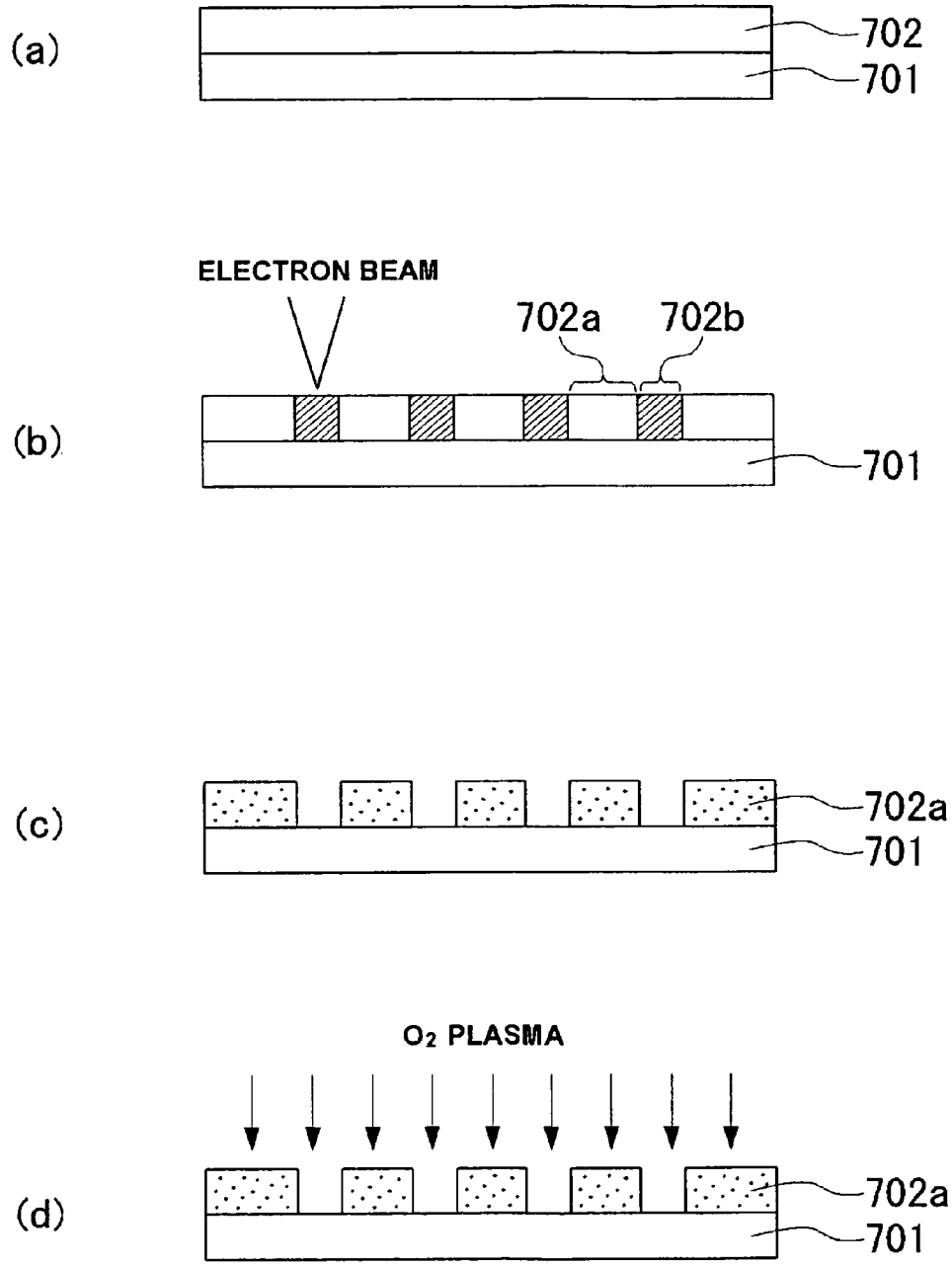
FIG. 67 is a view for explaining the microchip producing method.
Figure 69:
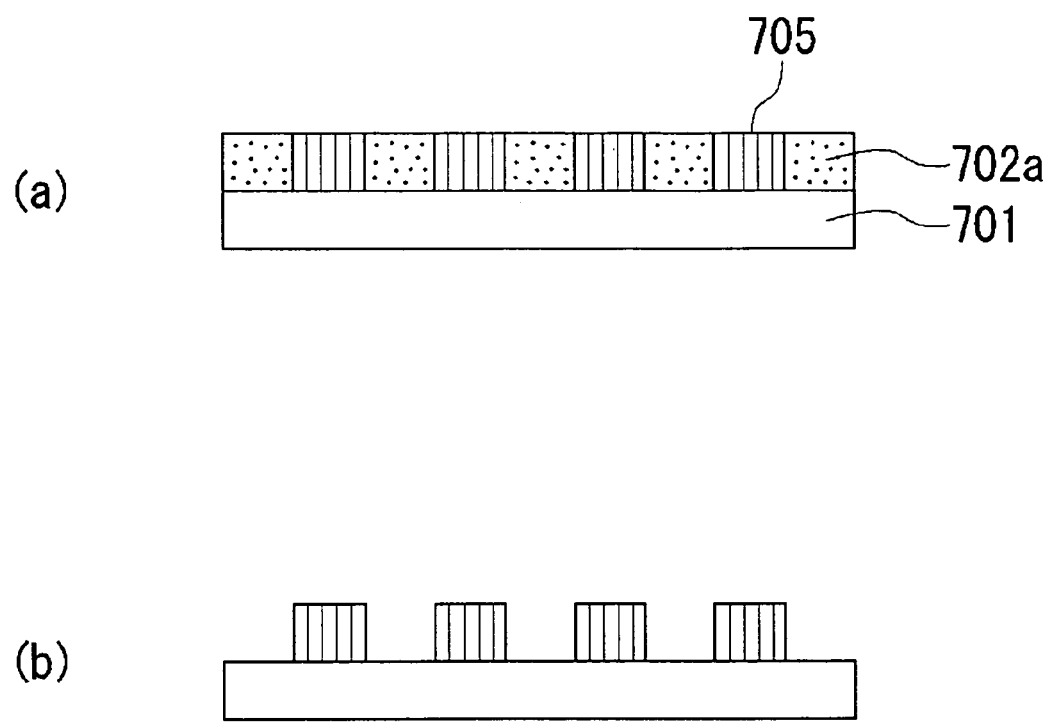
FIG. 69 is a view for explaining the microchip producing method.

Then, the process of forming the sample separation area 731 in FIG. 64(*b*) will be described with reference to FIG. 67. As shown in FIG. 67(*a*), an electron beam exposure resist 702 is formed on the substrate 701. Then, the pattern exposure is performed to the electron beam exposure resist 702 to obtain the pattern having the predetermined shape by the electron beam (FIG. 67(b)). When the exposed portions are dissolved and removed, the opening patterned in the predetermined shape is formed as shown in FIG. 67(c). Then, oxygen plasma ashing is performed as shown in FIG. 67(d). The oxygen plasma ashing is required in forming the sub-micron order pattern. When the oxygen plasma ashing is performed, a ground to which the coupling agent adheres is activated to obtain the surface suitable for the precise pattern formation. On the contrary, when the large patterns not lower than micrometer order are formed, the oxygen plasma ashing is not required.

The state of FIG. 68(a) is obtained after the ashing. In the drawing, resist residues and contaminations are deposited to form a hydrophilic area 703. In the state of things, the hydrophobic area 705 is formed (FIG. 68(b)). For example, a vapor phase method can be used as the method of depositing the film constituting the hydrophobic area 705. In this case, the substrate 701 and the solution containing the coupling agent having the hydrophobic group are arranged in the sealed chamber and left to stand for a predetermined time, which allows the film to be formed. According to this method, since the solvent and the like do not adhere to the surface of the substrate 701, the treatment film having the desired fine pattern can be obtained. Another film deposition method is a spin coating method. In this case, the solution of the coupling agent having the hydrophobic group is applied to perform the surface treatment, and the hydrophobic area 705 is formed. 3-thiol propyl triethoxysilane can be used as the coupling agent having the hydrophobic group. A dipping method and the like can also be used as the film deposition method. The hydrophobic area 705 is not deposited on the upper portion of the hydrophilic area 703 but deposited only on the exposed portion of the substrate 701, which obtains the surface structure in which the many hydrophobic areas 705 are formed while separated from one another as shown in FIG. 61.

In addition to the above processes, the same surface structure can also be obtained by the following method. In the method, after forming an unexposed portion 702a in which the patterning is performed as shown in FIG. 67(c), the hydrophobic area 705 is formed by depositing 3-thiol propyl triethoxysilane in the resist openings without performing the oxygen plasma ashing as shown in FIG. 69(a). Then, the structure of FIG. 69(b) is obtained by performing the wet etching with the solvent which can selectively remove the unexposed portion 702a. At this point, it is important to select the solvent which does not damage the film constituting the hydrophobic area 705. Acetone can be cited as an example of the solvent like this.

Figure 71:
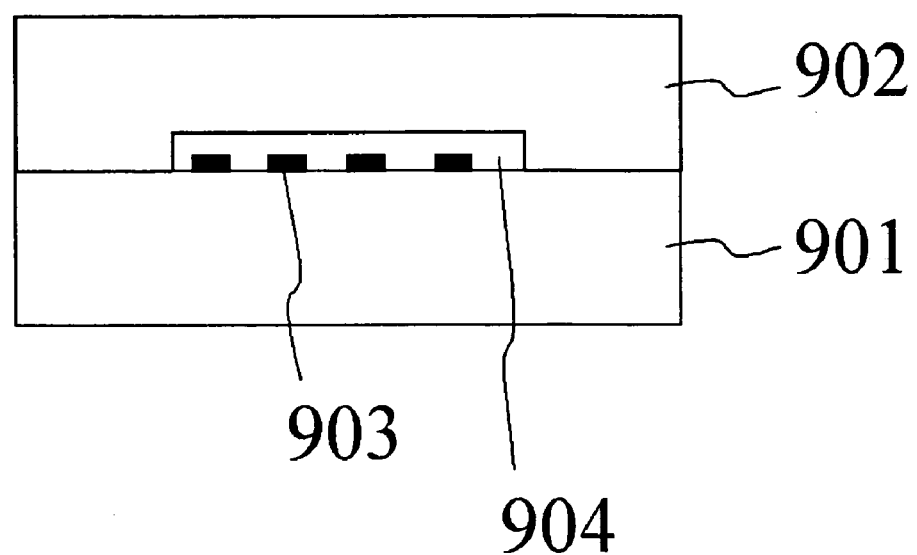
FIG. 71 is a sectional view showing a schematic configuration of the microchip used for the mass spectrometry system according to an embodiment.

In the above embodiment, the hydrophobic area is formed in the channel groove portion. In addition, the following method can be adopted. As shown in FIGS. 70(a) and 70(b), two kinds of substrates are prepared. The substrate shown in FIG. 70(a) has the configuration in which a hydrophobic film 903 is formed on a glass substrate 901. The hydrophobic film 903 is formed by a compound having the hydrophobic group such as 3-thiol propyl triethoxysilane. The hydrophobic film 903 is formed in the predetermined patterning shape. The position where the hydrophobic film 903 is provided becomes the sample separation portion. On the other hand, the substrate shown in FIG. 70(b) has the configuration in which a stripe-shaped groove is provided in the surface of a glass substrate 902. The groove portion becomes the sample channel. The method of forming the hydrophobic film 903 is described above. AS described above, the stripe-shaped groove can also easily be produced in the surface of the glass substrate 902 by performing the wet etching with the mask. The configuration of this embodiment can be obtained by bonding them as shown in FIG. 71. A space 904 formed by the two substrates becomes the sample channel. According to this method, the hydrophobic film 903 is formed on the flat surface, so that the production is easy to perform and good product stability is obtained.

The method, in which the film containing the silane coupling agent is formed over the substrate by an LB film pulling-up method and a micro pattern including the hydrophilic/hydrophobic properties is formed, can be used as the coupling agent film producing method.

In this embodiment, only one hydrophobic area can be provided in the sample separation area. In this case, for example, one hydrophobic area extending in the sample flow direction can be formed in the separation channel having the hydrophilic surface. In this case, the sample can also be separated by the surface characteristic of the sample separation area when the sample passes through the separation channel.

Further, the channel itself can be formed by the above hydrophobic treatment and hydrophilic treatment.

In the case where the channel is formed by the hydrophobic treatment, the portion corresponding to the channel wall is formed by the hydrophobic area using the hydrophilic substrate such as the glass substrate. Because the hydrophilic buffer solution progresses while avoiding the hydrophobic area, the channel is formed between the wall portions. It is possible that the channel is coated, or it is possible that the channel is not coated. In the case where the channel is coated, it is preferable that the several-µm gap is formed between the substrate and the cover. The gap is realized by bonding the cover to the substrate, wherein an overlap width is set in the vicinity of an edge of the cover and viscous resin such as PDMS and PMMA are used as paste. Even if only in the vicinity of the edge of the cover is bonded to the substrate, the hydrophobic area repels water when the buffer solution is introduced, so that the channel is formed.

On the other hand, in the case where the channel is formed by the hydrophilic treatment, the hydrophilic channel is formed in the hydrophobic substrate or the substrate surface which is formed in the hydrophobic state by a silazane treatment or the like. Because the buffer solution progresses only into the hydrophilic area, the hydrophilic area is to be the channel.

The hydrophobic treatment or the hydrophilic treatment can be performed by a printing technology such as stamping and inkjet printing. A PDMS resin is used in the stamping method. In the PDMS resin, resinification is performed by polymerizing silicone oil, and the gap between the molecules is filled with the silicone oil after the resinification. Therefore, when the PDMS resin is brought into contact with the hydrophilic surface, specifically a glass surface, the contact portion becomes the strong hydrophobic property to repel water. By utilizing this phenomenon, a PDMS block formed the concave at the position corresponding to the channel portion is brought into contact with the hydrophilic substrate as a stamp and the channel is easily produced by the hydrophobic treatment descrived above.

In the inkjet printing method, low-viscous type silicone oil is used as ink of the inkjet printing, and a hydrophilic resin thin film such as polyethylene, PET, cellulose acetate, cellulose thin film (cellophane) is used as print paper. The same effect is also obtained by printing the pattern, to which silicone oil adheres, in the channel wall portion.

A hydrophobic patch or hydrophilic patch having the predetermined shape is formed by the hydrophobic treatment and the hydrophilic treatment, and thereby a filter which does not pass the substance not lower than a specific size while passing the substance lower than the specific size can also be formed in the channel.

When the filter is formed by the hydrophobic patch, a broken line-shaped filter pattern can be obtained by linearly repeatedly arranging the patches at predetermined intervals. The interval between the hydrophobic patches is larger than the size of the substance to pass through and smaller than the size of the substance not to pass through. For example, when the substances 100 μm or more is removed, the interval between the hydrophobic patches is narrower than 100 μm, for example, the interval is set at 50 μm.

The filter can be realized by integrally forming the hydrophobic area pattern for forming the channel and the above-mentioned pattern of the hydrophobic patch formed in the broken line shape. The above photolithography and SAM film forming method, the stamping method, the inkjet method, and the like can appropriately used as the filter forming method.

In the case where the filter is formed in the channel, the filter surface may be formed in the direction perpendicular to the flow direction, and the filter surface may be formed in parallel with the flow direction. When the filter surface is formed in parallel with the flow direction, compared with the case in which the filter surface is perpendicular to the flow direction, there are advantages that filter is hardly clogged with the substance and the wide area is assured in the filter. In this case, the width of the channel portion is widened, e.g. the width is set at 1000 μm, square hydrophobic patches of 50 μm by 50 μm are formed at intervals of 50 μm in the flow direction of the channel, which allows the channel to be divided into two portions in parallel with the flow direction. When the liquid containing the substance to be separated is introduced from one side of the divided channels, the filtered liquid in which the substances larger than 50 μm contained in the liquid are removed flows out from the other channel. Therefore, the substance can be condensed one side of the channels.

Tenth Embodiment

Figure 72:
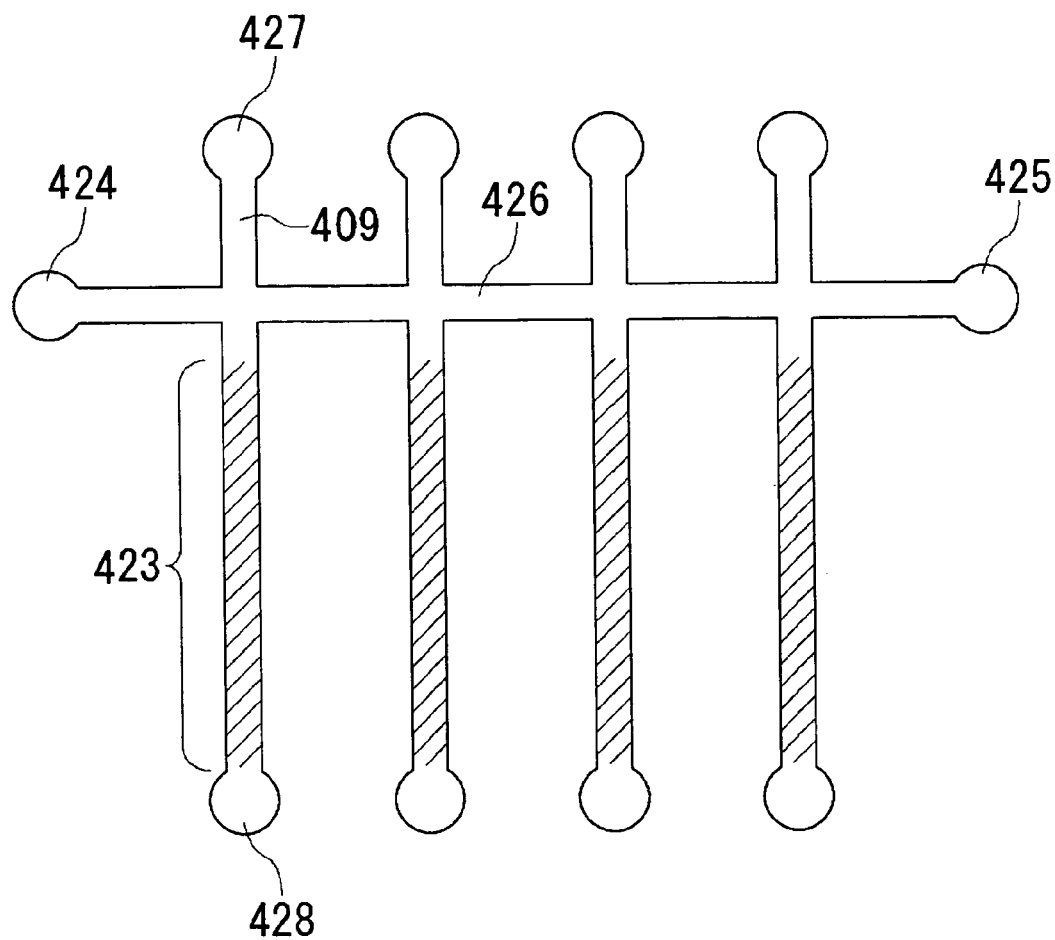
FIG. 72 is a view showing an example of a configuration of a channel in the microchip.
Figure 73:
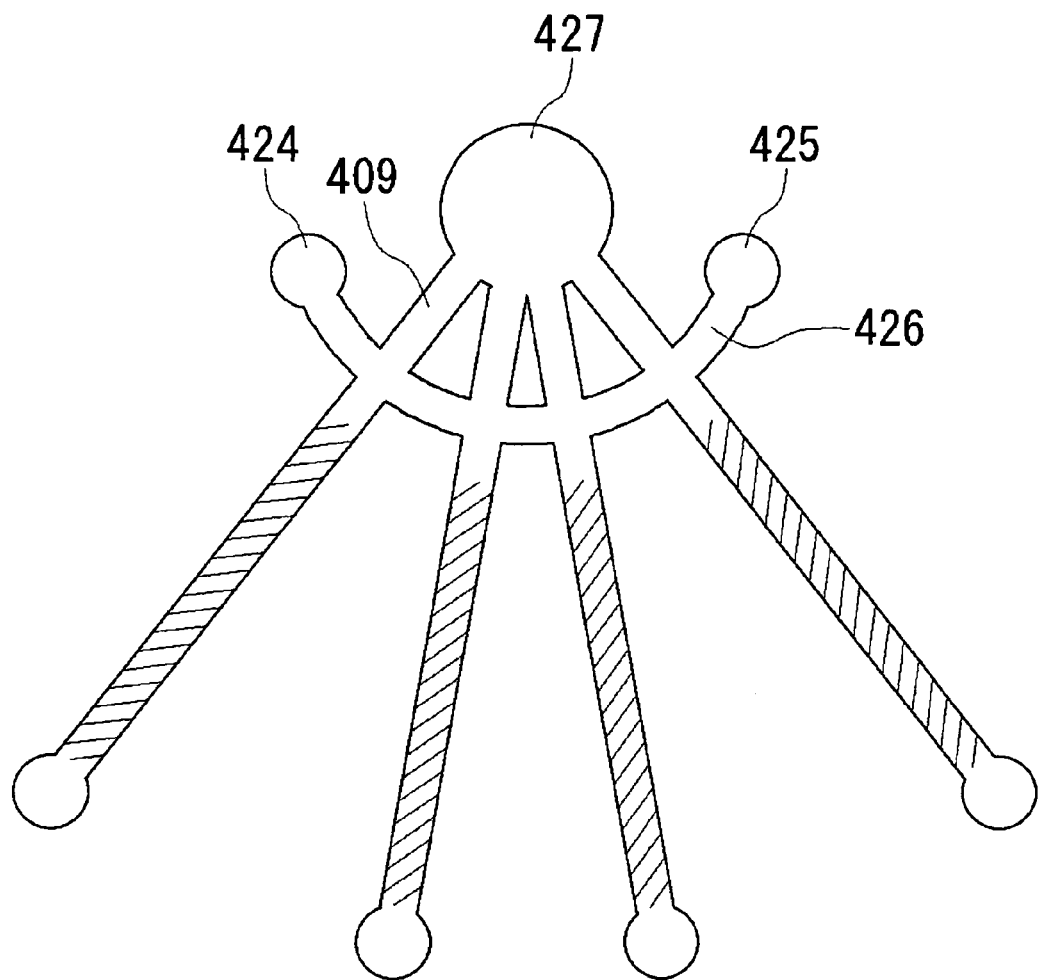
FIG. 73 is a view showing an example of a configuration of the channel in the microchip.

The mode, in which the plural channels having the separation areas are provided and a sample introducing channel which intersects the channels and introduces the sample into the separation areas is provided, can be adopted as the microchip used for the mass spectrometry system 351. FIG. 72 shows an example of the channel configuration. The plural channels 409 having separation areas 423 are provided in the channel configuration. The separation area 423 includes the columnar bodies, concaves, or hydrophilic/hydrophobic areas. The separation target sample is introduced from a sample inlet 424 and diffused toward a reservoir 425. The separation ability is not imparted to a channel 426 between the sample inlet 424 and the reservoir 425, and the channel 426 is used in order to transport the sample to the plural channels 409 without having the separation abilitys. After the channel 426 is filled with the sample, the simultaneous separation can be performed by causing the sample to migrate from a reservoir 427 to a reservoir 428. Therefore, the separation efficiency is improved. The channels 409 include the separation areas 423 having the different characteristics, which enables the sample to be simultaneously separated according to various characteristics. As shown in FIG. 73, it is also possible to adopt the mode in which one reservoir 427 is formed. This example is efficient because the buffer solution can be injected from the reservoir 427 to all the channels 409.

The configurations shown in FIGS. 72 and 73 can be adopted when the mode of the sample separation portion is any one of the first to ninth embodiments. In the modes shown in FIGS. 72 and 73, as described in the fifth embodiment, it is also possible that the pillar mesh is arranged at the point where the channels in which the separation area is provided and the sample introducing channel intersect each other. FIG. 74 shows an example. At the intersection point between the channel 409 and the channel 426, plural fine pillars are arranged in a pillar mesh 429. The pillar mesh 429 has a filtering function. The pillar mesh 429 can pass only the molecules having the sizes of the desired range to the separation area 423 by controlling a pillar pitch. Therefore, the desired analysis can rapidly and correctly be performed. In FIG. 74, the channels in which the separation area is provided and the sample introducing channel are orthogonal to each other, however, it is not limited thereto, the above effect can be obtained even in the configuration in which the channels in which the separation area is provided and the sample introducing channel intersect at an arbitrary angle.

In the case where the pillar mesh 429 is included, when the weak drive force (for example, extremely weak electric field) is imparted to the separation target molecular group, the sample widened as shown in FIG. 75 (*a*) before the migration is started is dammed by the pillar mesh 429. Therefore, the molecular group is condensed as shown in FIG. 75 (*b*) to form the thin band. Then, when the strong drive force (for example, strong electric field) is temporarily imparted to the separation target molecular group, the molecular group passes through the pillar row while holding the condensed state. That is, in the case of the macromolecule such as DNA and protein, even if the molecular size is larger than the interval between the pillars, the molecule can scrape through the interval between the pillars by the molecular extension when the pillar row is formed in one or several lines (reptation effect). Because the molecular group holds the thin band state, the peak overlap is decreased after the separation, which allows the separation to be realized with high accuracy. There is also the advantage that the charging channel is not required because the sufficiently thin band is obtained even if the sample is directly inputted to the reservoir 427 of the channel 409.

In FIGS. 74 and 75, the channels in which the separation area is provided and the sample introducing channel are orthogonal to each other, however, they are not limited thereto, and the above effect can be obtained even in the configuration in which the channels in which the separation area is provided and the sample introducing channel intersect at an arbitrary angle.

Eleventh Embodiment

In the microchip applied to the mass spectrometry system 351 of FIG. 1, the sample separation portion may be configured by causing the fine particles for adsorbing the sample to adhere to the substrate. FIG. 76 (*a*) is a top view of the microchip according to this embodiment, and FIG. 76 (*b*) is a view for explaining the state of the section taken on line E-E' of a sample separation portion 347 of FIG. 76 (*a*). Referring to FIG. 76 (*a*), the separation channel 112 is provided in the substrate 110, and the liquid reservoirs 101*a* and 101*b* are formed at the both ends of the separation channel 112. The sample separation portion 347 which is filled with the fine particles is provided in the separation channel 112. The material used as the adsorption agent in TLC (Thin Layer Chromatography) and the like can be used as the fine particle with which the sample separation portion 347 is filled. Specifically, for example, silica gel, alumina, and cellulose are used, and the particle diameter can be set in the range of 5 to 40 nm.

For example, in the case where silica gel is used as the fine particle, after a damming member is provided on the downstream side of the separation channel 112, the mixture of silica gel powder, a binder, and water is poured into the channel, and the mixture is dried and solidified. Therefore, the sample separation portion 347 can be filled with the silica gel powder.

The separation with the microchip having the sample separation portion 347 is performed as follows. In the state in which the microchip is dried, spotting of the sample is performed from the top face into the end portion on the liquid reservoir 101a side of the sample separation portion 347. For example, the spotting amount of the sample is set in the rage of about 1 µL to about 10 µL. Therefore, the sufficient amount of sample can be secured in order to perform the mass spectrometric analysis. When a spot width is preferably formed, the preferable separation ability is exhibited. When the predetermined amount of developing solution is introduced in the liquid reservoir 101a at the stage in which the sample is dried to a certain extent, the developing solution is introduced into the separation channel 112 by the capillarity. Then, the developing solution is penetrated from the separation channel 112 to the gap between the fine particles in the sample separation portion 347 by the capillarity.

At this point, the spotted sample is moved to the sample separation portion 347 by the flow of the developing solution which is penetrated toward the downstream, i.e. the liquid reservoir 101b side through the sample separation portion 347. The higher affinity for the developing solution has the component in the sample, the faster the component is moved. That is, the component is developed according to the affinity. After the components in the sample are separated, similarly to the first embodiment, when the sample is irradiated along the sample separation portion 347 with the laser beam, the mass spectrometric analysis can be performed for each component of the sample. In the method of the invention, since the sample separation portion 347 is rapidly dried after the development, the transfer to the mass spectrometric analysis step can further efficiently be performed In FIG. 76 (a), the separation channel 112 is filled with the fine particles. However, it is also possible to adopt the configuration in which the adsorbent is caused to adhere to the surface of the substrate. The invention is not particularly limited to the configuration in which the channel is provided.

Twelfth Embodiment

This embodiment relates to another configuration of the mass spectrometry system. In the microchips described in the first to eleventh embodiments, the microchip having an arbitrary configuration can be applied to the mass spectrometry system of this embodiment. The microchip, which has the channel configuration of microchip 307 shown in FIG. 21 and separation channel 112 in which the pillars 125 shown in FIG. 6 are arranged, will be described below as an example. It is also possible to use the separation channel 112 described in the fourth embodiment in which the pillar patches are formed.

Figure 77:
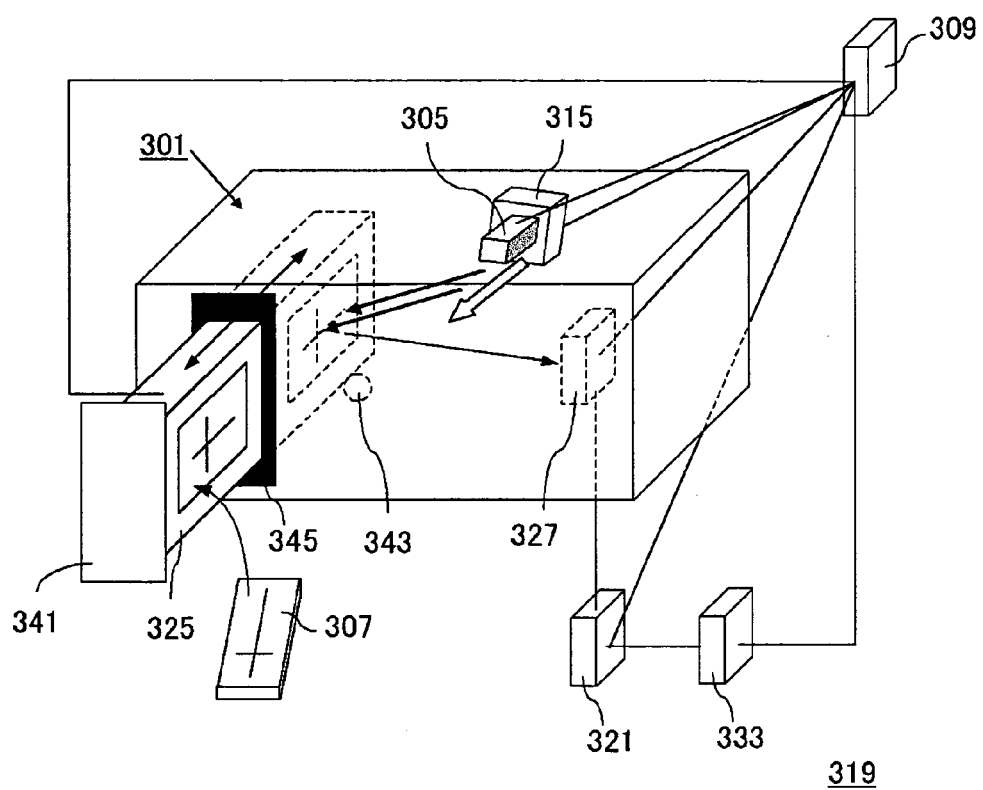
FIG. 77 is a view showing a configuration of the mass spectrometry system according to an embodiment.

FIG. 77 is a schematic view showing the configuration of the mass spectrometry system according to this embodiment. Referring to FIG. 77, a mass spectrometry system 319 includes a mass spectrometry apparatus 301, the microchip 307, a conversion unit 321, arithmetic processing unit 333, and a system control unit 309. The system control unit 309 manages and controls these apparatus and units. The mass spectrometry apparatus 301 includes a laser light source 305, a light source supporting unit 315, a placement stage 325, a cover 341, a packing 345, a gear 343, and a detection unit 327. The microchip 307 is placed on the placement stage 325.

The mass spectrometric analysis is performed with the mass spectrometry system 319 as follows. First the sample is separated on the channel (not shown in FIG. 77) in the microchip by the later-mentioned method using the microchip 307.

The microchip 307 is set on the placement stage 325, and the gear 343 is adjusted to insert the placement stage 325 into a chamber of the mass spectrometry apparatus 301. At this point, the cover 341 comes into close contact with the packing 345 provided on a wall portion of the chamber, which allows the vacuum to be preferably secured inside the chamber during the analysis. The placement stage 325 or the light source supporting unit 315 is adjusted to perform position alignment with the microchip 307 or the laser light source 305.

The laser beam from the laser light source 305 is scanned under vacuum along the channel in which the sample is separated, and the mass spectrometric analysis is performed for each separated component in the sample. Each separated component in the sample is vaporized in the channel of the microchip 307. The placement stage 325 is the electrode. When the voltage is applied to the electrode, the vaporized sample flies into vacuum, and the sample is detected by the detection unit 327. After A/D conversion of a detection value is performed by the conversion unit 321, the arithmetic processing unit 333 performed the predetermined analysis. It is also possible to form the configuration in which a metal film is formed on the bottom surface of the microchip to be able to be connected to the external power supply. Therefore, the voltage can be applied to the microchip.

Thus, in the mass spectrometry system 319, the sample separated by the channel on the microchip 307 is continuously analyzed on the channel. Therefore, after the sample containing the plural components is separated, the mass spectrometric analysis can efficiently be performed for each component.

Figure 78:
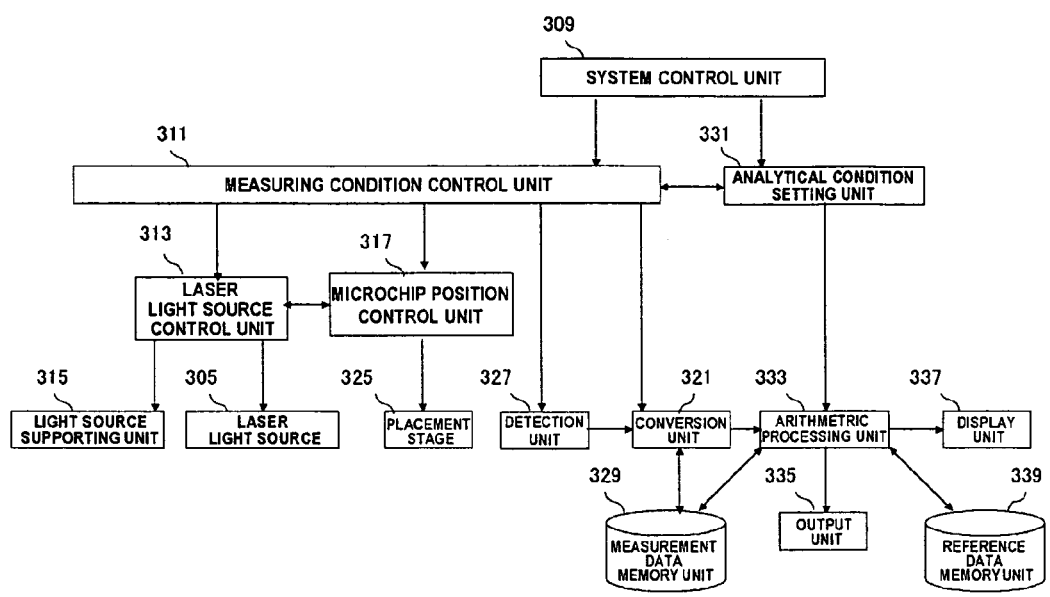
FIG. 78 is a view for explaining a method of controlling the mass spectrometry system of FIG. 77.

Then, the configuration of the mass spectrometry system including the mass spectrometry apparatus 301 and the microchip 307 and the analysis using the system will be described in detail. FIG. 78 is a view for explaining the mass spectrometry system controlling method. Referring to FIG. 78, the system control unit 309 manages a measuring condition control unit 311 and an analytical condition setting unit 331.

The measuring condition control unit 311 controls various conditions of the mass spectrometric analysis measurement. For example, the measuring condition control unit 311 controls a laser light source control unit 313, a microchip control unit 317, the detection unit 327, and the conversion unit 321. The laser light source control unit 313 controls an irradiation angle and irradiation intensity of the laser beam. In this case, the laser light source control unit 313 adjusts outgoing light intensity of the laser light source 305 and the angle or the position of the light source supporting unit 315 which supports the laser light source 305.

The microchip control unit 317 adjusts the position of the placement stage 325 on which the microchip 307 is placed. Accordingly, the separation channel 112 of the microchip 307 can securely be irradiated with the laser beam from the laser light source 305. In order to increase the alignment accuracy of the light irradiation, it is preferable that an alignment mark (not shown in FIGS. 77 and 21) is provided at a predetermined position in the microchip 307.

The detection unit 327 detects the fragment of the component ionized by the laser beam irradiation. At this point, for example, the detection unit 327 starts the detection while setting an origin at a starting time of the laser beam irradiation. Accordingly, the laser beam scan along the separation channel 112 and an ion detection signal corresponding to a scanning position are obtained. The A/D (analog-to-digital) conversion is performed to the ion detection signal detected by the detection unit 327. The data converted by the conversion unit 321 is transmitted to the arithmetic processing unit 333 to perform the data analysis. The data is stored in a measurement data memory unit 329.

The analytical condition setting unit 331 controls the arithmetic processing unit 333, and the arithmetic processing unit 333 performs the predetermined analysis. At this point, information in a reference data memory unit 339 in which comparison data and the like are stored may be referred to. The analytical result is stored in the measurement data memory unit 329. The analytical result can be outputted from an output unit 335, and displayed on a display unit 337.

Figure 79:
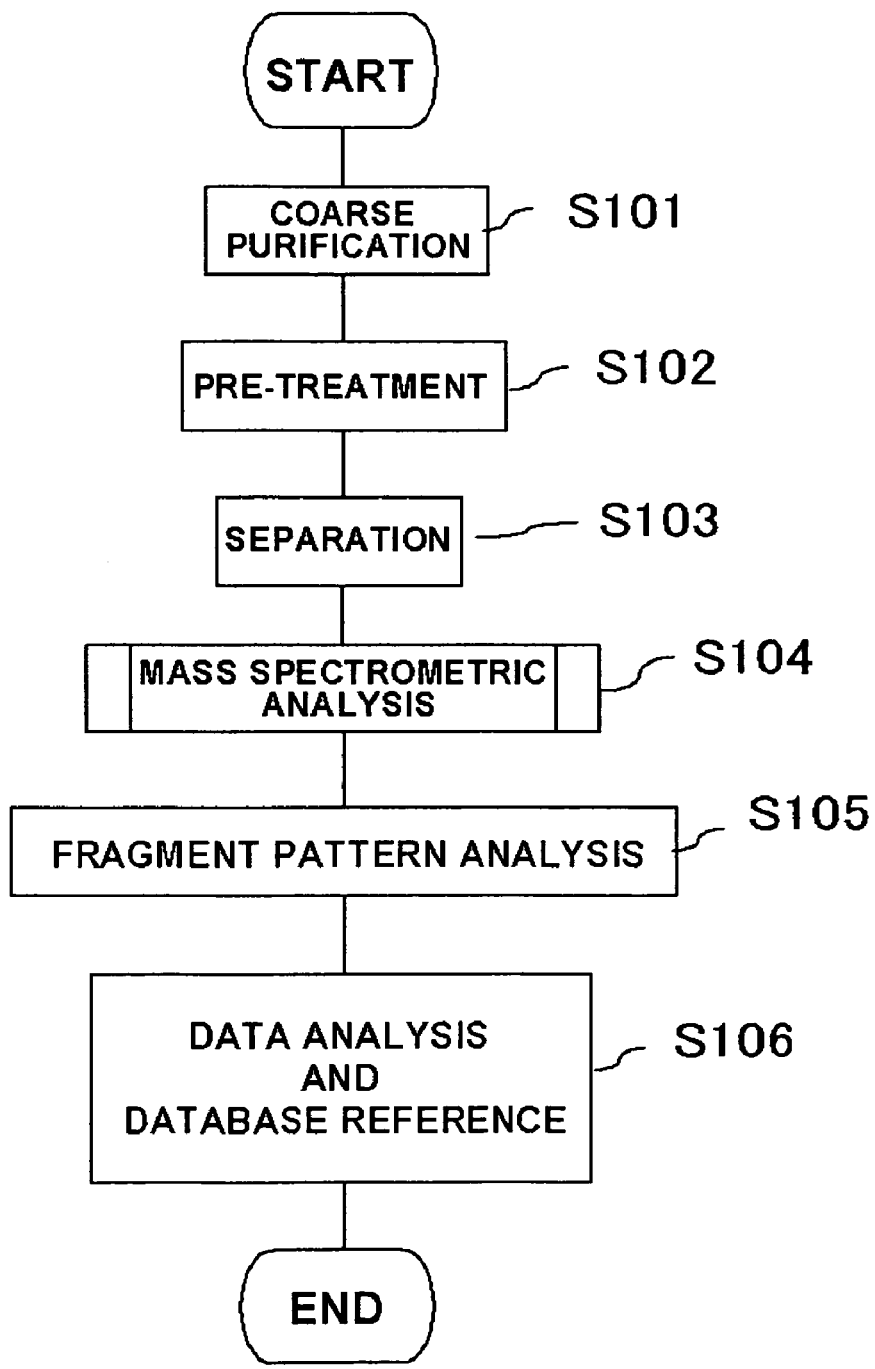
FIG. 79 is a view for explaining mass spectrometry according to an embodiment.

FIG. 79 is a view for explaining an analytical flow using the mass spectrometry system. As show in FIG. 79, coarse purification in which contaminants in the sample are removed to a certain extent is performed (S101). After the later-mentioned pre-treatment is performed as required (S102), the sample is separated (S103). The component of the laser irradiation position (band) is ionized by irradiating the sample with the laser beam along the separation channel 112, and the mass spectrometric analysis is performed (S104). After the mass spectrometric analysis, a fragment pattern is analyzed from the fragment obtained for each component (S105), and the obtained data is analyzed (S106). In the data analysis of STEP 106, a database stored in the reference data memory unit 339 is referred to.

The following process can be cited as the pre-treatment in STEP 102. For example, in the case where the mass spectrometric analysis is performed to the component having an inner disulfide bond, a reduction reaction may be performed in the solvent such as acetonitrile containing a reducing reagent such as DTT (dithiothreitol). It is preferable that a thiol group is protected by alkylation after the reduction to suppress the oxidation of the thiol group.

In the case where the component in the sample has the molecular weight higher than the molecular weight suitable for the analytical method of the mass spectrometry apparatus 301, a degradation treatment of the protein molecule may be performed with protein hydrolyzing enzyme such as trypsin. Because the degradation is performed in the buffer solution such as a phosphoric acid buffer, demineralization and macromolecule fraction, that is, removal of trypsin may be performed after the reaction. In the case where the degradation is performed, it is preferable that the reduction treatment is previously performed. Accordingly, the measurement can be performed with higher accuracy.

The tryspin treatment may be performed after the sample is separated. In the case where the tryspin treatment is performed after the sample is separated, the sample is immobilized at the separated position. Because the diffusion of the separated sample is effectively suppressed by the immobilization, the band width enlargement and the like can preferably be suppressed during the degradation. FIG. 85 is a view showing an example of the trypsin treatment method. As shown in FIG. 85 (*a*), an immobilizing layer 391 is formed on the surface of the pillar 125 formed on the substrate 110. The material described in the first embodiment can be used as the material of the pillar 125. For example, silicon or metal is used. The immobilizing layer 391 is formed by applying, e.g. the silane coupling agent having the epoxy group. A sample 451 is separated with the pillars 125 having the immobilizing layers 391, and the separation channel 112 is dried, which allows the sample 451 to be immobilized by the epoxy group of the immobilizing layer 391.

As shown in FIG. 85 (*b*), when the separated sample 451 is dipped into an enzyme solution 395 of an heat-retention bath 393 to perform an enzyme treatment at a predetermined temperature while the sample is immobilized to the separation channel 112, the sample is degraded at the separated position. Therefore, the mass spectrometric analysis result of the fragment can be obtained in each separated component.

The same samples 451 are separated by the two separation channels 112 having the same configuration. The degradation treatment is performed to the sample 451, separated by one of the separation channels 112, by the method described in FIG. 85, and the sample is irradiated with the laser beam. The sample 451 separated by the other separation channels 112 is irradiated with the laser beam without performing the degradation treatment. Therefore, two kinds of information of the fragment pattern of the component itself in the sample 451 and the fragment pattern of the degraded fragment are obtained in each component. The bands detected at the same positions of the two separation channel 112 are considered to be the same component, so that the component can more securely be identified by combining the two kinds of information to perform the analysis. The two separation channels 112 may be formed on the single microchip, or the two separation channels 112 may be formed on the different microchips.

The separation in STEP 103 is performed by the above method. STEPs 102 and 103 may be performed in the mass spectrometric analysis chamber of the mass spectrometry apparatus 301, or STEPs 102 and 103 may be performed outside the mass spectrometry apparatus 301 or in a anterior chamber. Further STEPs 102 and 103 may be performed outside the mass spectrometry apparatus 301 as appropriate.

The mass spectrometric analysis procedure in STEP 104 will be described with reference to FIGS. 78 to 80. In the case where steps to STEP 103 (FIG. 79) are performed outside the mass spectrometric analysis chamber of the mass spectrometry apparatus 301, the placement stage 325 on which the microchip 307 is set is moved to the mass spectrometric analysis chamber, and the placement stage 325 is installed in the mass spectrometric analysis chamber (S201 in FIG. 80).

Figure 80:
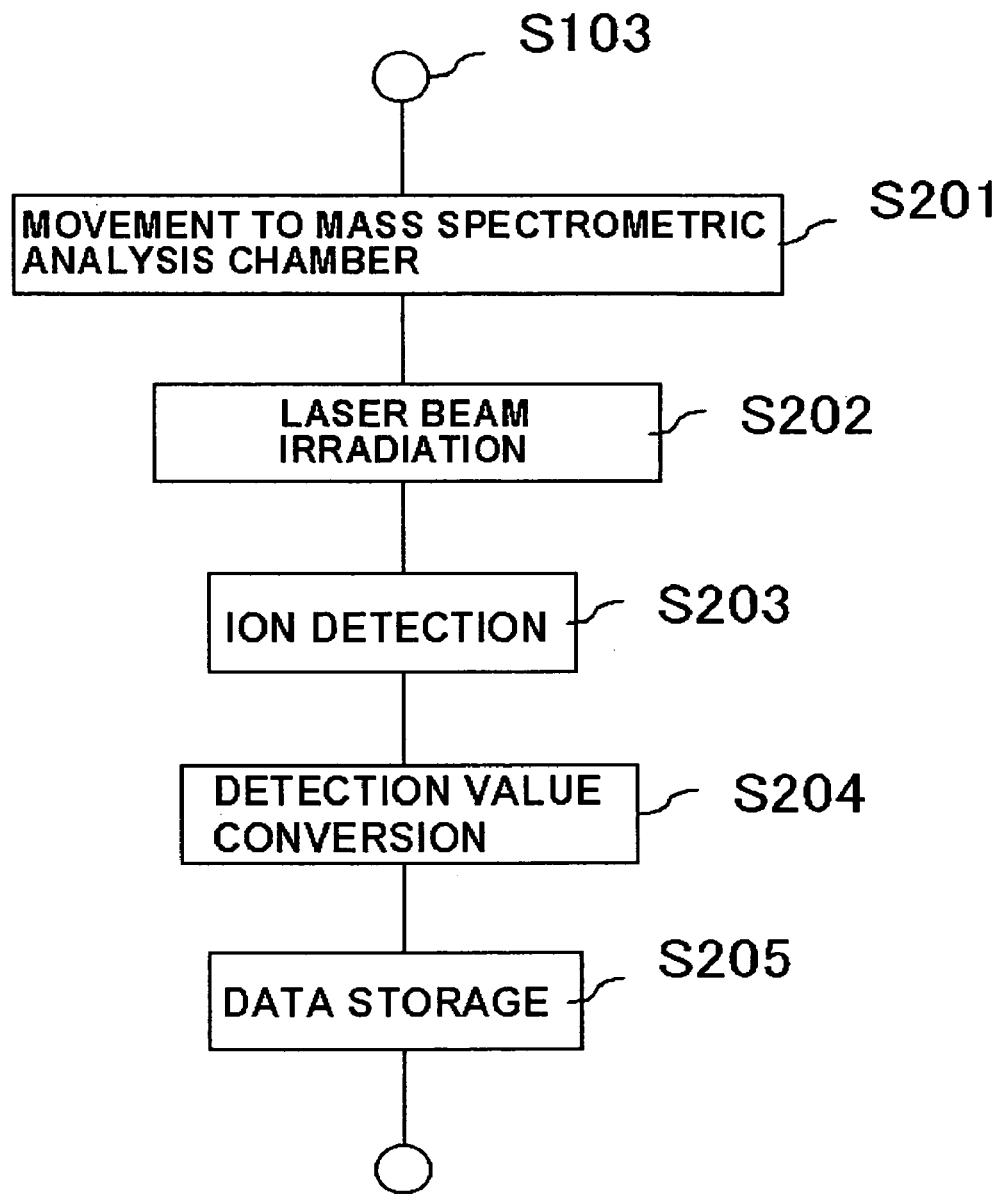
FIG. 80 is a view for explaining the mass spectrometry according to an embodiment.

Then, the microchip 307 is irradiated along the separation channel 112 with the laser beam from the laser light source 305 (S202 in FIG. 80). At this point, the placement stage 325 is used as the substrate for generating the electric field. The detection unit 327 detects a specific charge (m/z) of the ionized sample component (S203).

The predetermined conversion such as the A/D conversion is performed to the data detected by the detection unit by the conversion unit 321 (S204). The converted data is stored in the measurement data memory unit 329 (S205).

In the above mass spectrometric analysis (S104 in FIG. 79), since the pillars 125 are formed in the separation channel 112 on the microchip 307, the sample can be ionized at high efficiency without using the matrix. It is not necessary that the protein solution is mixed with the matrix solution, and the ionization can be performed by irradiating the separation channel 112 with the laser beam.

Each of STEPS 102 (pre-treatment) to STEP 104 (mass spectrometric analysis) in FIG. 79 can continuously be performed on the microchip 307. Since the laser beam is directly irradiated with along the separation channel 112, the mass spectrometric analysis can be performed while the component in each band obtained by the separation of the sample in the separation channel 112 is not moved from the separation channel 112. Therefore, even if the sample is the small amount, the steps from the separation to the mass spectrometric analysis can efficiently be performed with high accuracy.

Since the sample is separated with the pillars 125 in the separation channel 112, it is not necessary to use the filler such as gel and beads used for the conventional electrophoresis. Therefore, the vaporization is smoothly performed during the laser beam irradiation while the liquid sample is held in the separation channel 112 to suppress the drying during the separation. In the case where the filler is used, there is a possibility that the background rises during the measurement by the ionization of the filler. However, in the separation channel 112 in which the pillars 125 are used, the rise of the background is suppressed. Since the separation channel 112-derived component suppresses the ionization during the laser beam irradiation, as described in the first embodiment, it is preferable that the silicon thermal oxide film is used for the hydrophilic treatment of the surface of separation channel 112.

The mass spectrometric analysis may be performed by the method in which the matrix is used. The matrix is appropriately selected according to the measurement target substance. For example, the substances described in the first embodiment can be used.

Figure 81:
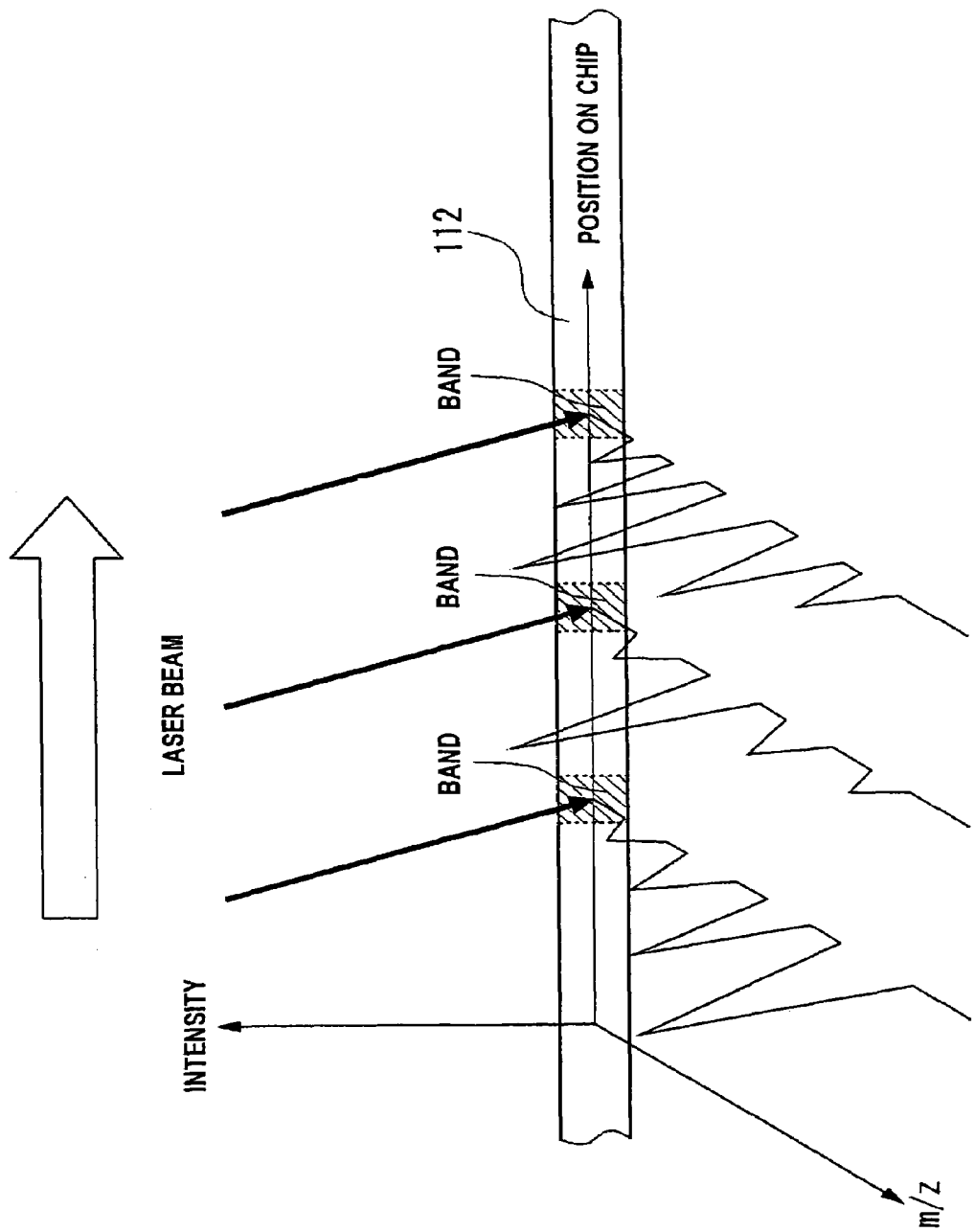
FIG. 81 is a view for explaining a method of analyzing a fragment pattern obtained by mass spectrometric analysis according to an embodiment.

The analysis of the fragment pattern in STEP 106 of FIG. 79 is performed by the arithmetic processing unit 333 shown in the FIG. 78. An example of the fragment pattern analyzing method in STEP 106 will be described with reference to FIGS. 81 and 82. FIG. 81 is a view showing the mass spectrometric analysis fragment pattern which is obtained in each separated component in the separation channel 112. FIGS. 82A and 82B are the fragment patterns obtained for the samples extracted from the different specimens.

In FIG. 81, in the case where the sample is separated based on the molecular weight, each component in the sample can be analyzed by producing a two-dimensional map concerning the position on the separation channel 112 and the molecular weight. That is, FIGS. 82A and 82B show the two-dimensional map while the position on the chip is set at the longitudinal axis and the molecular weight is set at the transverse axis. For the longitudinal axis, m/z having the maximum (peak) detection intensity is shown by black-lacquered in the fragment pattern of each component. Accordingly, the different component and different region can easily be specified between the specimens by utilizing the difference in fragment pattern between FIGS. 82A and 82B. It is because, for example, in the case where variation is generated in the predetermined protein, DNA and the like, the fragment which becomes the peak is changed in the fragment pattern when the mass spectrometric analysis is performed to component. The component and the region in which the variation is generated can be identified by the fragment pattern analysis. The analytical result can be provided as a useful guideline for diagnosis and the like. Further, the analytical result can also be applied to the screening of a valuable substance and the like.

Thus, the steps from the sample separation to the identification of each component are rapidly realized with high accuracy by the mass spectrometry system 319. Even if the sample is the extremely small amount, the sensitive detection can be performed to each component. The fragment pattern of each component can efficiently be obtained, and the result can efficiently be analyzed. Therefore, a wide variety of information can be obtained.

In the mass spectrometry system 319, the separation is performed outside the mass spectrometry apparatus 301 and it is set in the mass spectrometric analysis chamber of the mass spectrometry apparatus 301. However, it is also possible to adopt the configuration in which the anterior chamber is provided in the mass spectrometry apparatus 301.

Figure 83:
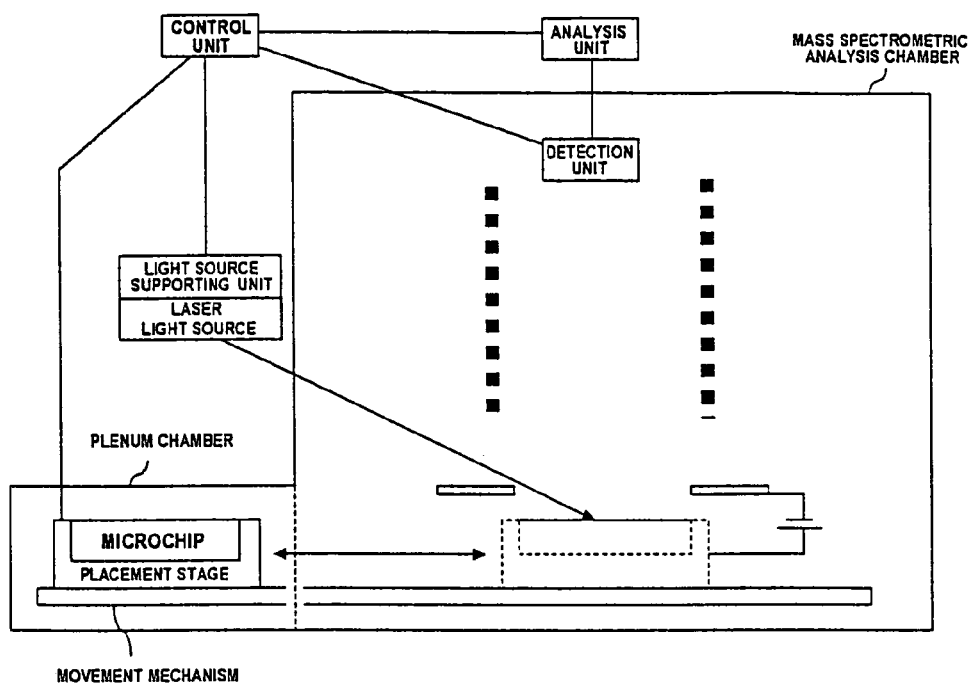
FIG. 83 is a view showing a configuration of the mass spectrometry system according to an embodiment.

FIG. 83 is a view showing another configuration of the mass spectrometry system. Referring to FIG. 83, the anterior chamber adjacent to the mass spectrometric analysis chamber is provided, and the sample separation is performed with the microchip outside the apparatus or in the anterior chamber. Therefore, in the mass spectrometric analysis chamber, the pressure can previously be reduced.

After the separation, the pressure is reduced in the anterior chamber having the placement stage on which the microchip is set. Because the anterior chamber is small when compared with the mass spectrometric analysis chamber, the pressure rapidly reaches a predetermined degree of vacuum. The placement stage is moved from the anterior chamber to the mass spectrometric analysis chamber by a movement mechanism, and the placement stage is set at the predetermined position.

As with the mass spectrometry system 319 (FIG. 77), the component ionization in the channel is performed by irradiating the sample along the channel (not shown) with the laser beam from the laser light source. The fragment, which is ionized by imparting the predetermined voltage while the placement stage is used as the substrate, reaches the detection unit, and the fragment is detected. The detection value is analyzed by the analysis unit. The control unit controls the placement stage, the light source supporting unit, the laser light source, the detection unit, and the analysis unit.

Thus, since the mass spectrometry system of FIG. 83 includes the anterior chamber, the separation and the mass spectrometric analysis can continuously and efficiently be performed.

As described above, the invention is explained based on the embodiments. While these embodiments are given only as an example, those skilled in the art will recognize that various modifications may be made without departing from the scope of the invention.

For example, in the above embodiments, the sample is separated in the separation channel 112 according to the molecular weight of the component. However, instead of the molecular weight, the separation can also be performed by the isoelectric point of the sample.

In the case where the separation is performed by the isoelectric point, the sample is previously mixed with the predetermined buffer. As used herein the buffer should mean the solution which forms a pH gradient when the electric field is applied. The solution containing Ampholine or Pharmalyte (product of Amersham Biosciences KK) can be cited as an example. In the case where the separation is performed with the microchip 307 of FIG. 21, the solution is inputted in the liquid reservoir 101a or the liquid reservoir 101b, and the solution is introduced to the separation channel 112.

The sample may be introduced from the side with respect to the direction of the electric field generated in the separation channel 112. That is, the sample containing an isoelectric-point electrolyte can also be introduced from the liquid reservoir 102a or 102b. Because the isoelectric-point electrolyte is contained in the sample, the pH gradient is formed in the separation channel 112 by affection of the electric field. Therefore, in the separation channel 112, the introduced sample converges in the band according to the isoelectric point of each component.

The invention claimed is:
1. A mass spectrometry system comprising:
 a microchip which has a channel through which a sample passes and a sample separation area being provided in said channel;

a light irradiation unit irradiating with a laser beam while moving a light irradiation position along said sample separation area; and an analytical unit analyzing a fragment of said sample to obtain mass spectrometric data, said fragment of said sample being generated by a light irradiation, wherein said channel is provided on a surface of a substrate, said sample separation area has a plurality of columnar bodies, and said sample separation area having said plurality of columnar bodies is irradiated with said laser beam.

2. The mass spectrometry system according to claim 1, wherein the density of said plurality of columnar bodies is gradually decreased toward a proceeding direction of said sample in said channel.

3. The mass spectrometry system according to claim 1, wherein the density of said plurality of columnar bodies is gradually increased toward a proceeding direction of said sample in said channel.

4. The mass spectrometry system according to claim 1, wherein said sample separation area and an adjustment area are alternately formed with respect to a proceeding direction of said sample in said channel, said plurality of columnar bodies being formed less densely in said adjustment area than in said sample separation area.

5. The mass spectrometry system according to claim 1, wherein a metal layer is provided on a surface of at least one of said columnar bodies.

6. The mass spectrometry system according to claim 1, wherein at least one of said columnar bodies is made of metal.

7. The mass spectrometry system according to claim 1, wherein said laser beam is an infrared laser beam or an ultraviolet laser beam.

8. The mass spectrometry system according to claim 1, wherein said sample separation area includes a plurality of columnar body arrangement portions in which said plurality of columnar bodies are arranged, and a path is provided between said plurality of adjacent columnar body arrangement portions, said sample passing though said path.

9. The mass spectrometry system according to claim 8, wherein a width of said path is larger than an average interval between said plurality of columnar bodies in said plurality of columnar body arrangement portions.

10. The mass spectrometry system according to claims 8 or 9, wherein said plurality of columnar body arrangement portions are combined and arranged such that a plane arrangement is to be a substantial rhombus, and said plurality of columnar bodies are arranged such that said plane arrangement of each of said plurality of columnar body arrangement portions is to be a substantial rhombus.

* * * * *